(12) United States Patent
Fischer et al.

(10) Patent No.: US 6,992,169 B2
(45) Date of Patent: *Jan. 31, 2006

(54) CARRIER BASED DRUG DELIVERY SYSTEM

(75) Inventors: Peter M. Fischer, Angus (GB); Shudong Wang, Forfar (GB); Nikolai Zhelev, Newport-on-tay (GB)

(73) Assignee: Cyclacel Limited, Scotland (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/210,660

(22) Filed: Jul. 31, 2002

(65) Prior Publication Data

US 2003/0119735 A1 Jun. 26, 2003

Related U.S. Application Data

(63) Continuation of application No. 09/346,847, filed on Jul. 2, 1999, now Pat. No. 6,472,507.

(30) Foreign Application Priority Data

Jul. 3, 1998 (GB) .............................. 9814527

(51) Int. Cl.
*A61K 38/08* (2006.01)
*A61K 38/10* (2006.01)
*C07K 7/06* (2006.01)
*C07K 7/08* (2006.01)

(52) U.S. Cl. ............................ 530/326; 514/2; 514/13; 514/14; 514/15; 514/16; 530/327; 530/328; 530/329; 530/345

(58) Field of Classification Search .................... 514/2, 514/13, 14, 15, 16, 21; 530/300, 326, 327, 530/328, 329, 345; 424/1.69, 9.1, 9.34, 9.341, 424/9.4, 9.411, 9.42; 435/29
See application file for complete search history.

(56) References Cited

U.S. PATENT DOCUMENTS

| | | | | |
|---|---|---|---|---|
| 4,847,240 | A | * 7/1989 | Ryser et al. | 514/12 |
| 5,043,329 | A | 8/1991 | Lichtenberger | 514/78 |
| 5,179,086 | A | 1/1993 | Flander | 514/182 |
| 5,580,563 | A | * 12/1996 | Tam | 424/197.11 |
| 5,888,762 | A | * 3/1999 | Joliot et al. | 435/69.1 |
| 6,015,787 | A | * 1/2000 | Potter et al. | 514/12 |
| 6,025,140 | A | * 2/2000 | Langel et al. | 435/6 |
| 6,080,724 | A | * 6/2000 | Chassaing et al. | 514/13 |
| 6,472,507 | B1 | * 10/2002 | Fischer et al. | 530/326 |

FOREIGN PATENT DOCUMENTS

| | | |
|---|---|---|
| EP | 0 485 578 B1 | 10/1996 |
| EP | 0 751 225 B1 | 1/1997 |
| GB | 2340121 | 2/2000 |
| WO | WO 91/18981 A2 | 12/1991 |
| WO | WO 95/33766 A1 | 12/1995 |
| WO | WO 95/34295 A1 | 12/1995 |
| WO | WO-97/12912 A1 * | 4/1997 |
| WO | WO 97/12912 A1 | 4/1997 |
| WO | WO 97/19954 A1 | 6/1997 |
| WO | WO 97/25070 A3 | 7/1997 |
| WO | WO 97/25070 A2 | 7/1997 |
| WO | WO-98/13059 A1 * | 4/1998 |
| WO | WO 98/13059 A1 | 4/1998 |
| WO | WO 98/38861 A1 | 9/1998 |
| WO | WO 98/56938 A1 | 12/1998 |
| WO | WO 99/05302 A1 | 2/1999 |
| WO | WO-99/11809 A1 * | 3/1999 |
| WO | WO 99/11809 | 3/1999 |
| WO | WO 00/001417 A1 | 1/2000 |

OTHER PUBLICATIONS

Brugidou et al. The Retro–Inverso Form Of A Homeobox–Derived Short Peptide . . . Biochemical And Biophysical Research Communications. Sep. 14, 1995. vol. 214, No. 2, pp. 685–693.*

Derossi, D., et al. "The third helix of the antennapedia homeodomain translocates through biological membranes." *The Journal of Biological Chemistry.* 1994; 269(14):10444–50.

Derossi, D., et al. "Cell internalization of the third helix of the antennapedia homeodomain is receptor–independent." *The Jouranl of Biological Chemistry.* 1996; 271(30):18188–93.

Fischer, P.M., et al. "Structure–activity relationship of truncated and substituted analogues of the intracellular delivery vector penetratin." *J Pept Res.* Feb. 2000; 55(2):163–72.

Plank, C. "Branched cationic peptides for gene delivery: role of type and number of cationic residues in formation and in vitro activity of dna polyplexes." *Human Gene Therapy.* 1999; 10:319–32.

Simmons, C.G. "Synthesis and membrane permeability of pna–peptide conjugates." *Bioorganic & Nedicinal Chemistry Letters.* 1997; 7(23)3001–6.

Schutze–Redelmeier, M.P., et al. "Introduction of exogenous antigens into the MHC Class I processing and presentation pathway by drosophila antennapedia homeodomain primes cytotoxic T cells in vivo." *The Journal of Immunologists.* 1996; 651–5.

(Continued)

*Primary Examiner*—Jeffrey Edwin Russel
(74) *Attorney, Agent, or Firm*—Lahive & Cockfield, LLP; Giulio A. Deconti, Jr.; Cynthia L. Kanik

(57) ABSTRACT

The present invention relates to a novel drug delivery system of use in the improved delivery of drug therapeutic agents into target cells. The system comprises a drug moiety linked to a carrier moiety wherein the carrier moiety comprises a homeobox peptide or a fragment or derivative thereof.

40 Claims, 2 Drawing Sheets

OTHER PUBLICATIONS

U.S. Appl. No. 09/438,460, filed Nov. 12, 1999, Fischer et al.

U.S. Appl. No. 09/854,204, filed May 11, 2001, Fischer et al.

Brugidou, J. et al. (1995) "The Retro–Inverso Form of a Homobox–Denved Short Peptide Is Rapidly Internalised by Cultured Neurones: A New Basis For An Efficient Intracellular Delivery System" Biochemical and Biophysical Research Communications, vol. 214, No. 2, pp. 685–693.

Derossi, Daniele et al. (1998) "Trojan Peptides: The Penetratin System For Intracellular Delivery" Trends in Cell Biology, vol. 8, pp. 84–87.

Prochiantz, Alain (1996) "Getting Hydrophilic Compounds Into Cells, Lessons From Homeopeptides" Current Opinion in Neurobiology, vol. 6, pp. 629–634.

* cited by examiner

CARRIER BASED DRUG DELIVERY SYSTEM

RELATED APPLICATIONS

This application is a continuation application of Ser. No. 09/346,847 filed on Jul. 2, 1999, and issued as U.S. Pat. No. 6,472,507B1 on Oct. 29, 2002, which claims benefit of GB 98/14527.9 filed on Jul. 3, 1998. The contents of all of the aforementioned application(s) are hereby incorporated by reference.

BACKGROUND

The pharmaceutical industry has for many years concerned itself with the efficient delivery of therapeutic agents. This problem may be attributed to the short clearance time of the agent in the body (short half-life), the location of the site of action or possibly the nature of the therapeutic agent itself, for example, its solubility, hydrophobicity etc. Thus, many developments and strategies have been adopted, including formulating the therapeutic agent so as to protect it from a hostile environment on route to its site of action, by for example, enterically coated tablets, controlled release devices and the like.

The development of peptide derived therapeutic agents has posed a further problem due their susceptibility to enzymatic degradation not only in the GI tract but also in the bloodstream. An example of how this problem has been addressed relates to the incorporation of the peptides into liposomes or polymeric microspheres that target the peptides to the lymph system.

A further related problem, especially for therapeutic agents that function intracellularly is the barrier posed by the cell membrane. Thus, it may be possible to increase the half life of the agent or ensure that it passes through the body without being degraded, but many agents must actually enter cells to exert their therapeutic effect.

European Patent 485578 discloses that the homeodomain and specifically, helix 3 of a homeobox peptide, particularly that derived from the *Drosophila Antennapedia*, is of use as an intracellular transport vector. The patent disclosed that a specific 57 amino acid sequence of a *Drosophila Antennapedia* homeopeptide (referred to as the pAntp peptide) was capable of penetrating fibroblasts and embryo cells (in vivo). Emphasis was placed upon the last 27 amino acids of the sequence that correspond with the helix 3 and 4. There is no description of the pAntp peptide being linked to any other peptide or therapeutic agent.

Subsequent disclosures (Derossi D et al., J Biol Chem (1994) 269, 10444–10450, Joliot A H et al., (1991) The New Biol 3, 1121–1134 and PNAS (1991) 88, 1864–1868, Perez F et al., J Cell Sci (1992) 102, 712–722), all disclose how a 16 amino acid synthetic peptide derived from the third helix of the *Antennapedia* homeodomain may be used for the intracellular delivery of bioactive products and antisense oligonucleotides. The amino acid sequence of use is RQIKIFQNRRMKWKK (SEQ ID No. 1) also known as Penetratin®.

In an effort to prevent the enzymatic cleavage of this peptide Brugidou J et al., (Biochem Biophys Res Comm (1995) 214(2), 685–693) prepared a retro-inverso form (D amino acids in reverse order) of SEQ ID No. 1, substituting the two isoleucine resides at positions 3 and 5 of penetratin with valine and adding a glycine residue at the C-terminus to facilitate binding to a resin. A further retro-inverso form was prepared replacing the extra glycine with a cholesterol moiety attached via a sulfhydryl linker group. The addition of the cholesterol moiety improved penetration due to the increased hydrophobicity of the molecule.

This development of the retro-inverso form of penetratin has given rise to WO 97/12912 that discloses peptides of 16 amino acids comprising between 6 and 10 hydrophobic amino acids wherein the sixth amino acid from either end is tryptophan. This disclosure attempts to define the minimal characteristics of sequences capable of acting as internalisation vectors.

Penetratin, its analogues and retro-inverso forms have therefore been described as being of use as a carrier to facilitate the cellular internalisation of conjugated peptides or oligonucleotides.

SUMMARY OF THE INVENTION

The present invention aims to provide a delivery system for therapeutic drugs that is capable of facilitating the internalisation of the drug into cells, thus enhancing the delivery and/or therapeutic effect of the drug. The delivery system may also improve the half-life of the drug in the human or animal body, improve its solubility in biological fluids, minimise known toxic or non-desirable side-effects, enhance the onset of action of the desired therapeutic effect, provide alternative routes for the administration of the drug, enhance the biodistribution and metabolism of the drug moiety and decrease the incidence of drug resistance.

The present invention relates to a novel drug delivery system of use in the improved delivery of drug therapeutic agents into target cells. The delivery system provides other benefits that include enhancement in terms of the metabolism, distribution and excretion of the drug. The delivery system may be therapeutically active in both its intact and dissociated states.

Thus, the invention relates to a delivery system comprising a drug moiety linked to a carrier moiety comprising a homeobox peptide or a fragment or derivative thereof. As is discussed hereinafter, the drug moiety is not a peptide or oligonucleotide and the carrier moiety may be a derivative of penetratin.

DESCRIPTION OF THE PREFERRED EMBODIMENTS

Figure 1:
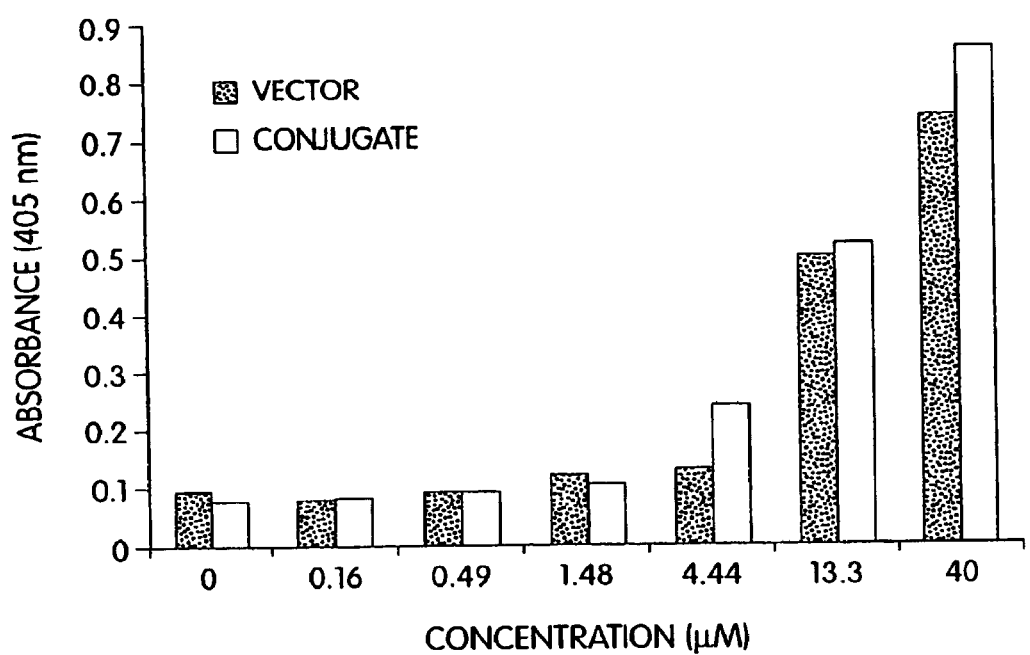
FIG. 1 shows the comparison of cell internalisation of a delivery system of the present invention compared to the carrier moiety alone.

In a first embodiment, the delivery system comprises a drug moiety linked to a carrier moiety. The drug moiety may be directly or indirectly linked to the carrier moiety. In the preferred embodiment wherein the drug moiety is indirectly linked to the carrier, the linkage may be by an intermediary bonding group such as a sulphydryl or carboxyl group or any larger group, all such linking groups and others described below, are hereinafter referred to as linker moieties.

In accordance with the present invention, suitable drug moieties include any therapeutically active non-peptide/ oligonucleotide drug. Thus, the drug moiety may be selected from cytotoxic agents, anti-neoplastic agents, anti-hypertensives, cardioprotective agents, anti-arrhythmics, ACE inhibitors, anti-inflammatory's, diuretics, muscle relaxants, local anaesthetics, hormones, cholestrol lowering drugs, anti-coagulants, anti-depressants, tranquilizers, neuroleptics, analgesics such as a narcotic or anti-pyretic analgesics, anti-virals, anti-bacterials, anti-fungals, bacteriostats, CNS active agents, anti-convulsants, anxiolytics, antacids, narcotics, antibiotics, respiratory agents, anti-histamines, immunosuppressants, immunoactivating agents, nutritional additives, anti-tussives, diagnostic agents, emetics and anti-emetics.

Preferably the drug moiety is a cytotoxic or anti-neoplastic agent, particularly those which are used for cancer therapy or such drug in photoactivatable form. Such drugs include, in general, DNA damaging agents, anti-metabolites, anti-tumour antibiotics, natural products and their analogues, dihydrofolate reductase inhibitors, pyrimidine analogues, purine analogues, cyclin-dependent kinase inhibitors, thymidylate synthase inhibitors, DNA intercalators, DNA cleavers, topoisomerase inhibitors, anthracyclines, vinca drugs, mitomycins, bleomycins, cytotoxic nucleosides, pteridine drugs, diynenes, podophyllotoxins, platinum containing drugs, differentiation inducers, and taxanes. Particularly useful members of those classes include, for example, methotrexate, methopterin, dichloromethotrexate, 5-fluorouracil, 6-mercaptopurine, trisubstituted purines such as olomoucine, roscovitine, bohemine and purvalanol, flavopiridol, staurosporin, cytosine arabinoside, melphalan, leurosine, actinomycin, daunorubicin, doxorubicin, mitomycin D, mitomycin A, caminomycin, aminopterin, tallysomycin, podophyllotoxin (and derivatives thereof), etoposide, cisplatin, carboplatinum, vinblastine, vincristine, vindesin, paclitaxel, docetaxel, taxotere retinoic acid, butyric acid, acetyl spermidine, tamoxifen, irinotecan and camptothecin. Most preferably the drug moiety is selected from methotrexate, podophyllotoxin (and derivatives thereof), etoposide, camptothecin, paclitaxel, doxorubicin, roscovitine and bohemine.

The carrier moiety as used in the present invention may be any moiety that is capable of facilitating the cellular internalisation of the drug moiety. Suitable carrier moieties include homeobox peptides or derivatives thereof such as the helix 3 of a homeobox peptide. Preferably, the homeobox peptide is derived from the *Drosophila Antennapedia* homeoprotein, sequences homologous thereto or derivatives thereof. More preferably, the carrier moiety is penetratin or a derivative thereof. Derivatives of penetratin have been described in the literature, for example EP 485578B, that discloses sequences homologous to pAntp. Further derivatives of penetratin that may be utilised in the present invention include truncated forms and/or modified forms of penetratin described in WO97/12912, UK Patent Applications 9825000.4 filed 13 Nov. 1998 and 9902522.3 filed 4 Feb. 1999 the contents of which are hereby incorporated by reference. A preferred truncated form of penetratin is RRMKWKK (SEQ ID No. 2). Further truncated forms include moieties of up to 15 amino acid residues including the sequences such as NRRMKWKK (SEQ ID NO. 3), QNRRMKWKK (SEQ ID No. 4) and FQNRRMKWKK (SEQ ID No. 5) or more preferably a 7 amino acid peptide selected from KRMKWKK (SEQ ID No. 6), RKMKWKK (SEQ ID No. 7), RREKWKK (SEQ ID No. 8), RRQKWKK (SEQ ID No. 9), RROKWKK (SEQ ID No. 10), RRMKQKK (SEQ ID No. 11), RRMKWFK (SEQ ID No. 12), RORKWKK (SEQ ID No. 13), RRMWKKK (SEQ ID No. 14) and RRMKKWK (SEQ ID No. 15) (using standard single amino acid notation, ornithine (O), diaminobutyric acid (B), norleucine (N)).

Within the carrier moieties defined as penetratin or derivatives thereof, a further modification that is beneficial in the context of the present invention is conversion of the free carboxyl group of the carboxy terminal amino acid residue, to an carboxamide group. By way of example, when the carrier moiety is penetratin (SEQ ID No. 1) the carboxy terminal lysine residue may have its carboxyl group converted into an carboxamide group. This modification is believed to enhance the stability of the carrier moiety and hence the delivery system as a whole.

The carrier moiety may be in the L or D optically active form. As used herein, when no indication is given, the carrier is in the L form. D-penetratin is described in Brugidou J et al., (Biochem Biophys Res Comm (1995) 214(2), 685–693). The carrier moiety may also be arranged in the retro form, i.e with the amino acid residues in the reverse order to their parent sequence. Such retro forms may also exist in L and D forms. Thus, in a further preferred embodiment the carrier moiety may be D-penetratin or the D form of the truncated and/or modified forms discussed above.

The drug moiety may be attached to either end of the carrier moiety e.g. if the carrier moiety is penetratin as shown in SEQ ID No. 1 or a derivative thereof, the drug moiety may be directly or indirectly attached to the terminal lysine or arginine residues. Preferably, the drug moiety is attached to the amino terminal end of the carrier.

As discussed above the drug and carrier moieties may be linked directly or indirectly via a linker moiety. Direct linkage may occur through any convenient functional group on the drug moiety such as a hydroxy, carboxy or amino group. Indirect linkage which is preferable, will occur through a linking moiety. Suitable linking moieties include bi- and multi-functional alkyl, aryl, aralkyl or peptidic moieties, alkyl, aryl or aralkyl aldehydes acids esters and anyhdrides, sulphydryl or carboxyl groups, such as maleimido benzoic acid derivatives, maleimido proprionic acid derivatives and succinimido derivatives or may be derived from cyanuric bromide or chloride, carbonyldiimidazole, succinimidyl esters or sulphonic halides and the like. The functional groups on the linker moiety used to form covalent bonds between linker and drugs on the one hand, as well as linker and carrier moiety on the other hand, may be two or more of, e.g., amino, hydrazino, hydroxyl, thiol, maleimido, carbonyl, and carboxyl groups, etc. The linker moiety may include a short sequence of from 1 to 4 amino acid residues that optionally includes a cysteine residue through which the linker moiety bonds to the carrier moiety.

Preferably, the linker moiety includes a cysteine residue that provides the actual linkage to the carrier moiety such as to form a linkage of the type drug-(linker-Cys)-carrier. Within the context of the specification this cysteine residue is considered as a component of the linker moiety. Thus, the complete linker moiety may only be formed as a result of the drug-carrier coupling reaction as the cysteine residue component of the linker may be conveniently prepared as part of the carrier moiety. In a preferred embodiment the linker moiety is selected from (methylamino)benzoyl-Cys, succinimidobenzoyl-Cys, succinimidopropionoyl-Cys, β-alanyl-succinyl, acetyl-Cys and (4"-aminoanilino)-succinimidopropionoyl-Cys. In such preferred embodiments, the cysteine residue preferably originates as a terminal residue of the carrier moiety, whereas the non-cysteine component of the linker is coupled to the drug moiety prior to reaction with the carrier. The complete linker moiety is therefore only formed upon reacting the drug and carrier moieties together.

In a manner identical to the inclusion of a cysteine residue into the linker moiety, further amino acid residues may be included in the linker which like the cysteine residue form the connection with the carrier moiety. For example, 3 or 4 amino acid residues may be included and these preferably include the cysteine residue discussed above. Any amino acid residues may be included, it is however preferable to select the residues from cysteine, β-alanine and glycine. The inclusion of such residues is preferable, particularly including cysteine, when the carrier moiety is a truncated form of penetratin such as RRMKWKK (SEQ ID No. 2).

In use, the delivery system may dissociate by way of chemical or enzymatic cleavage between the drug and carrier moieties. Within the embodiments wherein the linker moiety includes amino acid residues, such cleavage may occur within the linker moiety itself.

In accordance with the present invention each carrier moiety is linked to at least one drug moiety. In a further embodiment, the carrier moiety is prepared such as to facilitate linkage to more than one drug moiety, each drug moiety being the same or different. For example, the carrier moiety may comprise components that themselves facilitate the attachment of more than one drug moiety such as derivatives of naturally occurring amino acids or insertion of a multi-valent synthetic amino acid, or it may be specifically adapted to do so for example by a network of branched lysine residues that may be attached to the carrier moiety as a linking group and each lysine residue may then be attached to a drug moiety. In this manner a single carrier moiety may carry up to 32 drug moieties, preferably from 2 to 10 or more preferably from 4 to 5 drug moieties. In this further embodiment each drug moiety may be directly or indirectly linked to the carrier moiety by the same or different linker moiety. When more than one different type of drug moiety is attached, it is possible to co-ordinate the ratios and dosages of the individual drugs to facilitate the administration of specific drug combinations.

Preferred examples of this embodiment include when the carrier moiety is penetratin with a network of lysine residues attached to at least one end facilitating the attachment of up to 32 drug moieties or when the carrier moiety is penetratin or a derivative thereof, such as SEQ ID No. 2 (truncated 7-mer), the linker moieties are succinimidopropionyl and the drug moieties are selected from podophyllotoxin (at both ends of the carrier moiety) or epipodophyllotoxin together with either camptothecin or paclitaxel.

In a particularly preferred embodiment of the invention, the carrier moiety is penetratin or a derivative thereof that is indirectly linked to a drug moiety selected from doxorubicin, methotrexate, podophyllotoxin (and derivatives thereof), etoposide, camptothecin, paclitaxel, doxorubicin, roscovitine and bohemine.

In a further embodiment of the invention, the delivery system may further comprise a targeting moiety. The targeting moiety is capable of directing the delivery system to the specific cell type to which it is preferable for the drug moiety to function. Thus, the targeting moiety acts as an address system biasing the bodies natural distribution of drugs or the delivery system to a particular cell type. The targeting moiety may be attached to the drug moiety or more preferably to the carrier moiety.

Suitable targeting moieties include the peptide sequences identified by E Ruoslahti et al. in U.S. Pat. No. 5,622,699; Pasqualini, R, Ruoslahti, E. Nature (London) (1996), 380, 364–366, Ruoslahti, E. Ann. Rev. Cell Dev. Biol. (1996), 12, 697–715; Arap, W, Pasqualini, R, Ruoslahti, E, Science (1998), 279, 377–380. These disclosures, which are herein incorporated by reference, described certain peptides that have been found to act as address labels to certain cell types. Such peptides when attached to either the drug or more preferably, the carrier moiety will direct the delivery system, upon arrival at which the carrier moiety will facilitate the cellular internalisation of the drug moiety.

The delivery systems described herein are novel chemical entities. Specific chemical entities disclosed herein include;

| # | | Drug moiety | Linker moiety | Carrier moiety |
|---|---|---|---|---|
| | | (methotrexate)$_4$ | ((methylamino)-benzoyl-EGβA)$_4$ | (L)$_3$βARQIKIW-FQNRRMKWKK-OH (SEQ ID No. 16) |
| | | doxorubicin | succinimido-benzoyl-C | RQIKIWFQNRR-MKWKK-OH |
| | | doxorubicin | succinimido-benzoyl-C | (D-K)(D-K)(D-W)-(D-K)(D-M)(D-R)-(D-R)(D-N)(D-Q)-(D-F)(D-W)(D-I)-(D-K)(D-I)(D-Q)-(D-R-NH$_2$) |
| | | paclitaxel | 2'-succinimido-propionoyl-C | RQIKIWFQNRRM-KWKK-OH |
| N-term | paclitaxel | 2'-succinimido-propionoyl-GCG βA | RQIKIWFQNRRM-KWKK |
| C-term | carboxy-fluorescein | | |
| | | paclitaxel | 2'-succinimido-propionoyl-C | RQIKIWFQNRRM-KWKK-NH$_2$ |
| | | paclitaxel | 2'-succinimido-propionoyl-CβA | RRMKWKK-NH$_2$ |
| | | paclitaxel | 7-succinimido-propionoyl-C | RQIKIWFQNRRM-KWKK-OH |
| | | podophyllotoxin | 4-succinimido-propionoyl-C | RQIKIWFQNRRM-KWKK-OH |
| N-term | podophyllotoxin | 4-succinimido-propionoyl-GCG βA | RQIKIWFQNRRM-KWKK |
| C-term | biotinamidocaproyl | | |
| | | podophyllotoxin | 4-succinimido-propionoyl-C | RQIKIWFQNRRM-KWKK-NH$_2$ |

-continued

| # | Drug moiety | Linker moiety | Carrier moiety |
|---|---|---|---|
| | podophyllotoxin | 4-succinimido-propionoyl-C | (D-R)(D-Q)(D-I)-(D-K)(D-I)(D-W)-(D-F)(D-Q)(D-N)-(D-R)(D-R)(D-M)-(D-K)(D-W)(D-K)-(D-K-NH$_2$) |
| | podophyllotoxin | 4-succinimido-propionoyl-CβA | RRMKWKK-NH$_2$ |
| | podophyllotoxin | 4-succinimido-propionoyl-CβA | (D-R)(D-R)(D-M)-(D-K)(D-W)(D-K)-(D-K-NH$_2$) |
| | epipodophyllotoxin | 4'-succinimido-propionoyl-C | RQIKIWFQNRRM-KWKK-OH |
| | epipodophyllotoxin | 4'-succinimido-propionoyl-C | RQIKIWFQNRRM-KWKK-NH$_2$ |
| | epipodophyllotoxin | 4'-succinimido-propionoyl-CβA | RRMKWKK-NH$_2$ |
| | 4'-demethyl epipodophyllotoxin | 4-succinimido-propionoyl-C | RQIKIWFQNRRM-KWKK-OH |
| | etoposide (G2, G3 and 4') | succinimido-propionoyl-C | RQIKIWFQNRRM-KWKK-OH |
| | roscovotine | succinimido-propionoyl-C | RQIKIWFQNRRM-KWKK-OH |
| | bohemine | βA-succinyl-βA | RQIKIWFQNRRM-KWKK-OH |
| | bohemine | succinimido-propionoyl-C | RQIKIWFQNRRM-KWKK-OH |
| | podophyllotoxin | 4-acetyl-C | RQIKIWFQNRRM-KWKK-OH |
| | podophyllotoxin | 4-acetyl-CβA | RRMKWKK-NH$_2$ |
| | 4'-demethyl epipodophyllotoxin | 4-acetyl-CβA | RRMKWKK-NH$_2$ |
| | 4'-demethyl epipodophyllotoxin | 4-acetyl-C | RQIKIWFQNRRM-KWKK-NH$_2$ |
| | podophyllotoxin | 4-succinimido-propionoyl-GCβA | RRMKWKK-NH$_2$ |
| | camptothecin | 10-O-succinimido-propionoyl-C | RQIKIWFQNRRM-KWKK-NH$_2$ |
| C-term | podophyllotoxin | 4-succinimido-propionoyl-C | RRMKWKK |
| N-term | podophyllotoxin | 4-succinimido-propionoyl-C | |
| N-term | epipodophyllotoxin | 4'-succinimido-propionoyl-C | RRMKWKK |
| C-term | camptothecin | 10-O-succinimido-propionoyl-C | |
| N-term | epipodophyllotoxin | 4'-succinimido-propionoyl-C | RRMKWKK |
| C-term | paclitaxel | 2'-(succinimido)-propionoyl-C | |
| | 4'-methoxy-epipodophyllotoxin | 4-(4"-aminoanilino)succinimido-propionoyl-C | RQIKIWFQNRRM-KWKK-NH$_2$ |
| | 4'-methoxy-epipodophyllotoxin | 4-(4"-aminoanilino)succinimido-propionoyl-CβA | RRMKWKK-NH$_2$ |
| | 4'-demethyl-epipodophyllotoxin | 4-(4"-aminoanilino)succinimido-propionoyl-CβA | RRMKWKK-NH$_2$ |

(RQIKIWFQNRRMKWKK corresponds with SEQ ID No. 25 and RRMKWKK corresponds with SEQ ID No. 26)

The therapeutic effect resulting from the administration of the delivery system may arise from the intact delivery system or any of its dissociated components that include the drug moiety i.e the drug moiety alone or bound to the linker, part of the linker or the linker and part of the carrier. Thus the term "delivery system" has been used herein to have its ordinary meaning i.e that of delivering something such as the drug moiety and additionally to include the system or any portion thereof as being active in its intact state. Thus, the benefits provided by the system discussed above are applicable to the drug and delivery system.

The delivery systems described herein can be macromolecules. Such macromolecules can be selected from any of the delivery systems defined herein.

The delivery vectors may be prepared by any methods known in the art. For example, the pAntp peptide can be assembled using conventional solution- or solid-phase peptide synthesis methods, affording a fully protected precursor with only the terminal amino group in deprotected reactive form. This function can then be reacted directly with a drug moiety or a suitable reactive derivative of a drug moiety. Alternatively, this amino group may be converted into a different functional group suitable for reaction with a drug moiety or a linker. Thus, e.g. reaction of the amino group with succinic anhydride will provide a selectively addressable carboxyl group, while further peptide chain extension with a cysteine derivative will result in a selectively addressable thiol group. Once a suitable selectively addressable functional group has been obtained in the delivery vector precursor, a drug moiety or a derivative thereof may be attached through e.g. amide, ester, or disulphide bond formation. Alternatively, a linker group, e.g. m-maleimidobenzoyl, is introduced by reaction of a linker group precursor with the selectively addressable function of the delivery vector precursor, followed by formation of a covalent bond between the linker group and a drug moiety. Multivalent drug-delivery vector constructs may be obtained, inter alia, by successive extension of the selectively addressable delivery vector precursor with trivalent chemical groups. Thus peptide chain extension with e.g. $N^{\alpha,\epsilon}$-Fmoc-protected Lys derivatives will afford di-, tetra-, and octa-valent construct precursors after one, two, or three coupling/Fmoc-deprotection cycles.

Using these methods, the skilled person will be capable of preparing a wide variety of drug-carrier conjugates utilising a variety of linker moieties. As exemplified below, an appropriate group on the drug moiety may be selected for attachment to the carrier moiety and if desired a linker joined to the drug or carrier moiety, or both prior to their coupling.

The compounds of the present invention may be formulated with a physiologically acceptable diluent or carrier for use as pharmaceuticals for both veterinary, for example in mammals, and particularly human use by a variety of methods. For instance, they may be applied as a composition incorporating a liquid diluent or carrier, for example an aqueous or oily solution, suspension or emulsion, which may often be employed in injectable form for parental administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules (including spansules). Alternative, more specialized types of formulation include liposomes and nanoparticles.

Other types of administration than by injection or through the oral route which are of use in both human and veterinary contexts include the use of suppositores or pessaries.

Another form of pharmaceutical composition is one for buccal or nasal administration or administration to the airways such as alveolar tissue. Other formulations of topical administration include lotions, ointments, creams, gels and sprays.

Compositions may be formulated in unit dosage form, i.e. in the form of discrete portions containing a unit does, or a multiple or sub-unit of a unit dose.

As is described in the Examples below, the delivery system of the present invention provides several advantages over known delivery systems for non-peptide/oligonucleotide delivery systems. These advantages include improved efficacy compared to conventional treatments, improved cellular uptake of the therapeutic agent, improved water solubility, reduction of side effects and cellular bioavailability and decreased occurrence of drug resistance.

The contents of all references, pending patent applications and published patents, cited throughout this application are hereby expressly incorporated by reference.

The invention is further illustrated by the following examples, which should not be construed as further limiting.

EXAMPLES

Abbreviations

Amino acid and peptide nomenclature conforms to IUPAC-IUB rules (*Eur. J. Biochem.* 1984, 138, 9–37). Other abbreviations: AcOH, acetic acid; Boc, tert.-butyloxycarbonyl; Bu$^t$, tert.-butyl; DE MALDI-TOF MS, delayed extraction matrix-assisted laser desorption ionisation time-of-flight mass spectrometry, DIC, 1,3-diisopropylcarbodiimide; DIEA, diisopropylethylamine; DMAP, 4-dimethylaminopyridine; DMEM, Dulbecco's modified Eagle medium; DMF, dimethylformamide; Et$_3$N, triethylamine; EtOAc, ethyl acetate; Et$_2$O, diethyl ether; FCS, foetal calf serum; HOBt, 1-hydroxybenzotriazole; MeCN, acetonitrile; MeOH, methanol; NMR, nuclear magnetic resonance spectroscopy; PE, petroleum ether 40–60° C. boiling fraction; PBS, phosphate-buffered saline; Pmc, 2,2,5,7,8-pentamethylchroman-6-sulfonyl; PyBOP, benzotriazole-1-yl-oxy-tris-pyrrolidino-phosphonium hexafluorophosphate; RP-HPLC, reversed-phase high-performance liquid chromatography; TFA, trifluoroacetic acid; Trt, triphenylmethyl.

General

RP-HPLC was conducted using Vydac 218TP54 (4.5×250 mm) and 218TP 1022 (22×250 mm) columns for analytical and preparative purposes, respectively. Flow rates were 1 mL/min for analytical and 9 mL/min for preparative runs. Gradient elution (constant 25° C.) was performed using increasing amounts of MeCN in water (containing a constant concentration of 0.1% TFA) over 20 min (analytical) or 40 min (preparative). Flash chromatography was carried out as described (W. C. Still, M. Kahn, A. Mitra, *J. Org. Chem.*, 1978, 43, 2923–2925) using Merck silica gel 60, 230–240 mesh. Peptide synthesis was carried out using an ABI 433A Peptide Synthesizer (Perkin-Elmer Applied Biosystems). Amino acid derivatives were from Novabiochem AG, Läufelfingen, Switzerland, except Fmoc-D-Ile-OH, which was from Bachem AG, Bubendorf, Switzerland. Standard synthesis protocols (0.1 mmol or 0.25 mmol scale "FastMoc MonPrevPk" programs) based on the Fmoc-protection strategy (G. B. Fields, R. L. Noble, *Intl. J. Peptide Protein Res.*, 1990, 35, 161) were applied. Peptidyl resins were cleaved and deprotected using the following reagent: 0.75:0.5:0.5:0.25:10 (w/v/v/v/v) phenol, water, thioanisole, 1,2-ethanedithiol, TFA (D. S. King, C. G. Fields, G. B. Fields, *Intl. J. Peptide Protein Res.,* 1990, 36, 255). DE MALDI-TOF MS was performed using a Dynamo (Thermo BioAnalysis, Hemel Hempstead, England) spectrometer. The matrix used was a-cyano-4-hydroxycinnamic acid. The spectrometer was calibrated using authentic peptides with appropriate masses. NMR spectra were recorded on a Brucker DPX300 instrument. Paclitaxel, podophyllotoxin, and 10-hydroxycamptothecin were from Hande Tech Development Co. USA Inc, Houston, Tex., USA. 4'-Demethylepipodophyllotoxin was prepared as described (M. Kuhn, C. Keller-Juslén, A. von Wartburg, *Helv. Chim. Acta*, 1969, 52, 944). Roscovitine was prepared essentially as described (L. Havlicek, J. Hanus, J. Vesely, S. Leclerc, L. Meijer, G. Shaw, M. Strnad, *J. Med. Chem.* 1997, 40, 408). Bohemine (6-(benzylamino)-2-[(3-(hydroxy-propyl)amino]-9-isopropylpurine) was synthesised similarly. Anhydrous DMF, ClCH$_2$CH$_2$Cl, and CH$_2$Cl$_2$, stored over molecular sieve 4A, were used throughout.

Example 1

H-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 25)

The peptide sequence was assembled on Fmoc-Lys(Boc)-[(4-(hydroxymethyl)pheneoxyacetyl)-resin] (ABI 401425; 0.5 mmol/g). The final peptidyl resin (1.37 g, 100%) was washed with Et$_2$O and dried in vacuo. In order to demonstrate the chemical integrity of this intermediate, a small aliquot of peptidyl resin was cleaved and deprotected, followed by analysis of the crude product H-Arg-Gln-Ile-Lys-Ile-Trp-Phe-Gln-Asn-Arg-Arg-Met-Lys-Trp-Lys-Lys-OH (SEQ ID No. 25), which revealed purity of >90% (anal. RP-HPLC) and chemical identity (DE MALDI-TOF MS and quantitative amino acid analysis).

[H-Glu(OBu$^t$)-Gly-bAla]$_4$-Lys$_2$-Lys-bAla-Arg(Pmc)-Gln(Trt)-Ile-Lys(Boc)-Ile-Trp-Phe-Glu(Trt)-Asn(Trt)-Arg(Pmc)-Arg(Pmc)-Met-Lys(Boc)-Trp-Lys(Boc)-Lys(Boc)-resin (SEQ ID No. 28)

The above peptidyl resin (137 mg, 25 μmol) was acylated with Fmoc-βAla-OH (47 mg, 0.15 mmol), PyBOP (78 mg, 0.15 mmol), HOBt (20 mg, 0.15 mmol) and DIEA (39 μL, 0.225 mmol) in DMF (2 mL) during 2 h. It was then Fmoc-deprotected with 20% piperidine in DMF for 20 min and washed extensively with DMF. The product was further extended by two successive acylation and deprotection cycles using Fmoc-Lys(Fmoc)-OH (0.15 mmol in first cycle; 0.3 mmol in second cycle) using similar coupling and deprotection steps. This was followed by further chain extension with Fmoc-Gly-OH (0.6 mmol) and Fmoc-Glu(OBu$^t$)-OH (0.6 mmol), again using similar acylation and Fmoc-deprotection conditions. The product was Fmoc-deprotected and washed extensively with DMF, CH$_2$Cl$_2$ and Et$_2$O, followed by drying in vacuo. In order to demonstrate chemical integrity of this intermediate, a small aliquot of peptidyl resin was cleaved and side-chain deprotected, followed by analysis of the crude product [H-Glu-Gly-βAla]$_4$-Lys$_2$-Lys-βAla-Arg-Gln-Ile-Lys-Ile-Trp-Phe-Gln-Asn-Arg-Arg-Met-Lys-Trp-Lys-Lys-OH (SEQ ID No. 28), which revealed purity (>89%; RP-HPLC, 15–25% MeCN gradient, $t_R$ =17.7 min, λ=200–300 nm) and identity (DE MALDI-TOF MS: [M+H]$^+$=3732, C$_{165}$H$_{269}$N$_{53}$O$_{44}$S=3731.30).

{[4[N-(2,4-diamino-6-pteridinyl-methyl)-N-methylamino]benzoyl]-Glu(OBu$^t$)-Gly-βAla}$_4$-Lys$_2$-Lys-βAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 28)

The above peptidyl resin (76 mg, 25 μmol) was reacted overnight at room temperature with 4[N-(2,4-diamino-6-pteridinyl-methyl)-N-methylamino]benzoic acid hemihydrochloride dihydrate (76 mg, 0.2 mmol) and PyBOP (104 mg, 0.2 mmol), HOBt (27 mg, 0.2 mmol) and DIEA (70 μL, 0.4 mmol) in DMF (2 mL). The product was washed successively with DMF, CH$_2$Cl$_2$ and Et$_2$O and dried in vacuo to afford the title compound (85 mg orange peptidyl resin).

{[4[N-(2,4-Diamino-6-pteridinyl-methyl)-N-methylamino]benzoyl]-Glu-Gly-βAla}$_4$-Lys$_2$-Lys-βAla-Arg-Gln-Ile-Lys-Ile-Trp-Phe-Gln-Asn-Arg-Arg-Met-Lys-Trp-Lys-Lys-OH (SEQ ID No. 28)

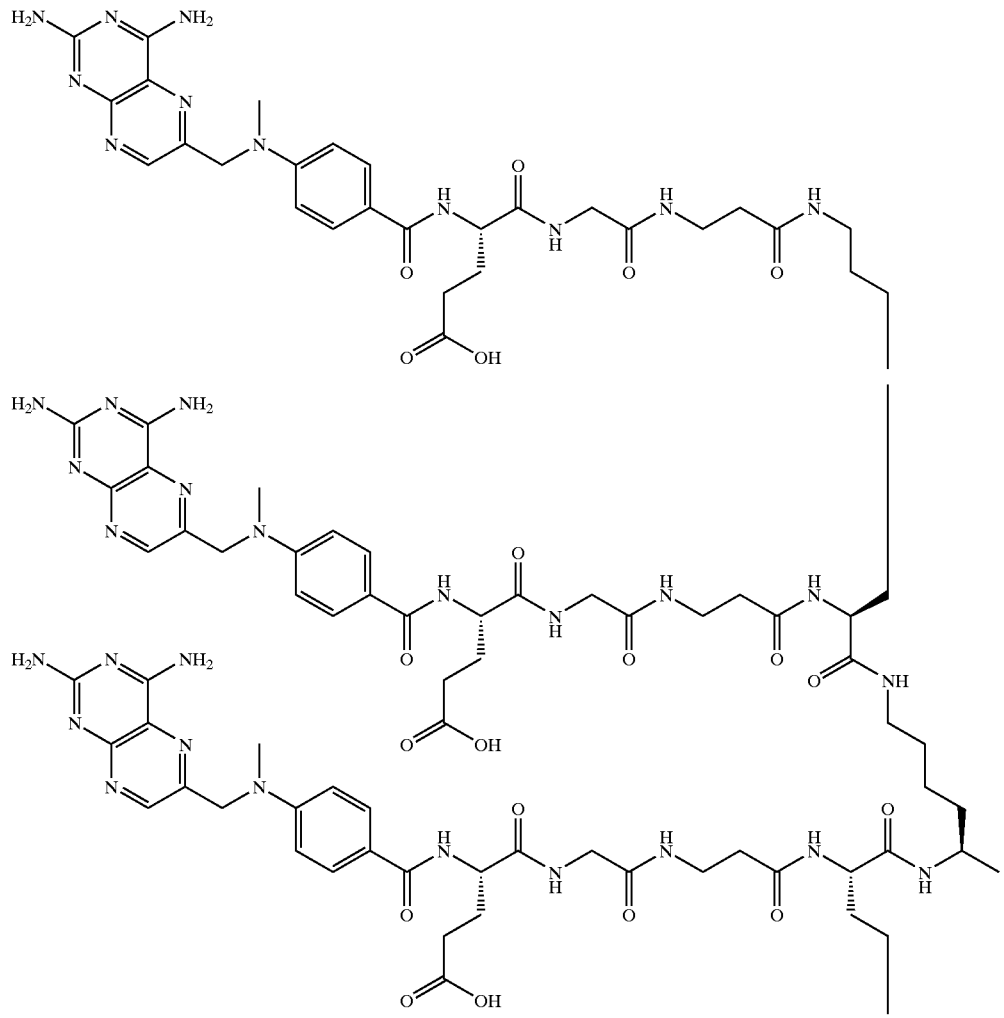

-continued

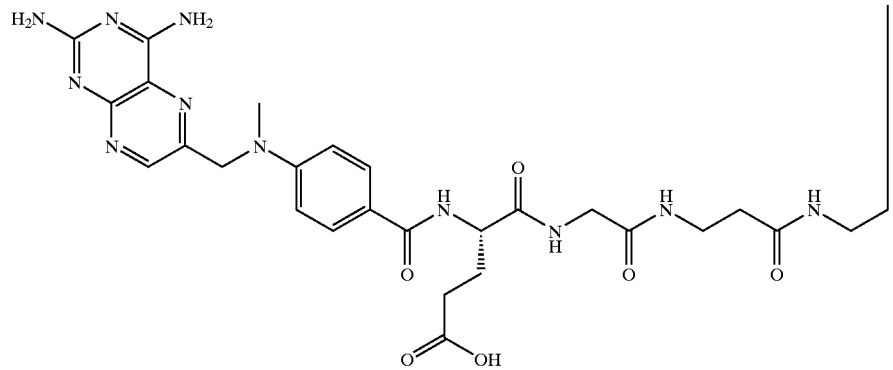

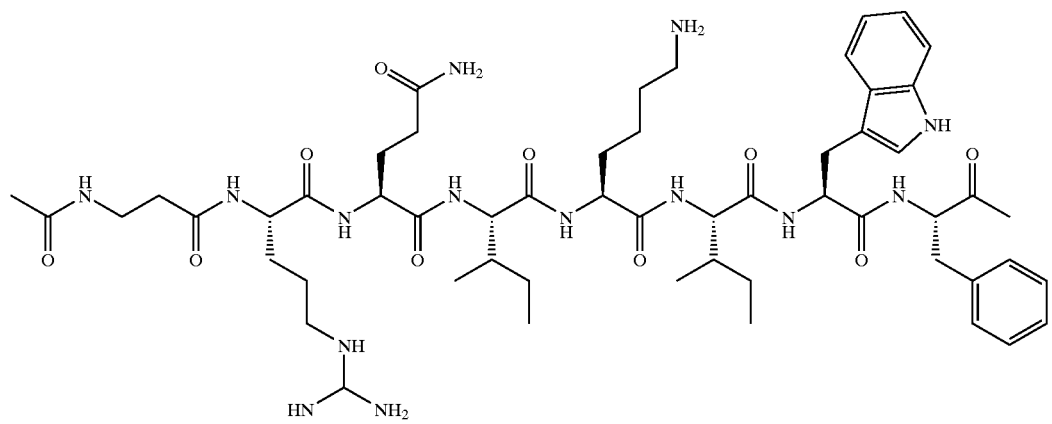

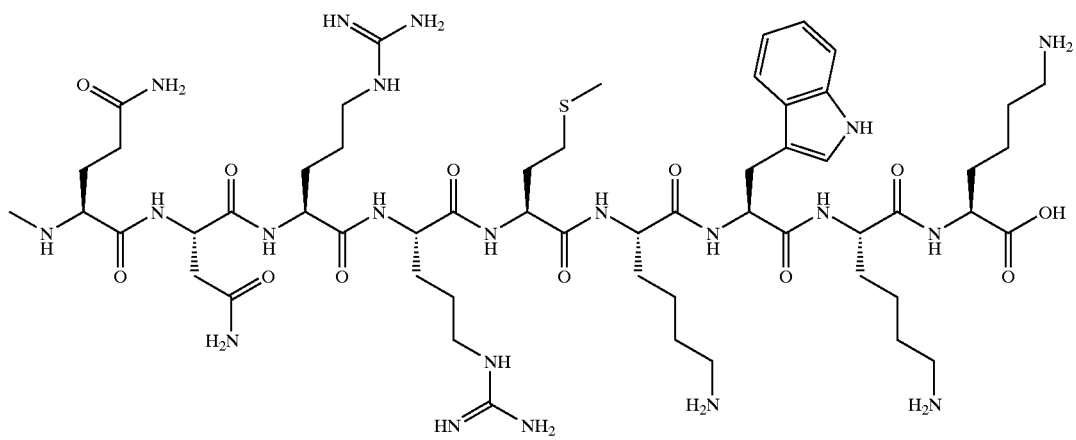

The above product was cleaved and deprotected (12 mL cleavage reagent, 1.5 h). Resin residue was then filtered off and washed on a sinter with small aliquots of neat TPA. The combined filtrate and washings were treated with Et$_2$O (100 mL) and cooled. The precipitated product was collected by centrifugation and the ethereal supernatant was decanted. The product was washed three more times with Et$_2$O in a similar fashion. The final crude product was dried in vacuo (61 mg orange powder). This material was redissolved in 0.1% aq TFA (4 mL) and filtered. The resulting solution was applied (two separate runs) to a preparative RP-HPLC column (17.5–27.5% MeCN gradient runs). Peak fractions were collected, monitored (analytical RP-HPLC) and pooled as appropriate. After vacuum centrifugation, pure title compound (13.5 mg) was obtained. Anal. RP-HPLC: $t_R$=17.8 (17.5–27.5% MeCN gradient; purity>99%, f=200–300 nm). DE MALDI-TOF MS: $[M+H]^+$=4962 ($C_{225}H_{321}N_{81}O_{48}S$= 4960.54).

Example 2

H-Cys-Arg-Gln-Ile-Lys-Ile-Trp-Phe-Gln-Asn-Arg-Arg-Met-Lys-Trp-Lys-Lys-OH (SEQ ID) No. 17)

H-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 1) (see example 1; 411 mg, 75 μmol) was acylated with Fmoc-Cys(Trt)-OH (264 mg, 0.45 mmol), PyBOP (234 mg, 0.45 mmol), HOBt (61 mg, 0.45 mmol) and DIEA (0.12 ml., 0.675 mmol) in DMF (3 mL) during 3 h. The resulting peptidyl resin was washed with DMF (3×5 min, 25 mL each), drained and treated with 20% piperidine in DMF during 20 min. After filtration of the reagent, the product H-Cys(Trt)-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 27) was washed successively with DMF, $CH_2Cl_2$ and $Et_2O$, before being dried in vacuo. This product was cleaved/deprotected (2 h). Resin residue was then filtered off and washed on a sinter with small aliquots of neat TFA. The combined filtrate and washings were treated with $Et_2O$ (100 mL) and cooled. The precipitated product was collected by centrifugation and the ethereal supernatant was decanted. The product was washed three more times with $Et_2O$ in a similar fashion. The final crude product was dried in vacuo (238 mg). An aliquot (119 mg) of this material was redissolved in 0.1% aq TFA (2 mL) and filtered. The resulting solution was purified by preparative RP-HPLC (17.5–27.5% MeCN gradient). Peak fractions were collected, monitored (analytical RP-HPLC) and pooled as appropriate. After vacuum centrifugation, pure title compound (60.9 mg) was obtained. Anal. RP-HPLC: $t_R$=15.8 min (17.5–27.5% MeCN gradient; purity>99%, λ=214 nm). DE MALDI-TOF MS: $[M+H]^+$=2351 ($C_{107}H_{173}N_{35}O_{21}S_2$=2349.87).

N-[3-(Maleimido)benzoyl]doxorubicin

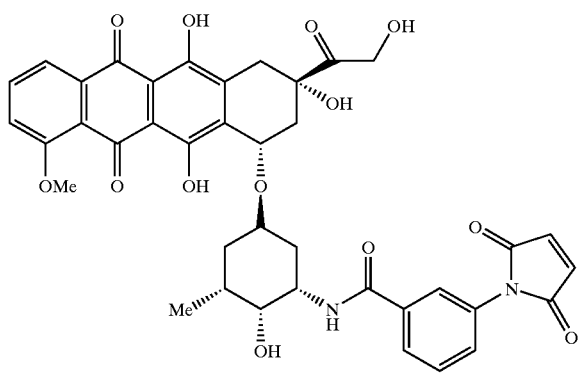

Doxorubicin hydrochloride (5.9 mg, 10 μmol) was dissolved in water (1 mL) and DMF (0.5 mL). Buffer (0.1 M aq phosphate, pH 7.2; 0.5 mL) was added with stirring. To the resulting suspension 3-maleimidobenzoic acid N-hydroxysuccinimide ester (12.9 mg, 40 μmol) in DMF (1 mL) was added dropwise. The red-coloured reaction mixture cleared temporarily and after ca. 10 min precipitation was observed. Reaction progress was monitored by anal. RP-HPLC and after 2 h all doxorubicin had reacted. The mixture was then diluted with $H_2O$ (1.5 mL), cooled to 4° C. and centrifuged. The supernatant was decanted. The residual pellet was redissolved in DMF (1 mL) and diluted with 0.1% aq TFA (2 mL). This solution was applied to a solid-phase extraction cartridge (Merck LiChrolut RP-18, 500 mg; preconditioned successively with MeOH and 0.1% aq TFA); the cartridge was washed with 0.1% aq TFA (4 mL) and eluted with 6:4 MeCN/$H_2O$ (containing 0.1% TFA) in two fractions (2×4 mL). The first fraction contained the title compound and was used directly in the next step.

N-{3-[3-(H-Cys-Arg-Gln-Ile-Lys-Ile-Trp-Phe-Gln-Asn-Arg-Arg-Met-Lys-Trp-Lys-Lys-OH) succinimido]benzoyl}doxorubicin (SEQ ID No. 27)

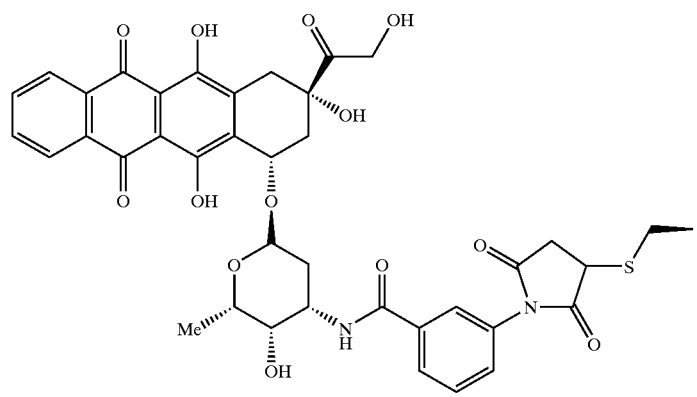

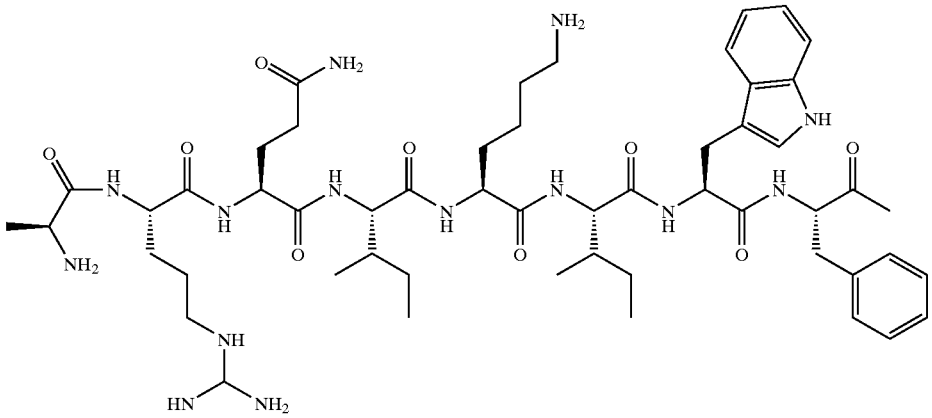

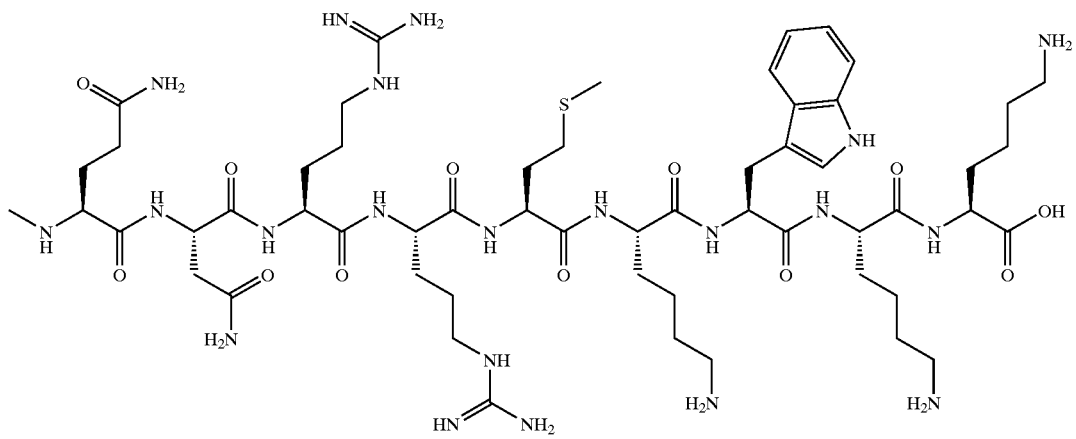

The above N-[3-(maleimido)benzoyl]doxorubicin solution was diluted with DMF (1 mL) and Et$_3$N (50 μL) was added. The solution turned dark brown. H-Cys-Arg-Gln-Ile-Lys-Ile-Trp-Phe-Gln-Asn-Arg-Arg-Met-Lys-Trp-Lys-Lys-OH (SEQ ID No. 27) (5 mg), dissolved in DMF (1 mL) was then added. The mixture was stirred and the brown colour was observed to discharge, leaving a light red solution. The reaction was monitored by anal. RP-HPLC. After 1.5 h, all 3-(maleimido-benzoyl)doxorubicin had reacted. The solution was acidified with AcOH (0.5 mL), diluted with water (3 mL) and applied to a pre-conditioned solid-phase extraction cartridge (Merck LiChrolut RP-18, 500 mg). The cartridge was washed with 0.1% aq TFA (6 mL) and eluted (6 mL of 6:4 MeCN/water (containing 0.1% TFA)). The eluate was dried by vacuum centrifugation. The residue was redissolved in 0.1% aq TFA (2 mL), filtered and purified by preparative RP-HPLC (20–40% MeCN gradient). Peak fractions were collected, monitored (analytical RP-HPLC) and pooled as appropriate. After vacuum centrifugation, pure title compound (1.2 mg) was obtained. Anal. RP-HPLC: $t_R$=15.6 & 15.8 min (partly resolved thioether diastereomers) (0–60% MeCN gradient; purity>95%, λ=200–300 nm). DE MALDI-TOF MS: [M+H]$^+$=3094, [M+2H]$^{2+}$=1548 (C$_{145}$H$_{207}$N$_{37}$O$_{35}$S$_2$=3092.56).

Example 3

H-Cys-D-Lys-D-Lys-D-Trp-D-Lys-D-Met-D-Arg-D-Arg-D-Asn-D-Gln-D-Phe-D-Trp-D-Ile-D-Lys-D-Ile-D-Gln-D-Arg-NH$_2$ (SEQ ID No. 29)

Starting from Rink Amide AM resin (0.64 mmol/g; Novabiochem), the sequence H-Cys(Trt)-D-Lys(Boc)-D-Lys(Boc)-D-Trp-D-Lys(Boc)-D-Met-D-Arg(Pmc)-D-Arg(Pmc)-D-Asn (Trt)-D-Gln(Trt)-D-Phe-D-Trp-D-Ile-D-Lys(Boc)-D-Ile-D-Gln(Trt)-D-Arg(Pmc)-resin (SEQ ID No. 29) was assembled in quantitative yield. The peptidyl resin was cleaved/deprotected (10 mL cleavage reagent/g; 2 h) and the crude peptide was isolated by precipitation from Et$_2$O, centrifugation/decantation and drying. An aliquot (100 mg) of this material was redissolved in 0.1% aq TEA (2 mL) and filtered. The resulting solution was purified by preparative RP-HPLC (17.5–27.5% MeCN gradient) to afford, after vacuum centrifugation, pure title compound (36.4 mg). Anal. RP-HPLC: t$_R$=16.3 min (17.5–27.5% MeCN gradient; purity>99%, λ=214 nm). DE MALDI-TOF MS: [M+H]$^+$= 2350.1 (C$_{107}$H$_{174}$N$_{36}$O$_{20}$S$_2$=2348.89).

N-{3-[3-(H-Cys-D-Lys-D-Lys-D-Trp-D-Lys-D-Met-D-Arg-D-Arg-D-Asn-D-Gln-D-Phe-D-Trp-D-Ile-D-Lys-D-Ile-D-Gln-D-Arg-NH$_2$)succinimido]benzoyl}doxorubicin (SEQ ID No. 29)

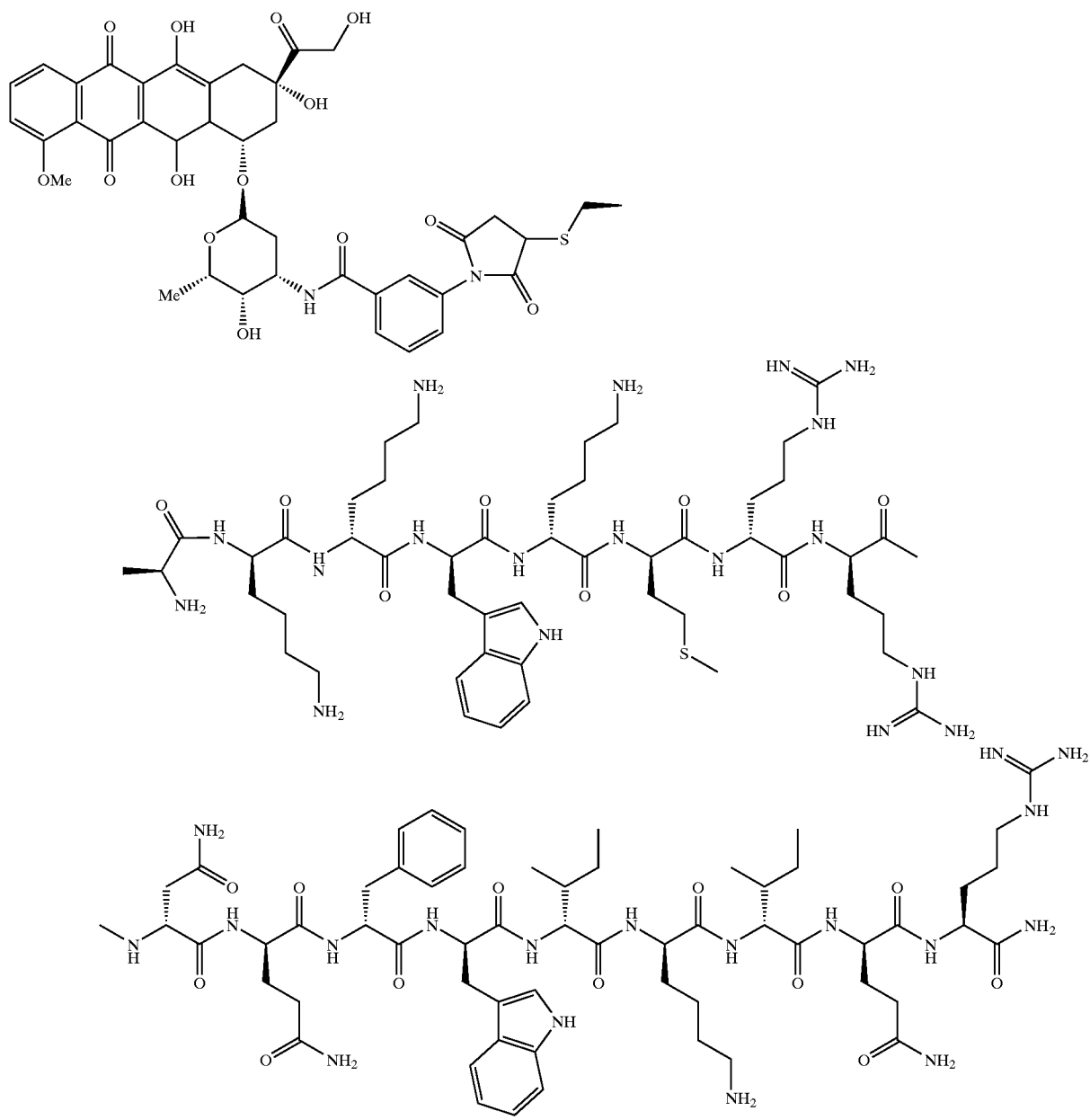

N-[3-(Maleimido)benzoyl]doxorubicin (12.6 mg, 17 μmol) and H-Cys-D-Lys-D-Lys-D-Trp-D-Lys-D-Met-D-Arg-D-Arg-D-Asn-D-Gln-D-Phe-D-Trp-D-Ile-D-Lys-D-Ile-D-Gln-D-Arg-NH$_2$ (SEQ ID No. 29) (20 mg, 8.5 μmol)

were dissolved in DMF (1 mL) and Et$_3$N (100 μL) was added. The mixture was stirred for 2 h, quenched by addition of AcOH (0.5 mL), diluted with water (0.5 mL) and filtered. The filtrate was purified by preparative RP-HPLC (20–40% MeCN gradient) to afford the pure title compound as a red solid (6.3 mg). Anal. RP-HPLC: $t_R$=16.3 min (0–60% MeCN gradient; purity>95%). DE MALDI-TOF MS: [M+H]$^+$=3092.7, (C$_{145}$H$_{208}$N$_{38}$O$_{34}$S$_2$=3091.57).

Example 4

2'-(Maleimidopropionoyl)paclitaxel

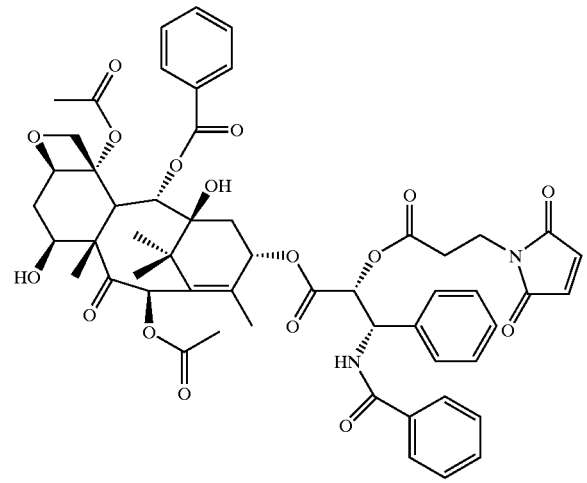

A mixture of paclitaxel (29.2 μmol, 25 mg), 3-maleimidopropionic acid (0.120 mmol, 20.3 mg) and DIC (66 μmol, 10.3 μL) in pyridine (1 mL) was stirred for 1 hr. The solvent was evaporated, the residue was treated with water and extracted with CH$_2$Cl$_2$. The organic phase was washed with water and brine and was dried over MgSO$_4$, The solvent was evaporated to dryness to afford 22.2 mg (76%) colourless solid, which was recrystallised from EtOAc/hexane to provide the pure title compound. $^1$H-NMR (300 MHz, CDCl$_3$) δ: 1.13, 1.22, 1.68, 1.91 (s, each 3H, CH$_3$), 2.23, 2.47 (s, each 3H, Ac—CH$_3$), 2.35 (m, 2H, H6), 2.78 (t, 4H, J=5.40 Hz, CH$_2$), 2.84 (m, 2H, H14), 3.81 (m, 2H, CH$_2$), 3.87 (m, 1H, H3), 4.26 (m, 2H, H20), 4.44 (dd, 1H, J=10.87, 4.25 Hz, H7), 4.98 (d, 1H, J=7.69 Hz, H5), 5.47 (d, 1H, J=3.45 Hz, H2'), 5.68 (d, 1H, J=7.09 Hz, H3'), 6.05 (dd, 1H, J=9.28, 5.86 Hz, H2), 6.28 (s, 1H, H10), 6.18 (t, 1H, J=8.77 Hz, H13), 6.49 (s, 2H, CH=CH), 8.16–7.34 (m, 15H, Ph). $^{13}$C-NMR (75 MHz; CDCl$_3$) δ: 10.01, 15.20, 21.22, 22.54 23.09, 27.18, 32.90, 33.71, 35.90, 43.54, 45.96, 52.86, 58.89, 72.18, 72.53, 74.86, 75.51, 76.02, 79.52, 81.42, 84.89, 126.94, 127.91, 128.74, 128.94, 129.14, 129.45, 129.59, 130.65, 132.39, 133.11, 133.85, 134.09, 134.46, 137.17, 143.25, 167.45, 168.01, 168.10, 169.77, 170.29, 171.10, 171.69, 204.24.

2'-[Succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27)

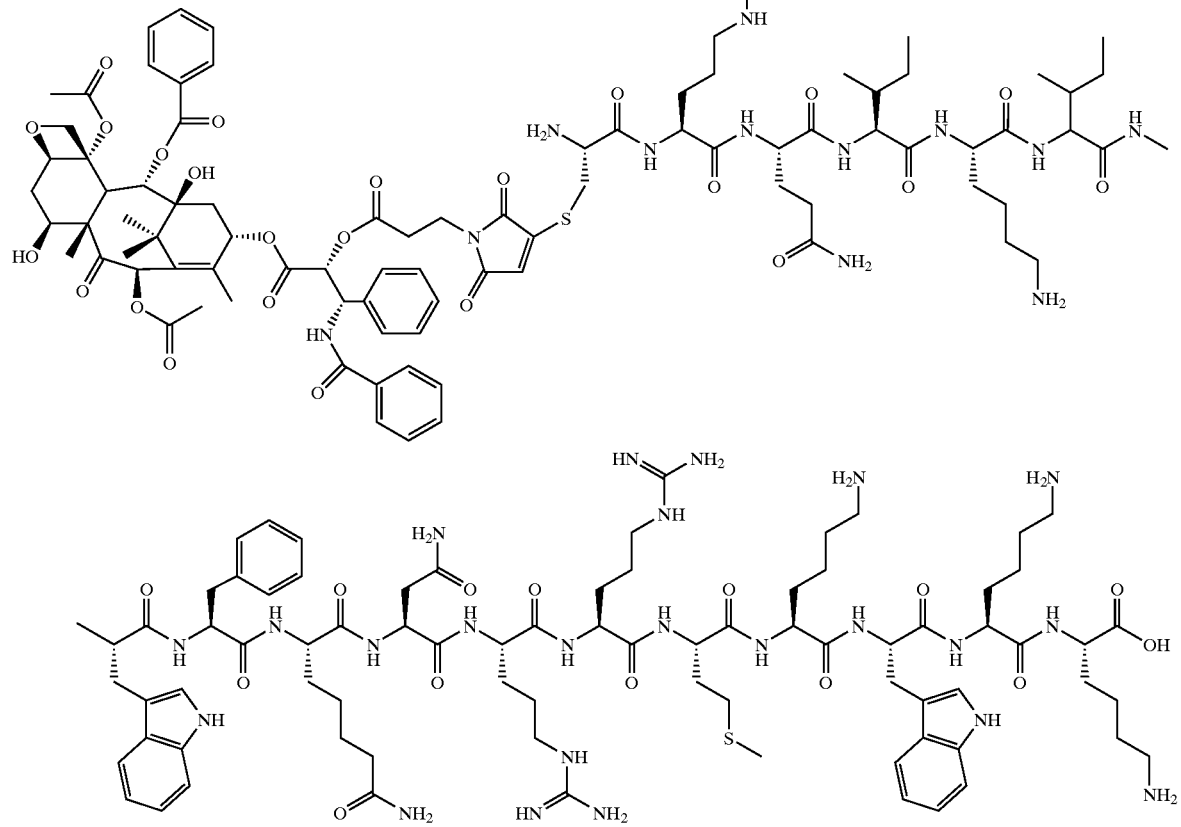

A solution of 2'-(maleimidopropionoyl)paclitaxel (10 μmol, 10.05 mg) and H-Cys-Arg-Gln-Ile-Lys-Ile-Trp-Phe-Gln-Asn-Arg-Arg-Met-Lys-Trp-Lys-Lys-OH (SEQ ID No. 27) (10 μmol, 23.5 mg) in DMF (1 mL) was added Et$_3$N (1.39 μL, 10 μmol). The reaction mixture was stirred for 1 h. It was diluted with 0.1% aq TFA (0.5 mL), filtered and purified by preparative RP-HPLC (10–70% MeCN gradient). Pure title compound (20.5 mg, 62%) was obtained as a colourless solid. Anal. RP-HPLC: $t_R$=17.4 min (0–60% MeCN gradient, purity>97%). DE MALDI-TOF MS: [M+H]$^+$=3355.9 ($C_{161}H_{229}N_{37}O_{38}S_2$=3354.90).

Example 5

4(5)-carboxyfluorescein-βAla-Arg-Gln-Ile-Lys-Ile-Trp-Phe-Gln-Asn-Arg-Arg-Met-Lys-Trp-Lys-Lys-Gly-Cys-Gly-NH$_2$ (SEQ ID No. 18)

The peptide sequence was assembled on Rink Amide AM resin (0.65 mmol/g, 385 mg; Novabiochem) to afford H-βAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Gly-Cys(Trt)-Gly-resin (SEQ ID No. 18) (1.50 g, quant.). An aliquot of this peptidyl resin (450 mg, 75 μmol) was stirred for 18 h in the dark with a solution of 4(5)-carboxyfluorescein (113 mg, 0.3 mmol), PyBOP (156 mg, 0.3 mmol), HOBt (41 mg, 0.3 mmol) and DIEA (78 μL, 0.45 mmol) in DMF (4 mL). Resin was collected on a sinter and washed successively with DMF, CH$_2$Cl$_2$ and Et$_2$O. After drying, the resin was treated with cleavage reagent (5 mL, 1.5 h) in the dark. The product was isolated by precipitation with Et$_2$O and centrifugation (237 mg yellow powder). An aliquot (100 mg) was purified by preparative RP-HPLC (22.5–32.5% MeCN gradient) to afford the pure title compound (36.9 mg) as a yellow film after isolation by vacuum centrifugation. Anal. RP-HPLC: $t_R$=18.6 & 19.2 min (resolved 4- and 5-carboxyfluorescein geometric isomers) (22.5–32.5% MeCN gradient, purity>99%, λ=214 nm). DE MALDI-TOF MS: [M+H]$^+$=2892.2, [M+Na]$^+$=2913.7 ($C_{135}H_{195}N_{39}O_{29}S_2$=2892.4).

2'-[Succinimidopropionoyl-(4(5)-carboxyfluorescein-βAla-Arg-Gln-Ile-Lys-Ile-Trp-Phe-Gln-Asn-Arg-Arg-Met-Lys-Trp-Lys-Lys-Gly-Cys-Gly-NH$_2$)]paclitaxel (SEQ ID No. 18)

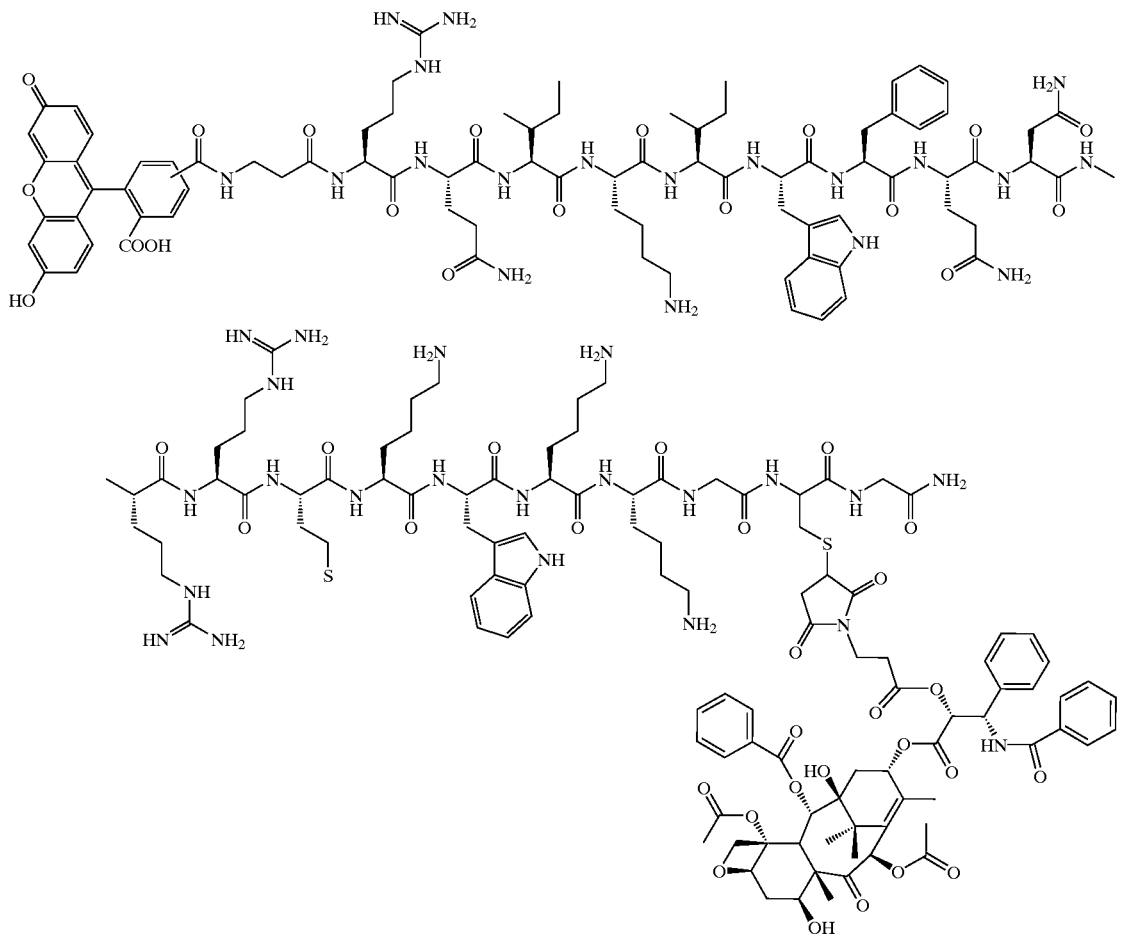

To a solution of 2'-(maleimidopropionoyl)paclitaxel (12.3 μmol, 12.4 mg) and 4(5)-carboxyfluorescein-bAla-Arg-Gln-Ile-Lys-Ile-Trp-Phe-Gln-Asn-Arg-Arg-Met-Lys-Trp-Lys-Lys-Gly-Cys-Gly-NH$_2$ (SEQ ID No. 18) (4.3 μmol, 12.5 mg) in DMF (1 mL) was added Et$_3$N (1.8 μL). The reaction mixture was stirred for 1 h. It was diluted with 0.1% aq TFA (0.5 mL), filtered and purified by RP-HPLC (10–70% MeCN gradient) to afford pure title compound (3.2 mg) as a colourless solid. Anal. RP-HPLC: $t_R$=21.6 min (0–60% MeCN gradient, purity>97%). DE MALDI-TOF MS: $[M+H]^+$=3397.35 ($C_{189}H_{251}N_{41}O_{46}S_2$=3397.40).

Example 6

H-Cys-Arg-Gln-Ile-Lys-Ile-Trp-Phe-Gln-Asn-Arg-Arg-Met-Lys-Trp-Lys-Lys-NH$_2$ (SEQ ID No. 27)

Starting from Rink Amide AM resin (0.69 mmol/g, Novabiochem), H-Cys(Trt)-Arg(Pmc)-Gln(Trt)-Ile-Lys (Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 27) was assembled. After deprotection (1.5 h), the crude peptide was obtained by precipitation from Et$_2$O, centrifugation/decantation, and drying. Aliquots (total 472 mg) were purified by preparative RP-HPLC (16.5–26.5% MeCN gradient) to afford the pure title compound (109.9 mg). Anal. RP-HPLC: $t_R$=16.0 min (17.5–27.5% MeCN gradient, purity>99%, λ=214 nm). DE MALDI-TOF MS: $[M+H]^+$=2349.3 ($C_{107}H_{174}N_{36}O_{20}S_2$=2348.89).

2'-[Succinimidopropionoyl-(H-Cys-Arg-Gln-Ile-Lys-Ile-Trp-Phe-Gln-Asn-Arg-Arg-Met-Lys-Trp-Lys-Lys-NH$_2$)]paclitaxel (SEQ ID No. 27)

(9 μmol, 20.9 mg) in DMF (1 mL) was added Et$_3$N (1.8 μL). The mixture was stirred for 1 h, diluted with 0.1% aq TFA (0.5 mL), filtered and purified by preparative RP-HPLC (10–70% MeCN gradient). The pure title compound (15.9 mg, 53%) was obtained as a colourless solid. Anal. RP-HPLC: $t_R$=18.5 min (0–60% MeCN gradient, purity>97%). DE MALDI-TOF MS: $[M+H]^+$=3353.6 ($C_{161}H_{230}N_{38}O_{37}S_2$=3353.91).

Example 7

H-Cys-βAla-Arg-Arg-Met-Lys-Trp-Lys-Lys-NH$_2$ (SEQ ID No. 19)

Starting from Rink Amide AM resin (0.69 mmol/g, Novabiochem), H-Cys(Trt)-βAla-Arg(Pmc)-Arg(Pmc)-Met-Lys(Boc)-Trp-Lys(Boc)-Lys(Boc)-resin (SEQ ID No. 19) was assembled. After deprotection (1.5 h), the crude peptide was obtained by precipitation from Et$_2$O, centrifugation/decantation, and drying. Aliquots (total 246 mg) were purified by preparative RP-HPLC (6.5–16.5% MeCN gradient) to afford the pure title compound (106.4 mg). Anal. RP-HPLC: $t_R$=15.8 min (6.5–16.5% MeCN gradient, purity>95%, λ=214 nm). DE MALDI-TOF MS: $[M+H]^+$=1205.4 ($C_{52}H_{92}N_{20}O_9S_2$=1205.55).

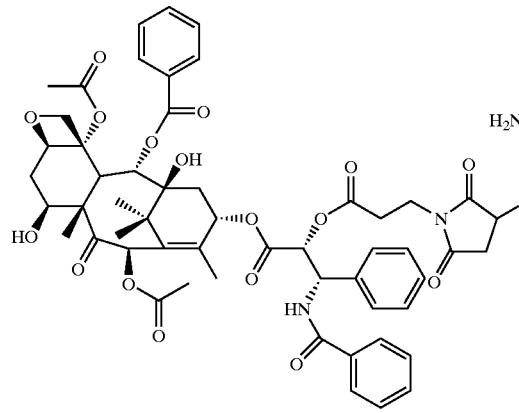
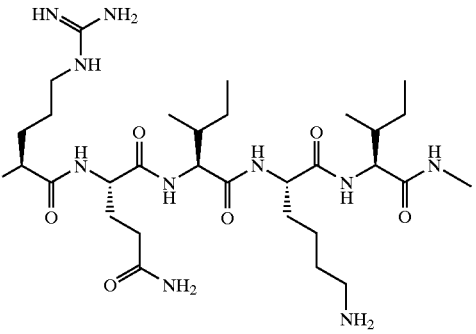
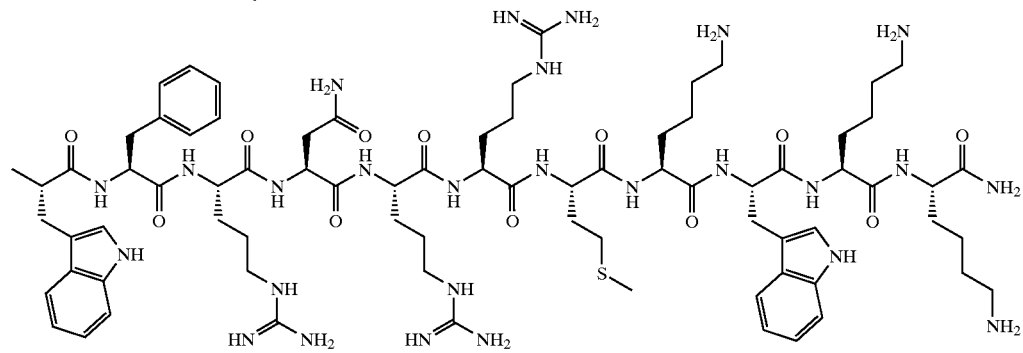

To a solution of 2'-(maleimidopropionoyl)paclitaxel (9 μmol, 9 mg) and H-Cys-Arg-Gln-Ile-Lys-Ile-Trp-Phe-Gln-Asn-Arg-Arg-Met-Lys-Trp-Lys-Lys-NH$_2$ (SEQ ID No. 27)

2'-[Succinimidopropionoyl-(H-Cys-bAla-Arg-Arg-Met-Lys-Trp-Lys-Lys-NH$_2$)]paclitaxel (SEQ ID No. 19)

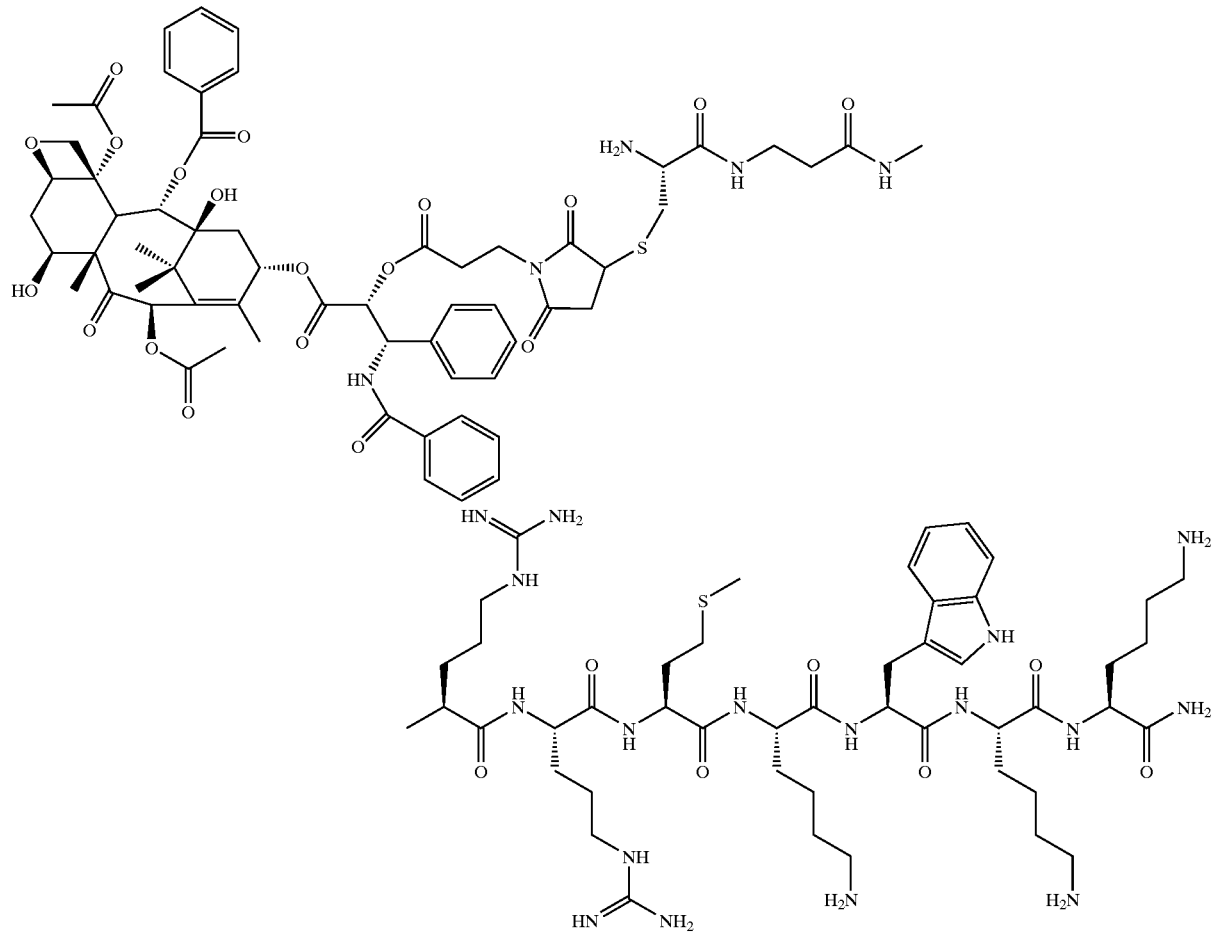

To a solution of 2'-(maleimidopropionoyl)paclitaxel (17 μmol, 17.4 mg) and H-Cys-βAla-Arg-Arg-Met-Lys-Trp-Lys-Lys-NH$_2$ (SEQ ID No. 19) (15 μmol, 18.1 mg) in DMF (1 mL) was added Et$_3$N (2.0 μL). The mixture was stirred for 1 h, filtered and purified by preparative RP-HPLC (10–70% MeCN gradient). The pure title compound (9.4 mg) was obtained as a colourless solid. Anal. RP-HPLC: $t_R$=17.2 min (0–60% MeCN gradient, purity>97%). DE MALDI-TOF MS: [M+H]$^+$=2211.7 (C$_{106}$H$_{148}$N$_{22}$O$_{26}$S$_2$=2210.57.

Example 8

2'-Methoxyacetyl-7-maleimidopropionoyl)paclitaxel

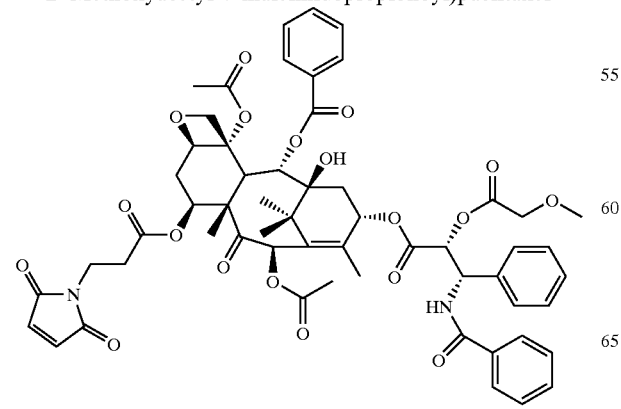

A solution of paclitaxel (29 μmol, 25 mg), methoxyacetic acid N-hydroxysuccinimidyl ester (0.176 mmol, 32.8 mg) and of DIEA (0.176 mmol, 30.6 μL) in $CH_2Cl_2$ (1 mL) was heated under reflux for 4 h. Methanol (1.6 μL) was added. After stirring for 10 min, the reaction mixture was washed with 0.1 M aq HCl., water, brine, and was dried on $MgSO_4$. The solvent was evaporated in vacuo to afford 2'-(methoxyacetyl)paclitaxel as a white solid (24.8 mg, 91%). This material (30 μmol), together with 3-maleimidopropionic acid, DIC (14.1 μL, 90 mmol) and DMAP (20 μmol, 2.6 mg) was dissolved in $CH_2Cl_2$ (2.5 mL) and the mixture was stirred for 40 min. It was washed with water and dried on $MgSO_4$. The solvent was removed in vacuo to afford a light-yellow solid. This was redissolved in DMF/MeOH, filtered and purified by preparative RP-HPLC (20–70% MeCN gradient) to afford the pure title compounds as a colourless solid (24.4 mg, 76%). Anal. RP-HPLC: $t_R$=21.8 min (10–70% MeCN gradient, purity>98%). $^1$H-NMR (300 MHz, $CDCl_3$) δ: 1.15, 1.20, 1.79, 1.96 (s, each 3H, $CH_3$x4), 2.20, 2.45 (s, each 3H, Ac—$CH_3$x2), 2.34 (m, 2H, H6), 2.63 (m, 4H, H14, $CH_2$), 3.40 (s, 3H, $OCH_3$), 3.73–3.94 (m, 3H, $CH_2$, H3), 4.16–4.21 (m, 2H, H20), 4.97 (d, 1H, J=8.06 Hz, H5), 5.54–5.69 (m, 3H, H7, H2, H3'), 5.98 (m, 1H, H2'), 6.22 (s, 1H, H10), 6.24 (m, 1H, H13), 6.68 (s, 2H, CH=CH), 7.12–8.13 (m, 15H, Ph).

2'-Methoxyacetyl-7-[succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID) No. 27)

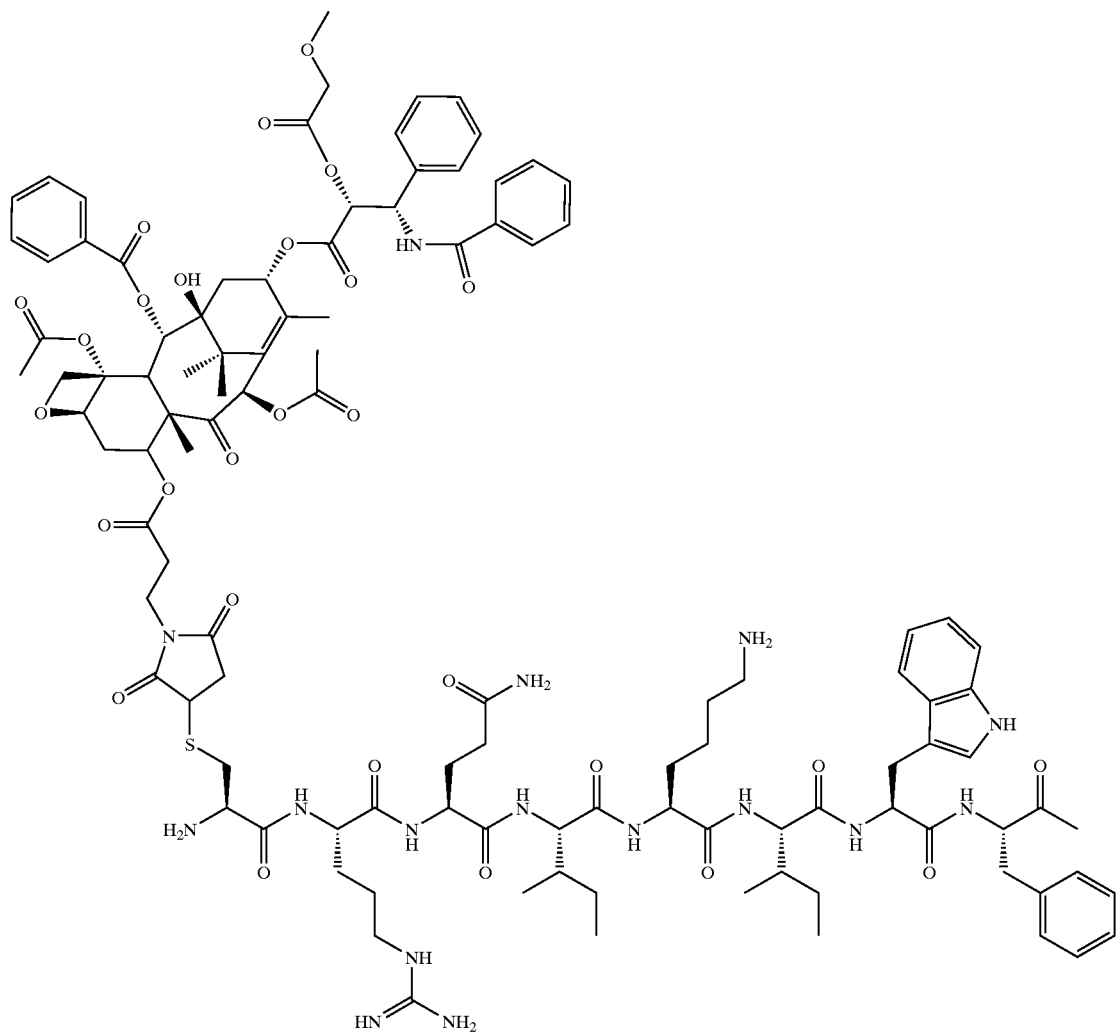

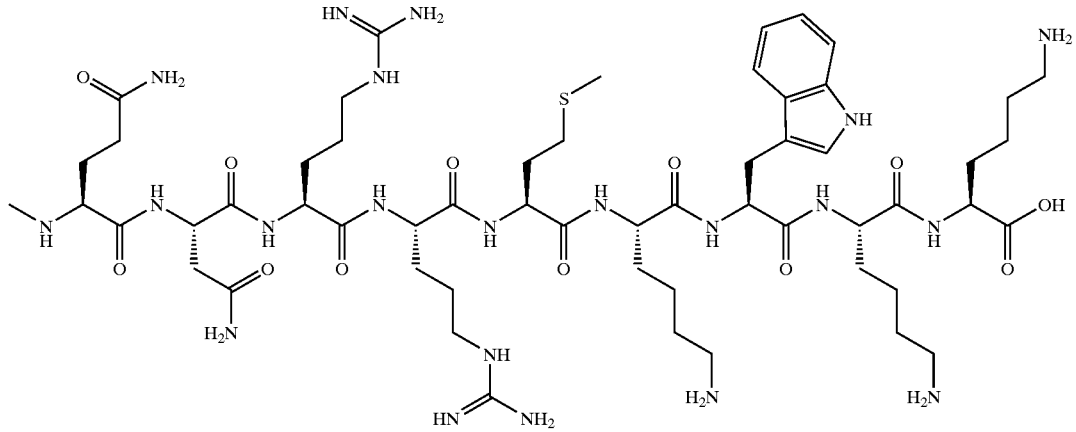

To a solution of 2'-methoxyacetyl-7-(maleimidopropionoyl)paclitaxel (11 μmol, 12.3 mg) and H-Cys-Arg-Gln-Ile-Lys-Ile-Trp-Phe-Gln-Asn-Arg-Arg-Met-Lys-Trp-Lys-Lys-OH (SEQ ID No. 27) (11 μmol, 26.8 mg) in DMF (1 mL) was added Et$_3$N (1.58 μL, 11 μmol). The mixture was stirred for 2 h, diluted with 0.1% aq TFA (0.5 mL) and purified by preparative RP-HPLC (10–70% MeCN gradient). The pure title compound was obtained as a colourless solid (15.5 mg, 40%). Anal. RP-HPLC: t$_R$=15.1 min (10–70% MeCN gradient, purity>97%). DE MALDI-TOF MS: [M+H]$^+$=3425.99 (C$_{164}$H$_{233}$N$_{37}$O$_{40}$S$_2$=3424.96).

7-[Succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27)

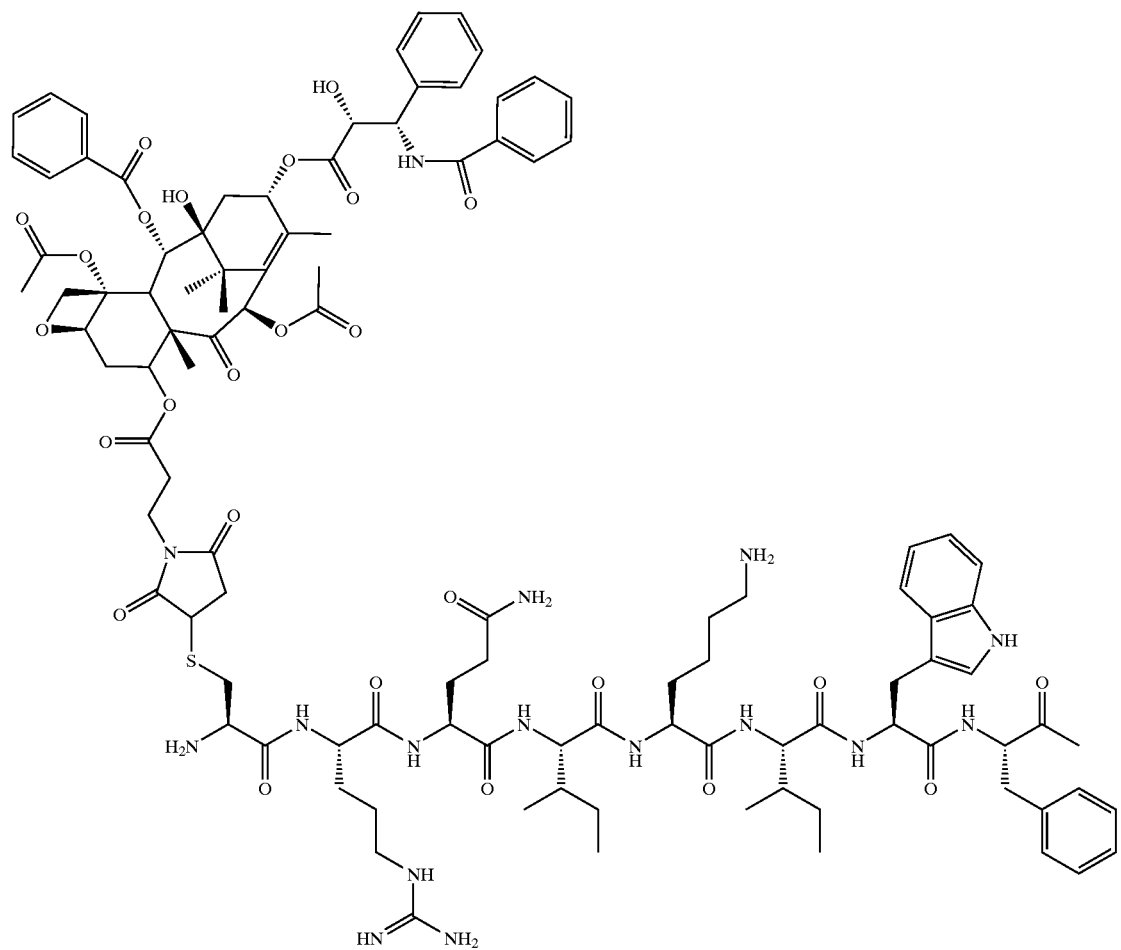

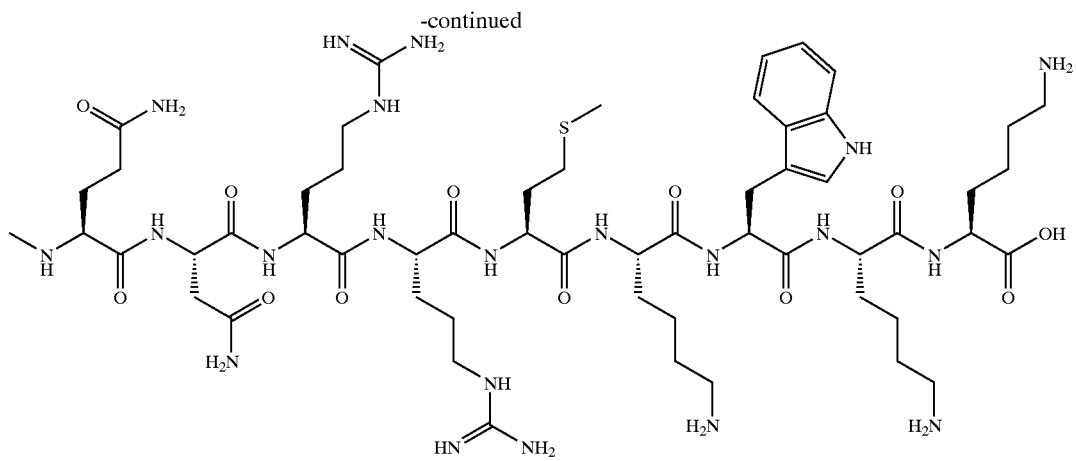

To 2'-methoxyacetyl-7-[succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27) (35 μmol, 11.9 mg) in MeOH (1 mL) was added ethanolamine (0.21 μL). The mixture was stirred for 1 h, diluted with 0.1% aq TFA (0.5 mL), filtered and purified by preparative RP-HPLC (10–70% MeCN gradient). The pure title compound was obtained as a colourless solid (5.6 mg, 48%). Anal. RP-HPLC: $t_R$=14.3 min (10–70% MeCN gradient, purity>97%). DE MALDI-TOF MS: $[M+H]^+$=3355.7, ($C_{161}H_{229}N_{37}O_{38}S_2$=3354.90).

Example 9

2'-(p-Methoxytrityl)paclitaxel

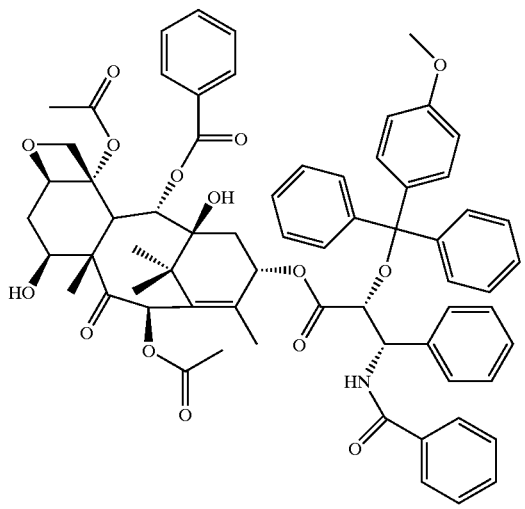

A solution of paclitaxel (0.632 mmol, 540 mg) and p-methoxytrityl chloride (10 mol eq) in $CH_2Cl_2$ (10 mL) was treated with pyridine (1.3 mL) under $N_2$. After stirring of the mixture for 22 h, solvents were evaporated in vacuo. The residue was redissolved in EtOAc, washed with water and brine and was dried on $MgSO_4$. The solvent was evaporated to afford a light yellow solid which was purified by flash chromatography (8:9 EtOAc/PE) to afford the pure title compound in a quantitative yield. Recrystallisation from EtOAc/$CH_2Cl_2$ gave light yellow crystals. $^1$H-NMR (300 MHz, $CDCl_3$) δ: 1.08, 1.15, 1.51, 1.65, (s, each 3H, $CH_3$x4), 1.90 (m, 1H, H6), 2.25, 2.29 (s, each 3H, Ac—$CH_3$x2), 2.55 (m, 1H, H6), 2.54 (m, 2H, H14), 3.75 (s, 3H, $OCH_3$), 3.66 (m, 1H, H3), 4.20 (m, 2H, H20), 4.40 (m, 1H, H7), 4.62 (m, 1H, H2'), 4.94 (d, 1H, J=8.06 Hz, H5), 5.61 (m, 1H, H2), 5.70 (m, 2H, H13, H3'), 6.19 (s, 1H, H10), 6.72–8.08 (m, 29H, Ph).

2'-(p-Methoxytrityl)-7-(maleimidopropionoyl) paclitaxel

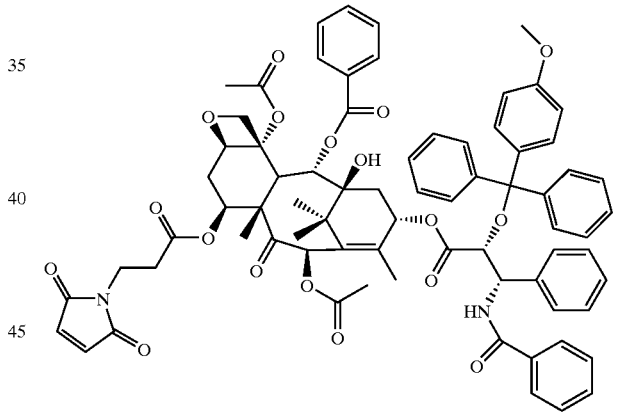

2'-(p-Methoxytrityl)paclitaxel (35 μmol, 38.4 mg) and pyridine (125 μL) were dissolved in $CH_2Cl_2$ (2 mL). A solution of 3-maleimidopropionic acid (1.48 mmol, 250.5 mg), DIC (0.80 mmol, 101.5 mg) and DMAP (10 mg) in $CH_2Cl_2$ (2 mL) was added and the mixture was stirred for 1 h. The solvent was evaporated and the residue was partitioned between water and $CH_2Cl_2$. The organic layer was washed with water, brine and was dried on $MgSO_4$. The solvent was removed and the residue was purified by Chromatotron® centrifugal thin-layer chromatography (5:4 EtOAc/PE). Recrystallisation from EtOAc/$CH_2Cl_2$ afforded the title compound as a colourless solid (22 mg, 49%). $^1$H-NMR (300 MHz, $CDCl_3$) δ: 1.18, 1.12, 1.76, 1.96 (s, each 3H, $CH_3$x4), 2.17, 2.26 (s, each 3H, Ac—$CH_3$x2), 2.10, 2.34 (m, 2H, H6), 2.62 (m, 4H, H14, $CH_2$-Mim), 3.75 (s, 3H, $OCH_3$), 3.73–3.79 (m, 3H, $CH_2$-Mim, H3), 4.06 (m, 2H, H20), 4.61 (d, 1H, J=3.47 Hz, H2'), 4.76 (d, 1H, J=9.52 Hz, H5), 5.53 (m, 1H, H7), 5.60 (d, 1H, J=6.98 Hz, H3'), 5.71 (m, 1H, H2), 6.14 (s, 1H, H10), 6.60 (m, 3H, H13, CH=CH), 6.75–7.79 (m, 29H, Ph).

7-(Maleimidopropionoyl)paclitaxel

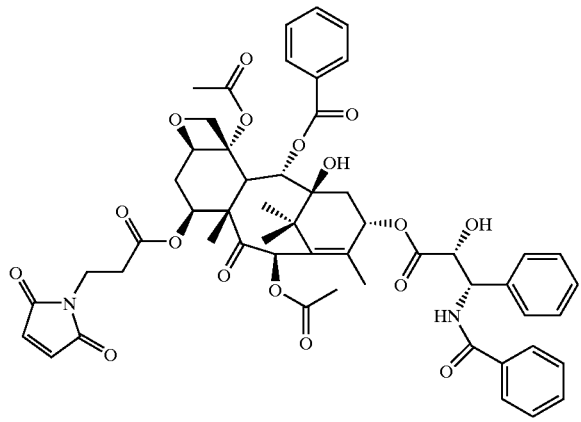

A solution of 2'-p-methoxytrityl)-7-(maleimidopropionoyl)paclitaxel (17 μmol, 22 mg), anisole (1.72 mmol, 186.4 mg) and chloroacetic acid (0.172 mmol, 16.3 mg) in $CH_2Cl_2$ (10 mL) was stirred for 4 h. The reaction mixture was washed with 1% aq $Na_2CO_3$, water, brine and was dried on $MgSO_4$. The solvent was evaporated to dryness and the residue was purified by Chromatotron®& centrifugal thin-layer chromatography (1:1 EtOAc/PE) to afford pure title compound as a white solid (24 mg), which was recrystallised from $EtOAc/CH_2Cl_2$. $^1$H-NMR (300 MHz, $CDCl_3$) δ: 1.15, 1.18, 1.20, 1.76, 2.04 (s, each 3H, $CH_3$x4), 2.18, 2.37 (s, each 3H, Ac—$CH_3$x2), 2.34 (m, 2H, H6), 2.64 (m, 4H, H14, $CH_2$), 3.78–3.91 (m, 3H, $CH_2$, H3), 4.12 (m, 2H, H20), 4.71 (d, 1H, J=3.25 Hz, H2'), 4.94 (d, 1H, J=8.17 Hz, H5), 5.54 (dd, 1H, J=10.46, 7.21 Hz, H7), 5.66 (d, 1H, J=6.88 Hz, H3'), 5.80 (dd, 1H, J=8.92, 2.42 Hz, H2), 6.15 (m, 1H, H13), 6.18 (s, 1H, H10), 6.68 (s, 2H, CH=CH), 7.10–8.12 (m, 15H, Ph).

7-[Succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27)

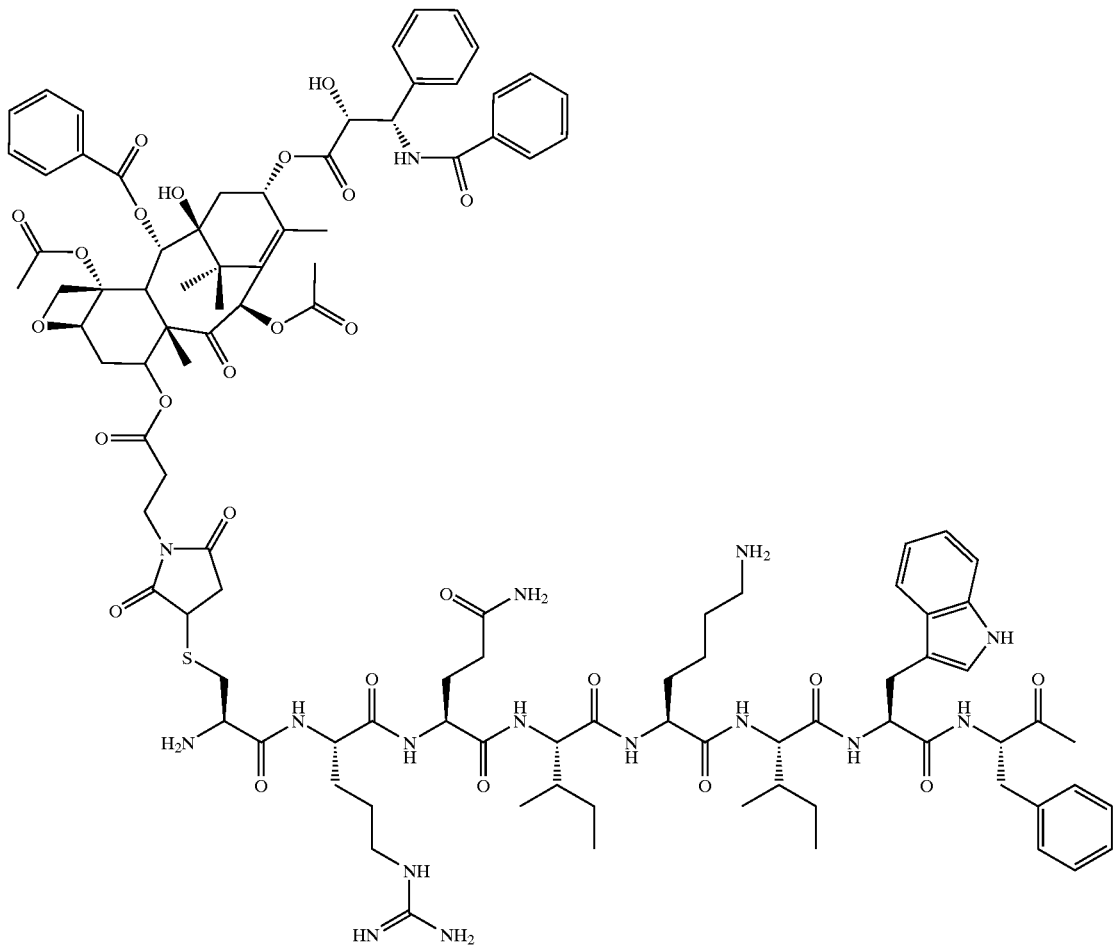

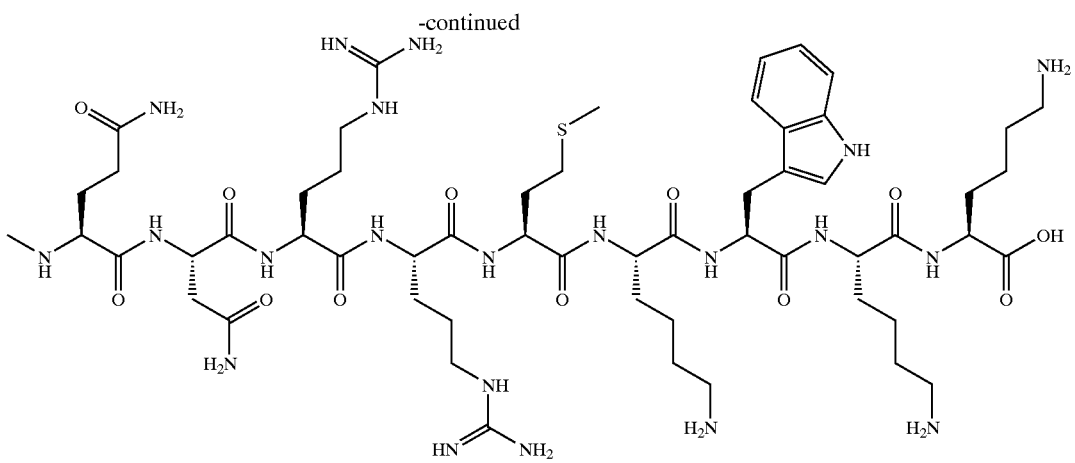

To a solution of 7-(maleimidopropionoyl)paclitaxel (4.8 μmol, 4.8 mg) and H-Cys-Arg-Gln-Ile-Lys-Ile-Trp-Phe-Gln-Asn-Arg-Arg-Met-Lys-Trp-Lys-Lys-OH (SEQ ID No. 27) (4.8 μmol, 11.2 mg) in DMF (1 mL) was added Et$_3$N (0.67 μL). The mixture was stirred for 30 min, filtered and purified by preparative RP-HPLC (10–70% MeCN gradient) to afford the pure title compound as a colourless solid (8.6 mg, 54%). Anal. RP-HPLC: t$_R$=14.3 min (10–70% MeCN gradient, purity>97%). DE MALDI-TOF MS: [M+H]$^+$= 3355.0 ($C_{161}H_{229}N_{37}O_{38}S_2$=3354.90).

Example 10

4-(Maleimidopropionoyl)podophyllotoxin

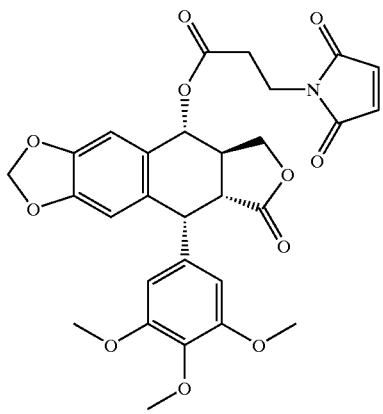

A solution of podophyllotoxin (60 μmol, 25.6 mg), 3-maleimidopropionic acid (0.31 mmol, 52.4 mg), DIC (0.17 mmol, 21.5 mg) and DMAP (80 μmol, 10 mg) in CH$_2$Cl$_2$ (2 mL) was stirred for 1 h. The solvent was evaporated in vacuo and the residue was redissolved in DMF/MeOH (1 mL) and purified by preparative RP-HPLC (20–70% MeCN gradient) to afford the pure title compound as a colourless solid (7.3 mg). Anal. RP-HPLC: t$_R$=20.1 min (0–60% MeCN gradient, purity>95%). $^1$H-NMR (300 MHz, CDCl$_3$) δ: 2.66–2.71 (t, J=6.3 Hz, 2H, CH$_2$), 2.82–2.84 (m, 2H, H2 and H3), 3.69 (s, 6H, OCH$_3$x2), 3.75 (s, 3H, OCH$_3$), 3.83 (t, J)=6.3 Hz, 2H, CH$_2$), 4.12 (t, J=9.92 Hz, 1H, H11), 4.31 (m, 1H, H11), 4.53 (d, J=11.4 Hz, 1H, H1), 5.80 (d, J=8.7 Hz, 1H, H4), 5.92 (dd, J=5.49, 1.17 Hz, 2H, OCH$_2$O), 6.32 (s, 2H, H2'6'), 6.47 (s, 1H, H8), 6.66 (s, 2H, CH=CH), 6.74 (s, 1H, H5).

4-[Succinimidopropionoyl-(H-Cys-Arg-Gln-Ile-Lys-Ill-Trp-Phe-Gln-Asn-Arg-Arg-Met-Lys-Trp-Lys-Lys-OH)]podophyllotoxin (SEQ ID No. 27)

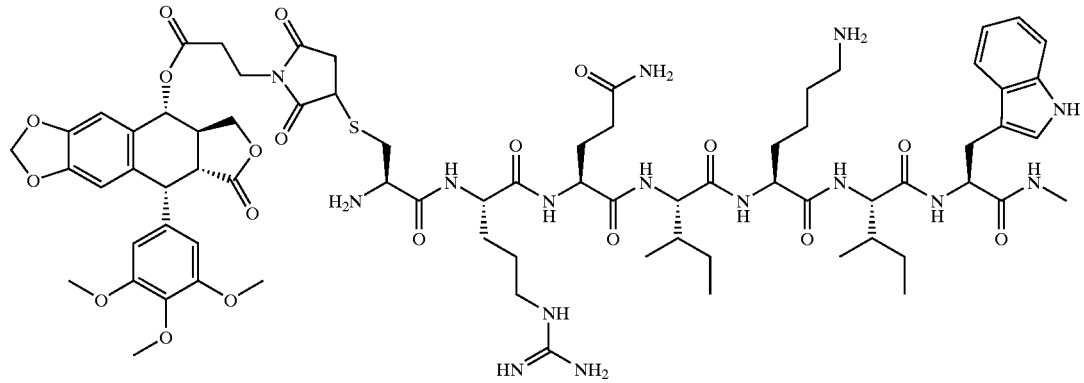

-continued

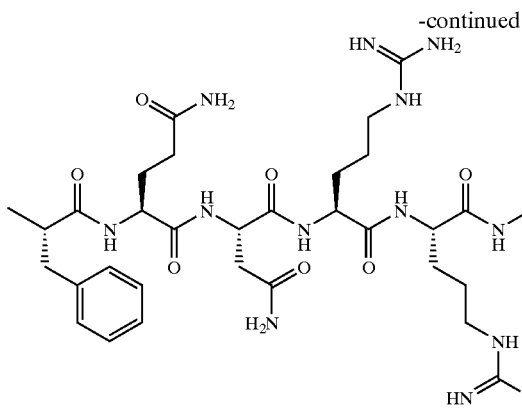

To a solution of 4-(maleimidopropionoyl) podophyllotoxin (8 μmol, 5 mg) and H-Cys-Arg-Gln-Ile-Lys-Ile-Trp-Phe-Gln-Asn-Arg-Arg-Met-Lys-Trp-Lys-Lys-OH (SEQ ID No. 27) (7.7 μmol, 18 mg) in 1 DMF (1 mL) was added Et$_3$N (1.06 μL, 11.4 μmol). The mixture was stirred for 30 min, diluted with 0.1% aq TFA (0.5 mL), filtered and purified by preparative RP-HPLC (10–60% MeCN gradient) to afford the pure title compound as a colourless solid (7.8 mg, 35%). Anal. RP-HPLC: t$^R$=12.8 min (0–60% MeCN gradient, purity>97%). DE MALDI-TOF MS: [M+H]$^+$=2915.34 (C$_{136}$H$_{200}$N$_{36}$O$_{32}$S$_2$=2915.40).

Example 11

Biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$ (SEQ ID No. 18)

H-βAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Gly-Cys(Trt)-Gly-resin (SEQ ID No. 18) (450 mg, 75 μmol) was stirred with a solution of biotinamidocaproic acid N-hydroxysuccinimidyl ester (136 mg, 0.3 mmol), HOBt (41 mg, 0.3 mmol) and DIEA (105 μL, 0.6 mmol) in DMF (3 mL) for 18 h. The peptidyl resin was collected on a sinter and washed successively with DMF, CH$_2$Cl$_2$, and Et$_2$O. After drying in vacuo, it was treated with cleavage reagent (5 mL, 1.5 h). The biotinylated peptide was isolated by precipitation with Et$_2$O and centrifugation (244 mg product). An aliquot (120 mg) was purified by preparative RP-HPLC (20–30% MeCN gradient) to afford the pure title compound as a colourless solid (63.8 mg). Anal. RP-HPLC: t$_R$=16.7 min (20–30% MeCN gradient, purity>99%, λ=214 nm). DE MALDI-TOF MS: [M+H]$^+$=2874.3, [2M+H]$^+$=5738.7, [M+2H]$^{2+}$=1437.8 (C$_{130}$H$_{210}$N$_{42}$O$_{26}$S$_3$=2873.52).

4-[Succinimidopropionoyl-(biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$)] podophyllotoxin (SEQ ID No. 18)

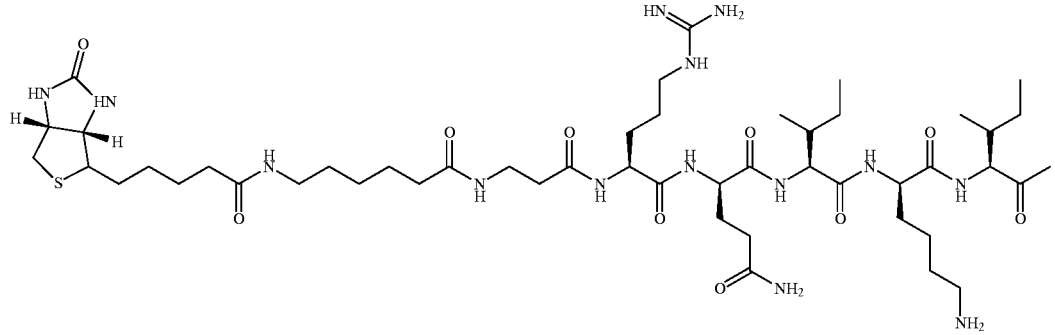

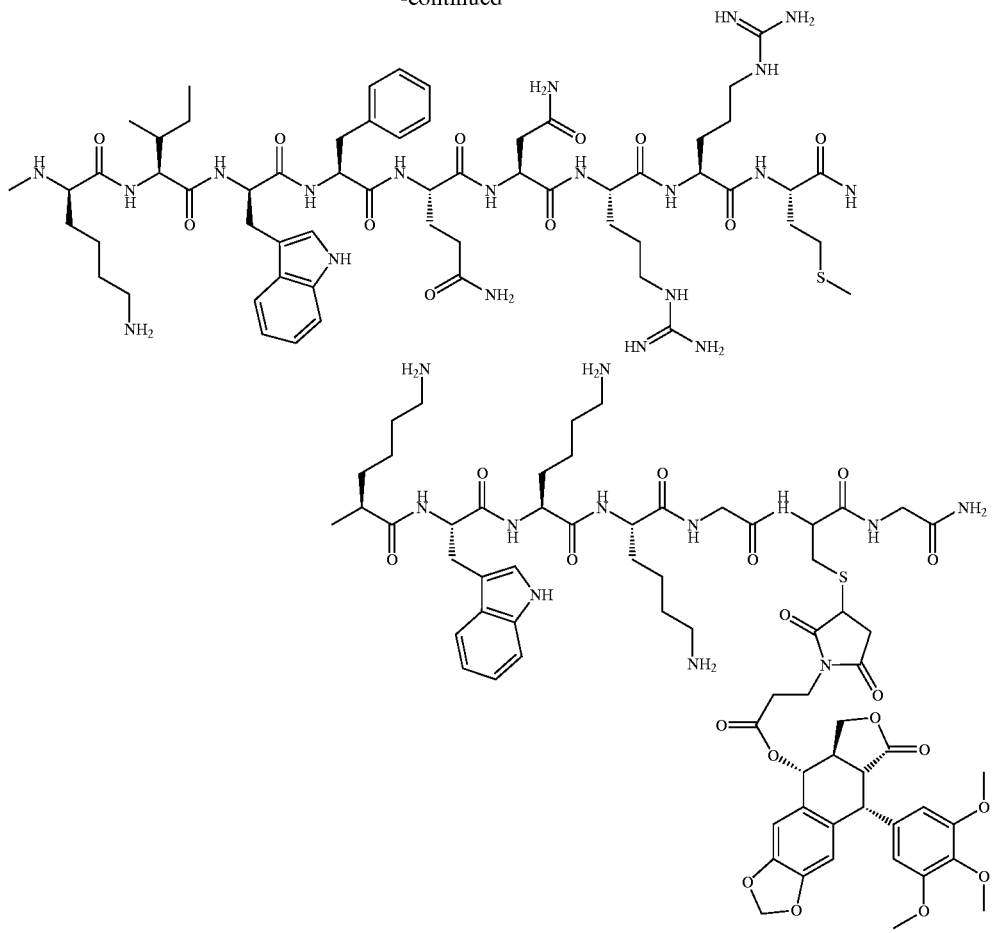

To a solution of 4-(maleimidopropionoyl) podophyllotoxin (7 μmol, 4 mg) and biotinamidocaproyl-bAla-Arg-Gln-Ile-Lys-Ile-Trp-Phe-Gln-Asn-Arg-Arg-Met-Lys-Trp-Lys-Lys-Gly-Cys-Gly-NH₂ (SEQ ID No. 18) (7 μmol, 20.7 mg) in DMF (0.5 mL) was added Et₃N (1.0 μL). The mixture was stirred for 1 h, diluted with 0.1% aq TFA (0.5 mL), filtered and purified by preparative RP-HPLC (10–70% MeCN gradient). The pure title compound was obtained as a colourless solid (2.2 mg). Anal. RP-HPLC: $t_R$=17.2 min (0–60% MeCN gradient, purity>97%). DE MALDI-TOF MS: [M+H]⁺=3438.9 ($C_{159}H_{237}N_{43}O_{37}S^2$=3439.05).

Example 12

4-[Succinimidopropionoyl-(H-Cys-Arg-Gln-Ile-Lys-Ile-Trp-Phe-Gln-Asn-Arg-Arg-Met-Lys-Trp-Lys-Lys-NH₂)]podophyllotoxin (SEQ ID No. 27)

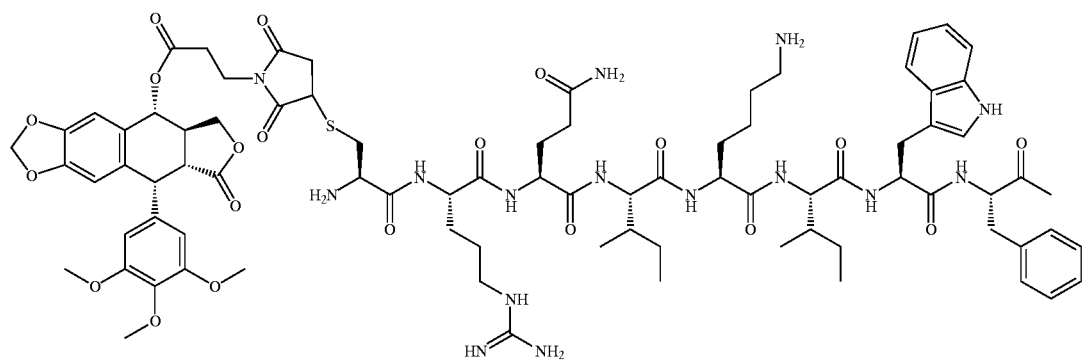

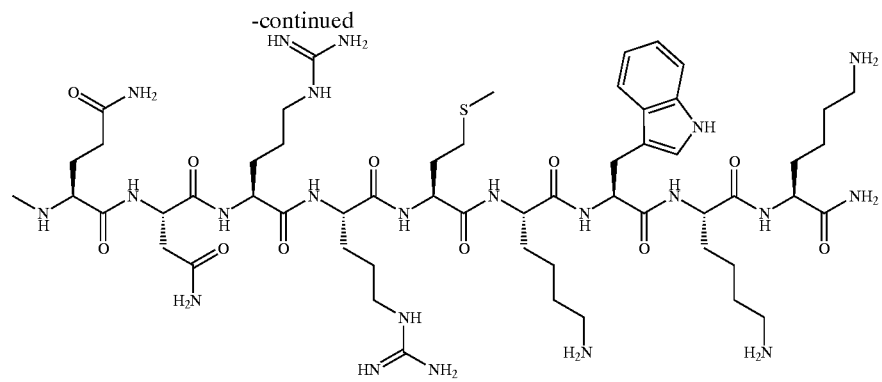

To a solution or 4-maleimidopropionoyl)podophyllotoxin (20 μmol, 12.2 mg) and H-Cys-Arg-Gln-Ile-Lys-Ile-Trp-Phe-Gln-Asn-Arg-Arg-Met-Lys-Trp-Lys-Lys-NH$_2$ (SEQ ID No. 27) (15 μmol, 34.7 mg) in DMF (1.5 mL) was added Et$_3$N (5 μL). The mixture was stirred for 40 min and purified by preparative RP-HPLC (0–60% MeCN gradient) to afford the pure title compound as a colourless solid (30.1 mg, 69%). Anal. RP-HPLC: $t_R$=15.8 min (0–60% MeCN gradient, purity>98%). DE MALDI-TOF MS: [M+H]$^+$= 2914.4 ($C_{136}H_{201}N_{37}O_{31}S_2$=2914.41).

Example 13

H-Cys-D-Arg-D-Gln-D-Ile-D-Lys-D-Ile-D-Trp-D-Phe-D-Gln-D-Asn-D-Arg-D-Arg-D-Nle-D-Lys-D-Trp-D-Lys-D-Lys-NH$_2$ (SEQ ID No. 27)

Starting from Rink Amide AM resin (0.69 mmol/g, Novabiochem), H-Cys(Trt)-D-Arg(Pmc)-D-Gln(Trt)-D-Ile-D-Lys(Boc)-D-Ile-D-Trp-D-Phe-D-Gln(Trt)-D-Asn(Trt)-D-Arg(Pmc)-D-Arg(Pmc)-D-Nle-D-Lys(Boc)-D-Trp-D-Lys(Boc)-D-Lys(Boc)-resin (SEQ ID No. 27) was assembled. After deprotection (1.5 h), the crude peptide was obtained by precipitation from Et$_2$O, centrifugation/decantation, and drying. Aliquots (total 246 mg) were purified by preparative RP-HPLC (17.5–27.5% MeCN gradient) to afford the pure title compound (45.9 mg). Anal. RP-HPLC: $t_R$=16.9 min (17.5–27.5% MeCN gradient, purity>99%, I=214 nm). DE MALDI-TOF MS: [M+H]$^+$=2330.3 ($C_{108}H_{176}N_{36}O_{20}S$= 2330.85).

4-[Succinimidopropionoyl-(H-Cys-D-Arg-D-Gln-D-Ile-D-Lys-D-Ile-D-Trp-D-Phe-D-Gln-D-Asn-D-Arg-D-Arg-D-Nle-D-Lys-D-Trp-D-Lys-D-Lys-NH$_2$)] podophyllotoxin (SEQ ID No. 27)

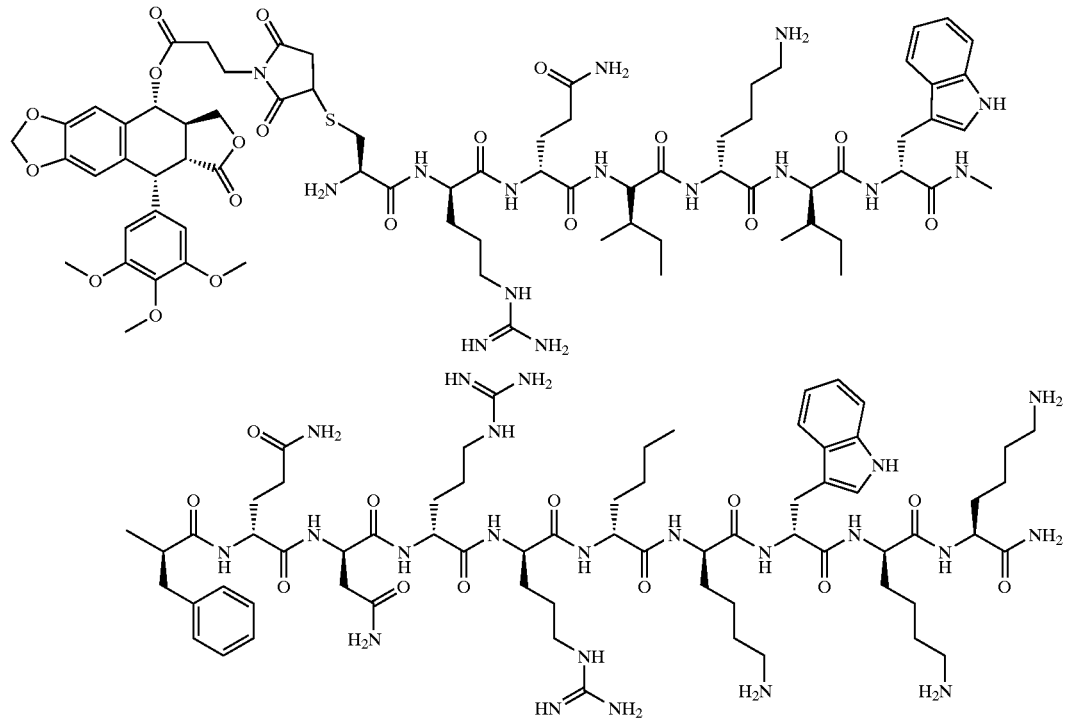

To a solution of 4-(maleimidopropionoyl) podophyllotoxin (11 μmol, 6.2 mg) and H-Cys-D-Arg-D-Gln-D-Ile-D-Lys-D-Ile-D-Trp-D-Phe-D-Gln-D-Asn-D-Arg-D-Arg-D-Nle-D-Lys-D-Trp-D-Lys-D-Lys-NH$_2$ (SEQ ID No. 27) (7 μmol, 17 mg) in DMF (1 mL) was added Et$_3$N (1.4 μL). The mixture was stirred for 30 min, filtered and purified by preparative RP-HPLC (0–60% MeCN gradient) to afford the pure title compound as a colourless solid (10.5 mg, 52%). Anal. RP-HPLC: $t^R$=15.8 min (0–60% MeCN gradient, purity>98%). DE MALDI-TOF MS: [M+H]$^+$= 2895.66 ($C_{137}H_{203}N_{37}O_{31}S_2$=2896.37).

Example 14

4-[Succinimidopropionoyl-CH-Cys-βAla-Arg-Arg-Met-Lys-Trp-Lys-Lys-NH$_2$)]podophyllotoxin (SEQ ID No. 19)

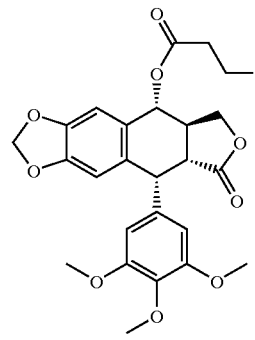

To a solution of 4-(maleimidopropionoyl) podophyllotoxin (17.7 μmol, 10 mg) and H-Cys-βAla-Arg-Arg-Met-Lys-Trp-Lys-Lys-NH$_2$ (SEQ ID No. 19) (25 μmol, 30.4 mg) in DMF (1.5 mL) was added Et$_3$N (3.5 μL). The mixture was stirred for 40 min, filtered and purified by preparative RP-HPLC (0–60% MeCN gradient). The pure title compound was obtained as a colourless solid (17.8 mg, 57%). Anal. RP-HPLC: $t_R$=14.8 min (0–60% MeCN gradient, purity>98%). DE MALDI-TOF MS: [M+H]$^+$= 1772.3 ($C_{81}H_{119}N_{21}O_{20}S_2$=1771.07).

Example 15

H-Cys-βAla-D-Arg-D-Arg-D-Met-D-Lys-D-Trp-D-Lys-D-Lys-NH$_2$ (SEQ ID No. 19)

Starting from Rink Amide AM resin (0.69 mmol/g, Novabiochem), H-Cys(Trt)-βAla-D-Arg(Pmc)-D-Arg(Pmc)-D-Met-D-Lys(Boc)-D-Trp-D-Lys(Boc)-D-Lys(Boc)-resin (SEQ ID No. 19) was assembled. After deprotection (1.5 h), the crude peptide was obtained by precipitation from Et$_2$O, centrifugation/decantation, and drying. Aliquots (total

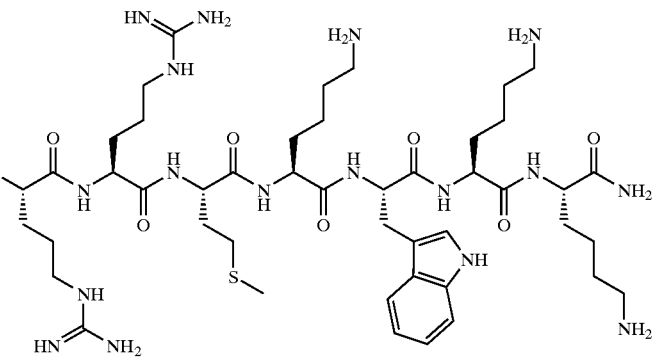

237 mg) were purified by preparative RP-HPLC (8–18% MeCN gradient) to afford the pure title compound (66 mg). Anal. RP-HPLC: $t_R$=12.9 min (9–19% MeCN gradient, purity>99%, λ=214 nm). DE MALDI-TOF MS: [M+H]$^+$= 1207.2 ($C_{52}H_{92}N_{20}O_9S_2$=1205.55).

4-[Succinimidopropionoyl-(H-Cys-b-Ala-D-Arg-D-Arg-D-Met-D-Lys-D-Trp-D-Lys-D-Lys-NH$_2$)] podophyllotoxin (SEQ ID No. 19)

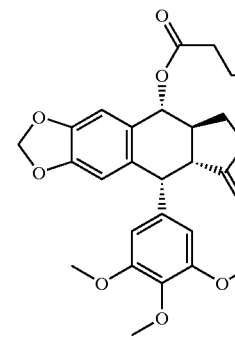
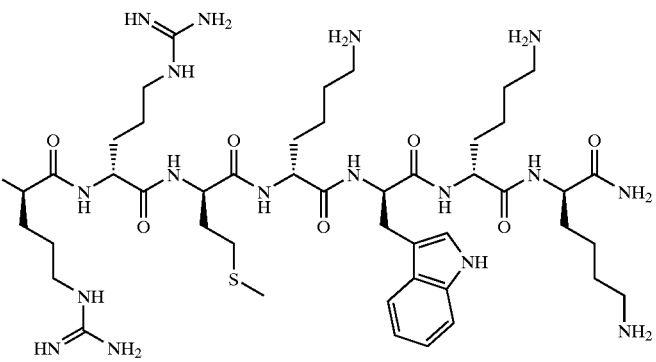

To a solution of 4-(maleimidopropionoyl) podophyllotoxin (18.9 μmol, 10.7 mg) and H-Cys-βAla-D-Arg-D-Arg-D-Met-D-Lys-D-Trp-D-Lys-D-Lys-NH$_2$ (SEQ ID No. 19) (28 μmol, 33.8 mg) in DMF (1.5 mL) was added Et₃N (1.5 μL). The mixture was stirred for 40 min, filtered and purified by preparative RP-HPLC (0–60% MeCN gradient). The pure title compound was obtained as a colourless solid (6.9 mg, 21%). Anal. RP-HPLC: $t_R$=14.8 min (0–60% MeCN gradient, purity>98%). DE MALDI-TOF MS: [M+H]⁺=1771.5 ($C_{81}H_{119}N_{21}O_{20}S_2$=1771.07).

Example 16

4'-(Maleimidopropionoyl)epipodophyllotoxin

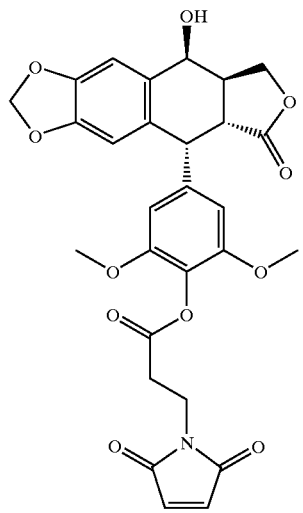

A solution of 4'-demethylepipodophyllotoxin (12 mmol, 5 mg), 3-maleimidopropionic acid (50 μmol, 12.2 mg) and DIC (28 μmol, 3.47 mg) in pyridine (1 mL) was stirred for 30 min. MeOH (0.5 mL) was added and the mixture was purified by preparative RP-HPLC (0–60% MeCN gradient) to afford the pure title compound as a colourless solid (4.2 mg, 62%). Anal. RP-HPLC: $t_R$=17.6 min (0–60% MeCN gradient, purity>95%). ¹H-NMR (300 MHz, CDCl₃) δ: 2.84 (m, 1H, H3), 2.99 (t, J=7.44 Hz, 2H, CH₂-Mim), 3.32 (dd, J=14.04, 5.07 Hz, 1H, H2), 3.69 (s, 6H, OCH₃x2), 3.95 (t, J=7.44 Hz, 2H, CH₂-Mim), 4.39 (dd, J=8.13, 4.28 Hz, 2H, H11), 4.66 (d, J=5.00 Hz, 1H, H1), 4.89 (d, J=3.32 Hz, 1H, H4), 6.01 (d, J=6.42 Hz, 2H, OCH₂O), 6.32 (s, 2H, H2'6'), 6.57 (s, 1H, H8), 6.74 (s, 2H, CH=CH), 6.90 (s, 1H, H5). ¹³C-NMR (75 MHz, CDCl₃) δ: 28.64, 31.02, 32.55, 37.33, 39.53, 42.99, 55.15, 65.78, 66.56, 100.65, 106.54, 107.97, 109.65, 130.68, 130.92, 133.21, 136.96, 146.62, 147.61, 150.39, 167.36, 169.30, 173.89.

4'-[Succinimidopropionoyl-(H-Cys-Arg-Gln-Ile-Lys-Ile-Trp-Phe-Gln-Asn-Arg-Arg-Met-Lys-Trp-Lys-Lys-OH)]epipodophyllotoxin (SEQ ID No. 27)

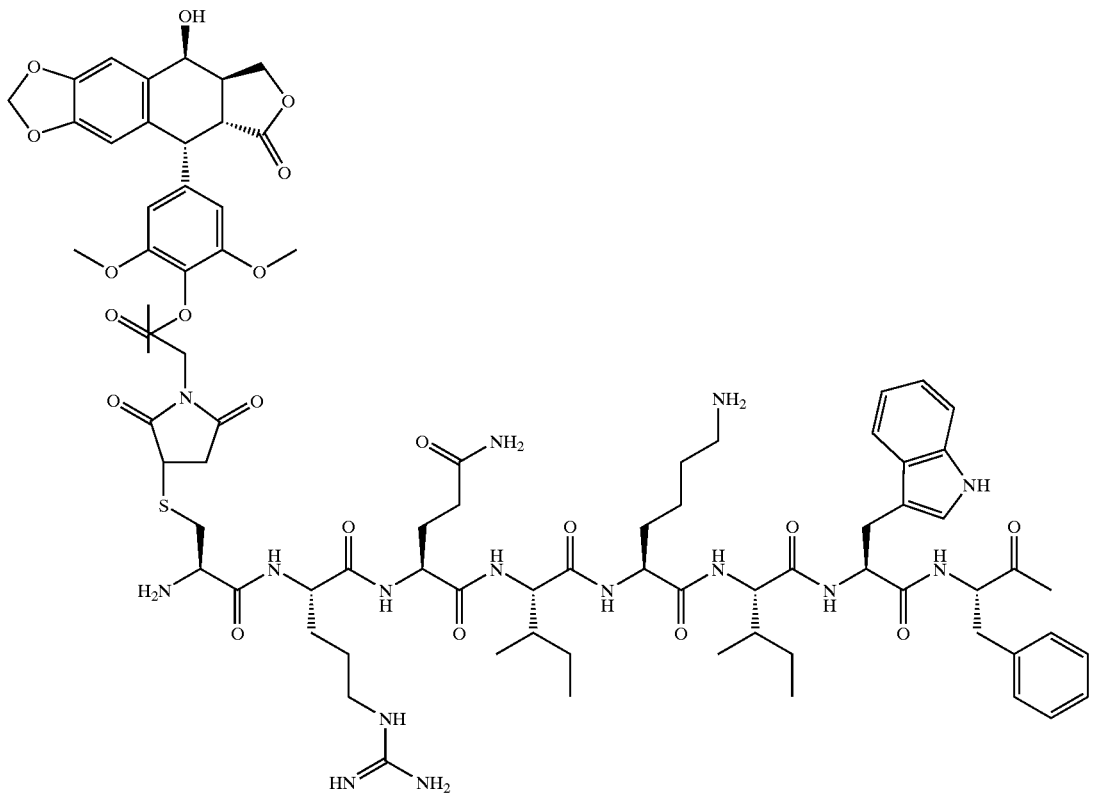

-continued

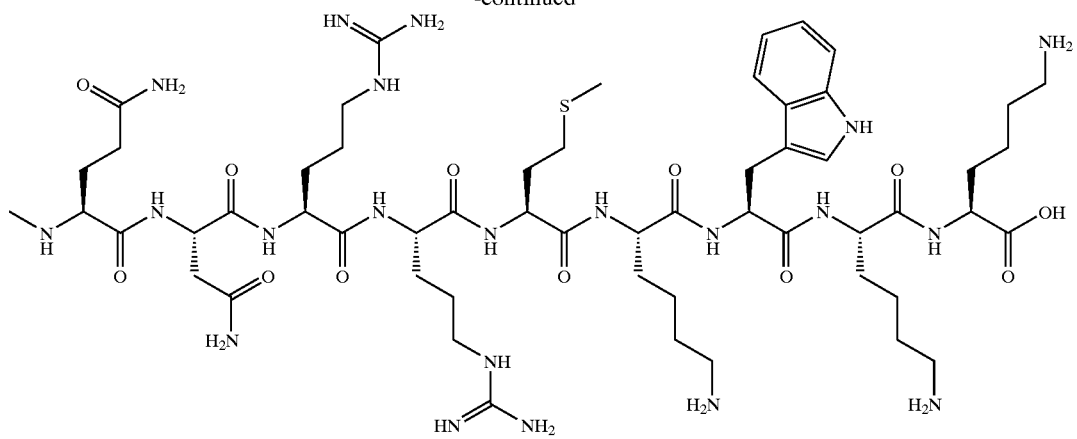

To a solution of 4'-(maleimidopropionoyl) epipodophyllotoxin (2.3 μmol, 1.3 mg) and H-Cys-Arg-Gln-Ile-Lys-Ile-Trp-Phe-Gln-Asn-Arg-Arg-Met-Lys-Trp-Lys-Lys-OH (SEQ ID No. 27) (2.3 μmol, 5.4 mg) in DMF (0.5 mL) was added Et$_3$N (0.21 μL, 2.3 μmol). The mixture was stirred for 40 min, diluted with 0.1% aq TFA (1 mL), filtered and purified by preparative RP-HPLC (0–60% MeCN gradient) to afford the pure title compound as a colourless solid (3.2 mg, 48%). Anal. RP-HPLC: t$_R$=14.6 min (0–60% MeCN gradient, purity>98%). DE MALDI-TOF MS: [M+H]$^+$=2902.2 ($C_{135}H_{198}N_{36}O_{32}S_2$=2901.37).

Example 17

4'-[Succinimidopropionoyl-(H-Cys-Arg-Gln-Ile-Lys-Ile-Trp-Phe-Gln-Asn-Arg-Arg-Met-Lys-Trp-Lys-Lys-NH$_2$)]epipodophyllotoxin (SEQ ID No. 27)

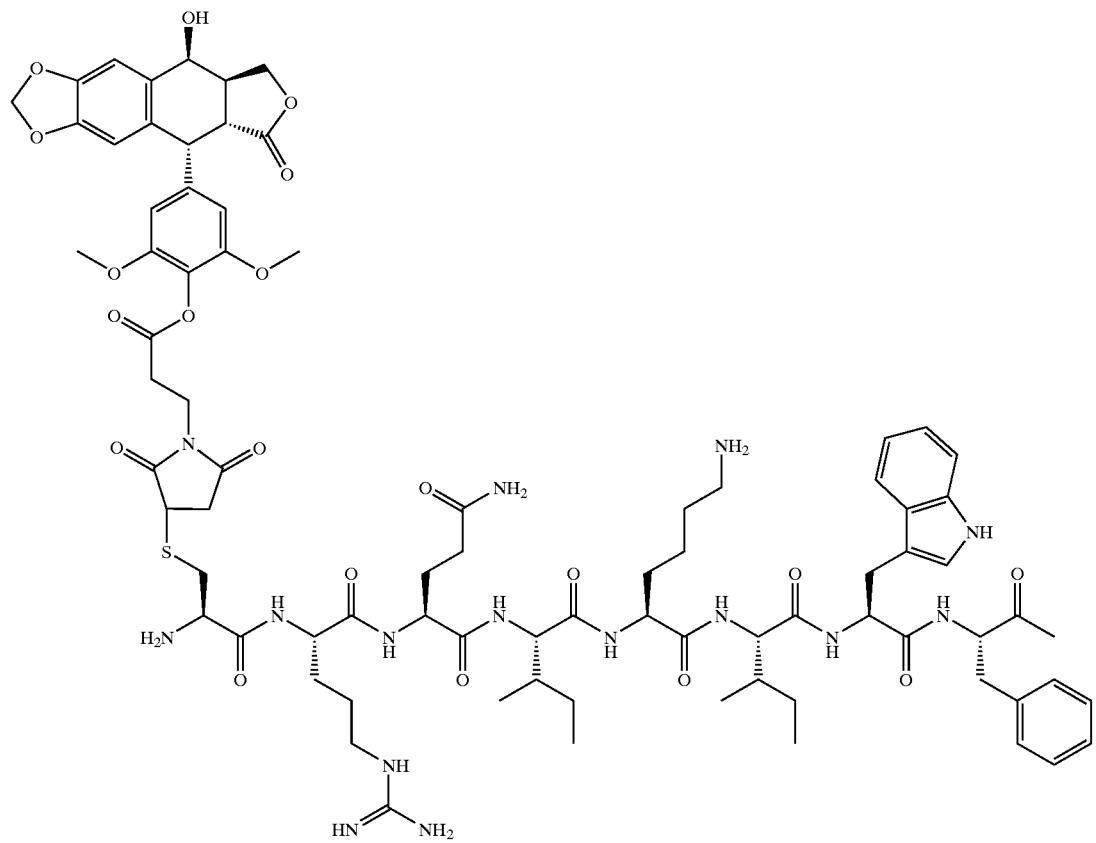

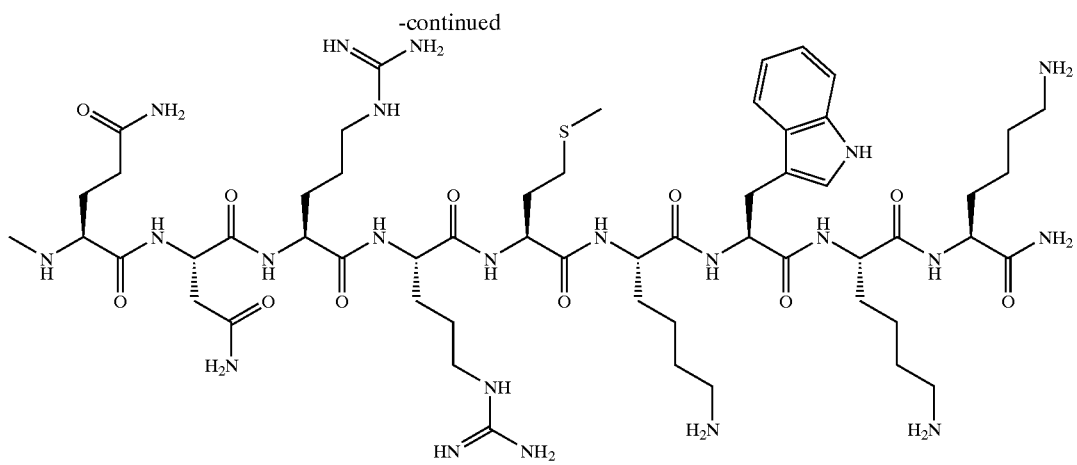

To a solution of 4'-(maleimidopropionoyl)epipodophyllotoxin (7 μmol, 4 mg) and H-Cys-Arg-Gln-Ile-Lys-Ile-Trp-Phe-Gln-Asn-Arg-Arg-Met-Lys-Trp-Lys-Lys-NH$_2$ (SEQ ID No. 27) (6 μmol, 15 mg) in DMF (0.5 mL) was added Et$_3$N (1 μL). The mixture was stirred for 40 min and was purified by preparative RP-HPLC (0–60% MeCN gradient) to afford the pure title compound as a colourless solid (14.1 mg, 81%). Anal. RP-HPLC: t$_R$=19.7 min (0–60% MeCN gradient, purity>98%). DE MALDI-TOF MS: [M+H]$^+$=2900.4, C$_{135}$H$_{199}$N$_{37}$O$_{31}$S$_2$=2900.39.

Example 18

4'-[Succinimidopropionoyl-(H-Cys-βAla-Arg-Arg-Met-Lys-Trp-Lys-Lys-NH$_2$)]epipodophyllotoxin
(SEQ ID No. 19)

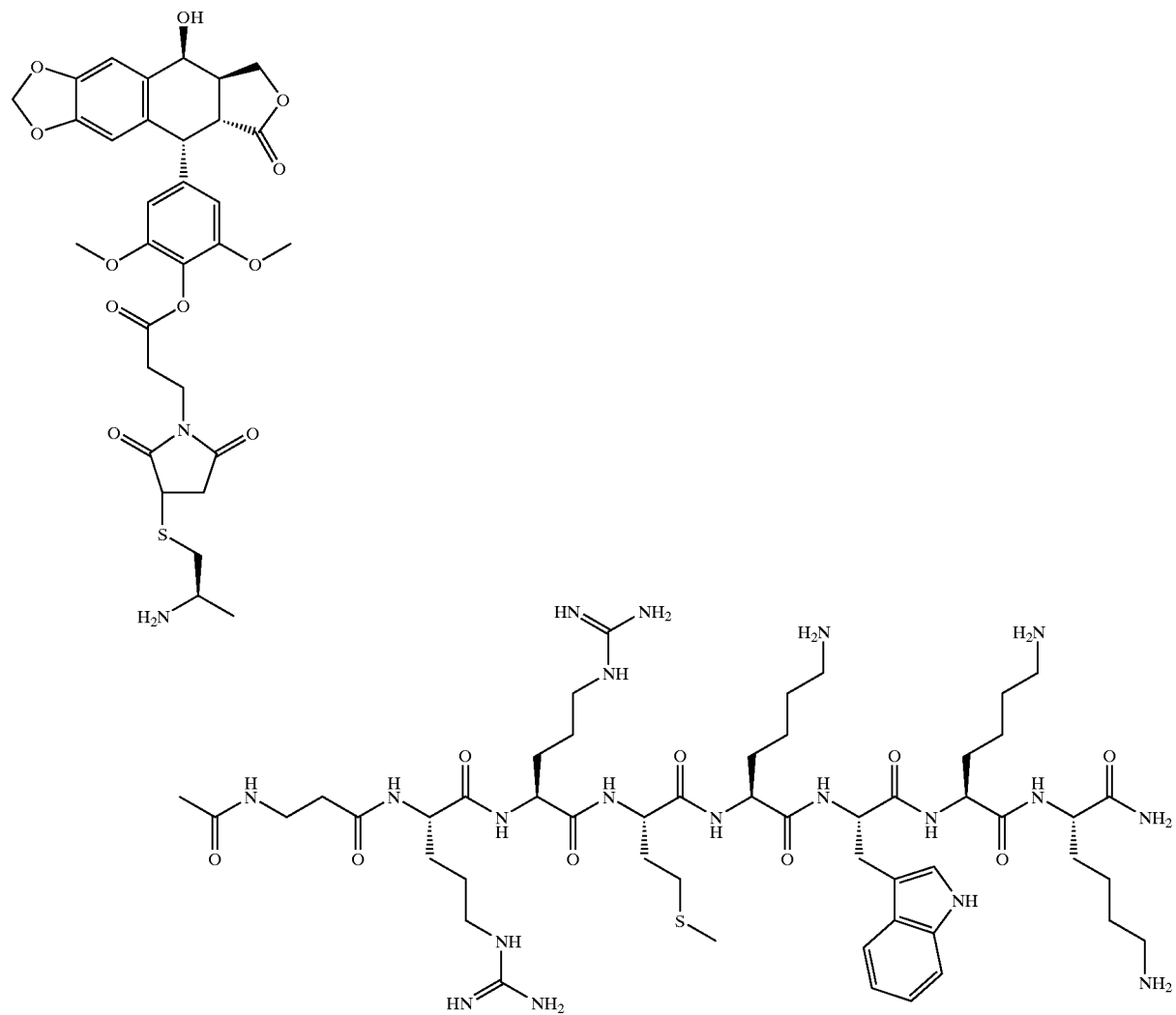

To a solution of 4'-(maleimidopropionoyl) epipodophyllotoxin (14 μmol, 7.9 mg) and H-Cys-βAla-Arg-Arg-Met-Lys-Trp-Lys-Lys-NH$_2$ (SEQ ID No. 19) (26 μmol, 31.5 mg) in DMF (1 mL) was added Et$_3$N (1.9 μL). After stirring for 40 min, the mixture was purified by preparative RP-HPLC (0–60% gradient) to afford the pure title compound as a colourless solid (15.8 mg, 63%). Anal. RP-HPLC: t$_R$=13.3 min (0–60% MeCN gradient, purity>98%). DE MALDI-TOF MS: [M+H]$^+$=1757.2 (C$_{80}$H$_{117}$N$_{21}$O$_{20}$S$_2$=1757.05).

Example 19

4'-(Chloroacetyl)epipodophyllotoxin

To a stirring solution of 4'demethylepipodophyllotoxin (0.50 mmol, 200 mg) and pyridine (40 μL) in CH$_2$Cl$_2$ (2 mL) at 0° C., chloroacetyl chloride (0.50 mmol, 56.5 mg) was added dropwise. By anal. RP-HPLC about 60% of 4'-demethylepipodophyllotoxin starting material was consumed after 1 hr stirring at 0° C. The reaction mixture was poured into chilled water and this was extracted with CH$_2$Cl$_2$. The organic layer was washed with water, brine and was dried on MgSO4. The solvent was evaporated in vacuo and the residue was purified by flash chromatography (5:4–3:2 EtOAc/PE). The pure title compound was obtained after recrystallisation from EtOAc/PE as a colourless solid (81.5 mg, 34%). $^1$H-NMR (300 MHz, CDCl$_3$) δ: 2.78 (m, 1H, H3), 3.25 (dd, J=14.12, 5.07 Hz, 1H, H2), 3.68 (s, 6H, OCH$_3$x2), 4.30 (m, 2H, H11), 4.35 (s, 2H, CH2Cl), 4.57 (d, J=5.12 Hz, 1H, H1), 4.83 (d, J=3.37 Hz, H4), 5.96 (d, J=4.10 Hz, 2H, OCH$_2$O), 6.32 (s, 2H, H2'6'), 6.50 (s, 1H, H8), 6.87 (s, 1H, H5).

4'-Chloroacetyl-4-maleimidopropionoyl) epipodophyllotoxin

A solution of 4'-(chloroacetyl)epipodophyllotoxin (0.17 mmol, 81.5 mg), 3-maleimidopropionic acid (0.68 mmol, 115.6 mg), DIC (0.376 mmol, 47.5 mg), DMAP (73 μmol, 9 mg) and pyridine (20 μL) in CH$_2$Cl$_2$ (2 mL) was stirred for 1 h. The solvent was evaporated to dryness. The resulting light-yellow solid was redissolved in DMF (1 mL) and was purified by preparative RP-HPLC (30–70% MeCN gradient) to afford the pure title compound as a colourless solid (54.3 mg, 51%). Anal. RP-HPLC: t$_R$=22.0 min (0–60% MeCN gradient, purity>97%). $^1$H-NMR (300 MHz, CDCl$_3$) δ: 2.71 (t, 2H, J=6.80 Hz, CH$_2$-Mim), 2.98 (m, 1H, H3), 3.25 (dd, J=14.20, 5.13 Hz, 1H, H2), 3.69 (s, 6H, OCH$_3$x2), 3.87 (t, J=6.83 Hz, 2H, CH$_2$-Mim), 3.88 (m, 1H, H11), 4.33 (s, 2H, CH$_2$Cl), 4.35 (m, 1H, H11), 4.70 (d, J=5.10 Hz, 1H, H1), 6.01 (d, J=4.23 Hz, 2H, OCH$_2$O), 6.13 (d, J=3.50 Hz, 1H, H4), 6.31 (s, 2H, H2'6'), 6.56 (s, 1H, H8), 6.71 (s, 2H, CH=CH), 6.92 (s, 1H, H5).

4'-Chloroacetyl-4-[succinimidopropionoyl-(H-Cys-Arg-Gln-Ile-Lys-Ile-Trp-Phe-Gln-Asn-Arg-Arg-Met-Lys-Trp-Lys-Lys-OH)]epipodophyllotoxin (SEQ ID No. 27)

-continued

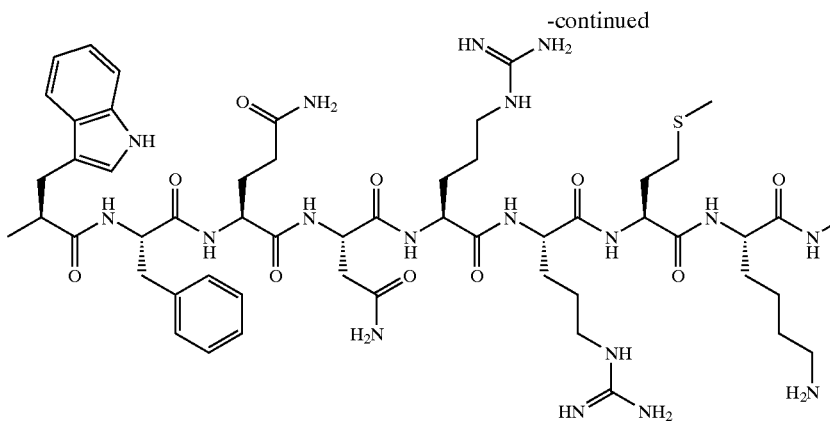
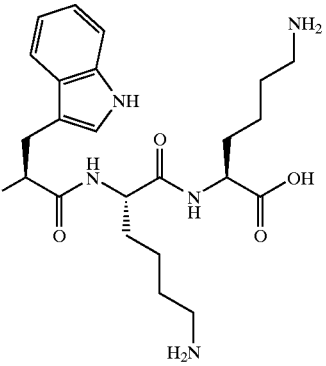

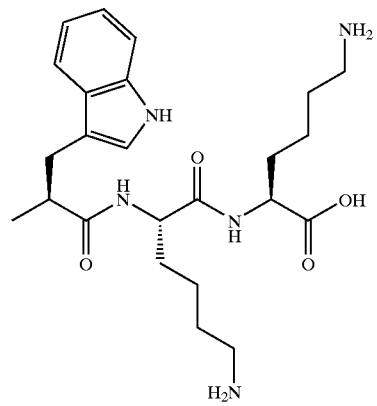

To a solution of 4'-chloroacetyl-4-(maleimidopropionoyl) epipodophyllotoxin (6.8 μmol, 43 mg) and H-Cys-Arg-Gln-Ile-Lys-Ile-Trp-Phe-Gln-Asn-Arg-Arg-Met-Lys-Trp-Lys-Lys-OH (SEQ ID No. 27) (10 μmol, 25.4 mg) in DMF (1.5 mL) was added Et$_3$N (2.5 μL). The mixture was stirred for 30 min and was purified by preparative RP-HPLC (10–70% MeCN gradient) to afford the pure title compound as a colourless solid (22 mg, 67%). Anal. RP-HPLC: t$_R$=16.7 min (0–60% MeCN gradient, purity>99%). DE MALDI-TOF MS: [M+H]$^+$=2978.3 (C$_{137}$H$_{199}$ClN$_{36}$O$_{33}$S$_2$= 2977.85).

4'-Demethyl-4-[succinimidopropionoyl-(H-Cys-Arg-Gln-Ile-Lys-Ile-Trp-Phe-Gln-Asn-Arg-Arg-Met-Lys-Trp-Lys-Lys-OH)]epipodophyllotoxin (SEQ ID No. 27)

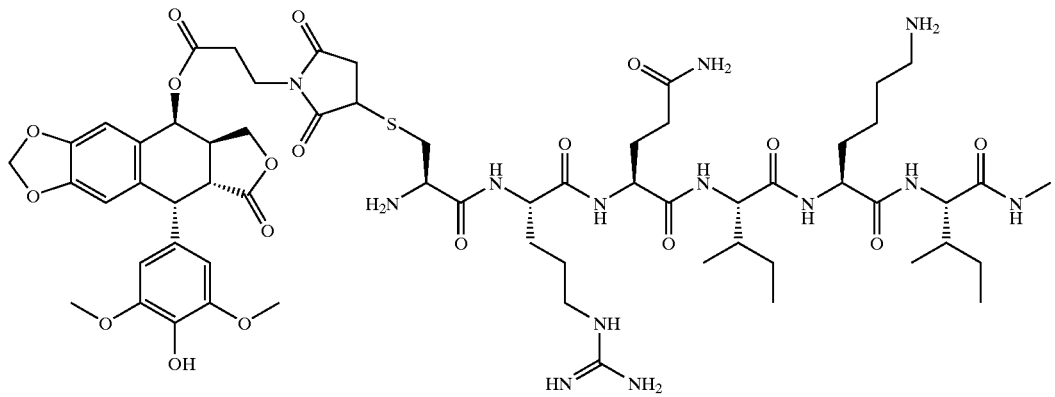

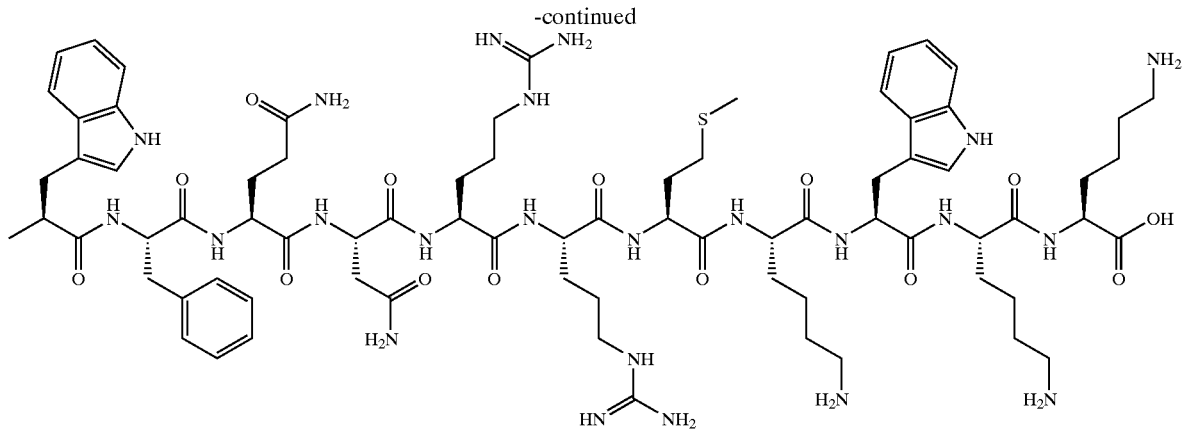

A solution of 4'-chloroacetyl-4-[succinimidopropionoyl-(H-Cys-Arg-Gln-Ile-Lys-Ile-Trp-Phe-Gln-Asn-Arg-Arg-Met-Lys-Trp-Lys-Lys-OH)]epipodophyllotoxin (SEQ ID No. 27) (5.5 μmol, 16.4 mg) in DMF (1 mL) and water (0.5 mL) at 0° C. was treated with conc. aq $NH_3$ solution (20 μL). After 2 min the reaction mixture was acidified by addition of 5% aq AcOH (0.1 mL). It was purified by preparative RP-HPLC (0–60% MeCN gradient) to afford the pure title compound as a colourless solid (11.4 mg, 73%). Anal. RP-HPLC: $t_R$=14.9 min (0–60% MeCN gradient, purity>99%). DE MALDI-TOF MS: $[M+H]^+$=2902.2 ($C_{135}H_{198}N_{36}O_{32}S_2$=2901.37).

Example 20
G2-(Maleimidopropionoyl)etoposide, G3-(maleimidopropionoyl)etoposide, and 4'-(maleimidopropionoyl)etoposide A solution of etoposide (37.4 μmol, 22 mg), 3-maleimidopropionic acid (78 μmol, 13.2 mg) and DIC (39.6 μmol, 5 mg) in a mixture of $CH_2Cl_2$/pyridine (2:0.15) was stirred for 30 min. The solvents were removed in vacuo. The resulting light-yellow solid was dissolved in MeOH (1.5 mL) and was purified by preparative RP-HPLC (10–70% MeCN gradient) to afford G2-(maleimidopropionoyl) etoposide (3.4 mg), G3-(maleimidopropionoyl)etoposide (2.4 mg) and 4'-(maleimidopropionoyl)etoposide (7.7 mg) as colourless solids (total yield 48%).

G2-(Maleimidopropionoyl)etoposide

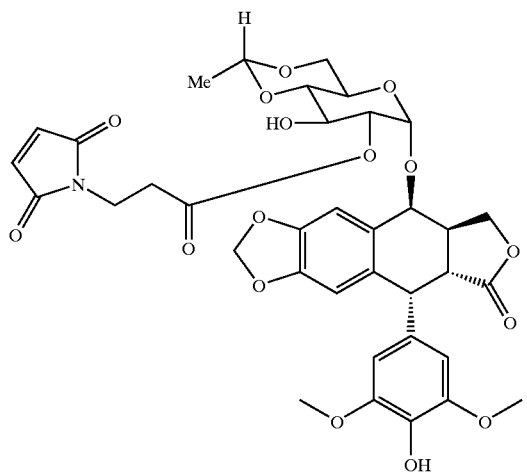

Anal. RP-HPLC: $t_R$=16.7 min (0–60% MeCN gradient, purity>99%). $^1$H-NMR (300 MHz, $CDCl_3$) δ: 1.39 (d, J=4.99 Hz, 3H, $CH_3$), 2.39 (t, J=7.30 Hz, 2H, $CH_2$-Mim), 2.87 (m, 1H, H3), 3.14 (dd, J=14.20, 5.09 Hz, 1H, H2), 3.39 (m, 2H, G4,5), 3.63 (m, 2H, G2,6), 3.72 (m, 2H, $CH_2$-Mim), 3.76 (s, 6H, $OCH_3$x2), 3.84 (t, J=8.9 Hz, 1H, G3), 4.19 (m, 2H, H11, G6), 4.38 (m, 1H, H11), 4.60 (d, J=4.10 Hz, 1H, H4), 4.74–4.84 (m, 2H, H1, G6). 6.00 (d, J=5.10 Hz, 2H, $OCH_2O$), 6.24 (s, 2H, H2'6'), 6.54 (s, 1H, H8), 6.70 (s, 2H, CH=CH), 6.75 (s, 1H, H5). $^{13}$C-NMR (75 MHz, $CDCl_3$) δ: 20.66, 33.48, 33.95, 37.86, 41.46, 44.00, 56.87, 66.75, 68.07, 68.34, 72.15, 74.61, 75.26, 80.24, 100.29, 100.434, 102.07, 108.33, 109.00, 111.33, 128.75, 130.90, 133.40, 134.50, 134.66, 146.80, 147.27, 149.09, 169.94, 170.78, 175.08.

G3-(Maleimidopropionoyl)etoposide

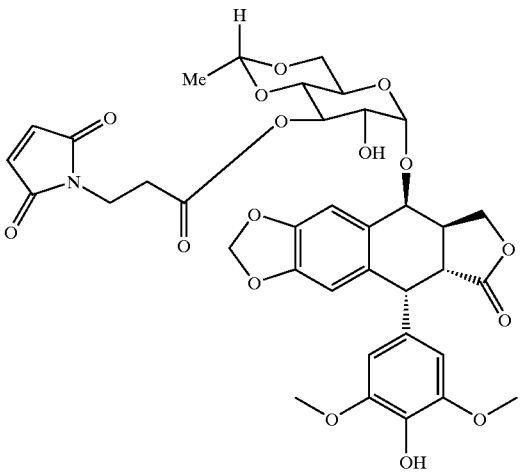

Anal. RP-HPLC: $t_R$=18.4 min (0–60% MeCN gradient, purity>99%). $^1$H-NMR (300 MHz, $CDCl_3$) δ: 1.33 (d, J=5.0 Hz, 3H, $CH_3$), 2.74 (t, J=7.35 Hz, 2H, $CH_2$-Mim), 2.91 (m, 1H, H3), 3.28 (dd, J=14.01, 5.26 Hz, 1H, H2), 3.38 (m, 2H, G4,5), 3.54 (m, 2H, G2,6), 3.87 (m, 2H, $CH_2$-Mim), 3.76 (s, 6H, $OCH_3$x2), 4.16–4.26 (m, 2H, H11, G3), 4.42 (t, J=8.98 Hz, 1H), 4.61 (d, J=5.09 Hz, 1H, H1), 4.68 (m, 1H, G1), 4.91 (d, J=3.34 Hz, H4), 5.13 (m, 1H, G3). 6.00 (d, J=11.25 Hz, 2H, OCH$_2$O), 6.26 (s, 2H, H2'6'), 6.54 (s, 1H, H8), 6.71 (s, 2H, CH=CH), 6.83 (s, 1H, H5). $^{13}$C-NMR (75 MHz, CDCl$_3$) δ: 0.67, 33.59, 34.13, 37.93, 41.62, 44.11, 56.84, 66.87, 68.26, 68.38, 73.39, 74.38, 74.49, 100.17, 102.01, 102.54, 108.25, 109.51, 111.10, 128.38, 130.89, 133.28, 134.50, 134.66, 146.84, 147.59, 149.29, 170.64, 170.80, 175.38.

4'-(Maleimidopropionoyl)etoposide

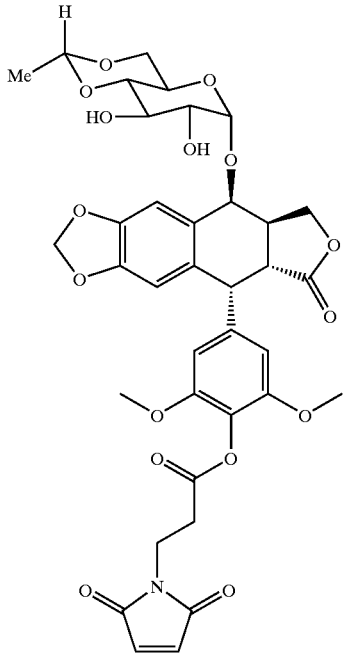

Anal. RP-HPLC: $t_R$=17.7 min (0–60% MeCN gradient, purity>99%). $^1$H-NMR (300 MHz, CDCl$_3$) δ: 1.39 (d, J=4.82 Hz, 3H, CH$_3$), 2.88 (m, 1H, H3), 2.96 (t, J=7.24 Hz, 2H, CH$_2$-Mim, 2.91 (m, 1H, H3), 3.34 (dd, J=14.01, 5.26 Hz, 1H, H2), 3.36 (m, 2H, G4,5), 3.45–3.58 (m, 2H, G2,6), 3.92 (t, J=3.20 Hz, 2H, CH$_2$-Mim), 3.65 (s, 6H, OCH$_3$x2), 3.76 (m, 1H, G3), 4.15–4.27 (m, 2H, H11, G6), 4.43 (m, 1H, H11), 4.62–4.67 (m, 2H, H1, G1), 4.75 (m, 1H, G7), 4.91 (d, J=3.27 Hz, H4), 6.00 (d, J=6.68 Hz, 2H, OCH$_2$O), 6.25 (s, 2H, H2'6'), 6.54 (s, 1H, H8), 6.71 (s, 2H, CH=CH), 6.82 (s, 1H, H5). $^{13}$C-NMR (75 MHz, CDCl$_3$) δ: 20.62, 32.41, 33.94, 37.87, 41.61, 44.31, 56.52, 66.84, 68.44, 73.47, 74.13, 74.88, 80.06, 100.24, 102.10, 102.30, 107.89, 109.36, 111.22, 128.65, 132.68, 134.61, 138.28, 147.74, 149.29, 151.76, 168.90, 170.76, 175.56.

G2-[Succinimidopropionoyl-(H-Cys-Arg-Gln-Ile-Lys-Ile-Trp-Phe-Gln-Asn-Arg-Arg-Met-Lys-Trp-Lys-Lys-OH)]etoposide (SEQ ID No. 27)

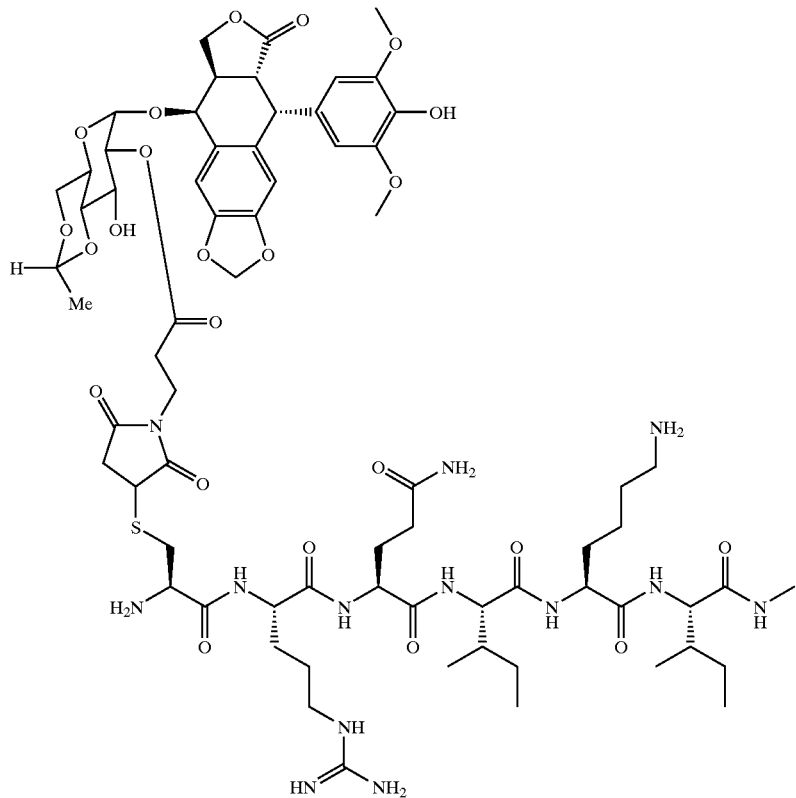

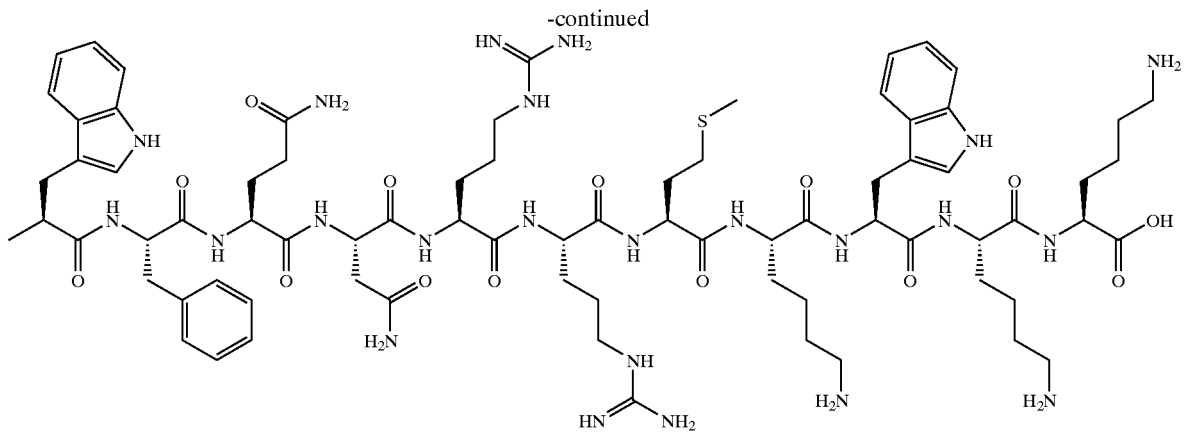

To a solution of G2-(maleimidopropionoyl)etoposide (4.4 μmol, 3.3 mg) and H-Cys-Arg-Gln-Ile-Lys-Ile-Trp-Phe-Gln-Asn-Arg-Arg-Met-Lys-Trp-Lys-Lys-OH (SEQ ID No. 27) (5.7 μmol, 13.4 mg) in DMF (0.5 mL) was added Et$_3$N (0.7 μL, 4.9 μmol). The mixture was stirred for 30 min, diluted with 0.1% aq TFA (1 mL) and purified by preparative RP-HPLC (0–60% MeCN gradient) to afford the pure title compound as a colourless solid (10.8 mg, 80%). Anal. RP-HPLC: t$_R$=14.6 min (0–60% MeCN gradient, purity>98%). DE MALDI-TOF MS: [M+H]$^+$=3091.1 (C$_{143}$H$_{210}$N$_{36}$O$_{37}$S$_2$=3089.55).

G3-[Succinimidopropionoyl-(H-Cys-Arg-Gln-Ile-Lys-Ile-Trp-Phe-Gln-Asn-Arg-Arg-Met-Lys-Trp-Lys-Lys-OH)]etoposide (SEQ ID No. 27)

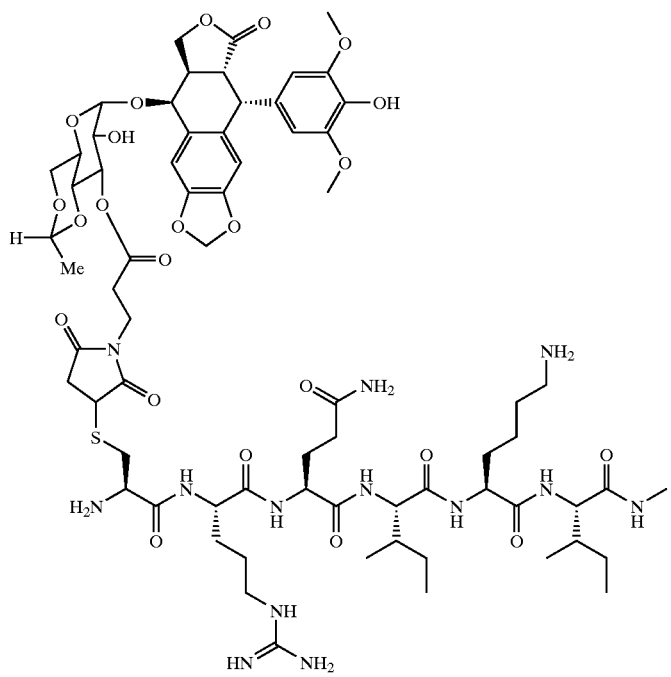

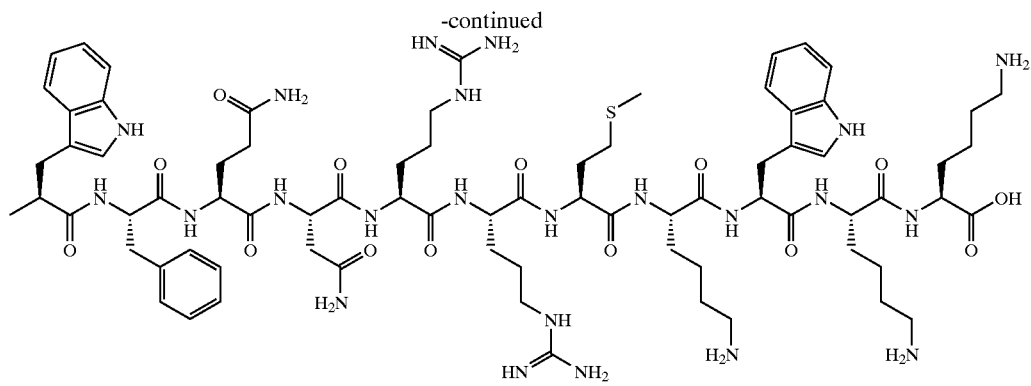

To a solution of G3-(maleimidopropionoyl)etoposide (3.1 μmol, 2.3 mg) and H-Cys-Arg-Gln-Ile-Lys-Ile-Trp-Phe-Gln-Asn-Arg-Arg-Met-Lys-Trp-Lys-Lys-OH (SEQ ID No. 27) (4.3 μmol, 10.2 mg) in DMF (0.5 mL) was added Et₃N (0.6 μL, 4.4 μmol). The mixture was stirred for 30 min, diluted with 0.1% aq TFA (1 mL) and purified by preparative RP-HPLC (0–60% MeCN gradient) to afford the pure title compound as a colourless solid (7.4 mg, 79%). Anal.

RP-HPLC: $t_R$=14.7 min (0–60% MeCN gradient, purity>98%). DE MALDI-TOF MS: $[M+H]^+$=3090.3 ($C_{143}H_{210}N_{36}O_{37}S_2$=3089.55).

4'-[Succinimidopropionoyl-(H-Cys-Arg-Gln-Ile-Lys-Ile-Trp-Phe-Gln-Asn-Arg-Arg-Met-Lys-Trp-Lys-Lys-OH)]etoposide (SEQ ID No. 27)

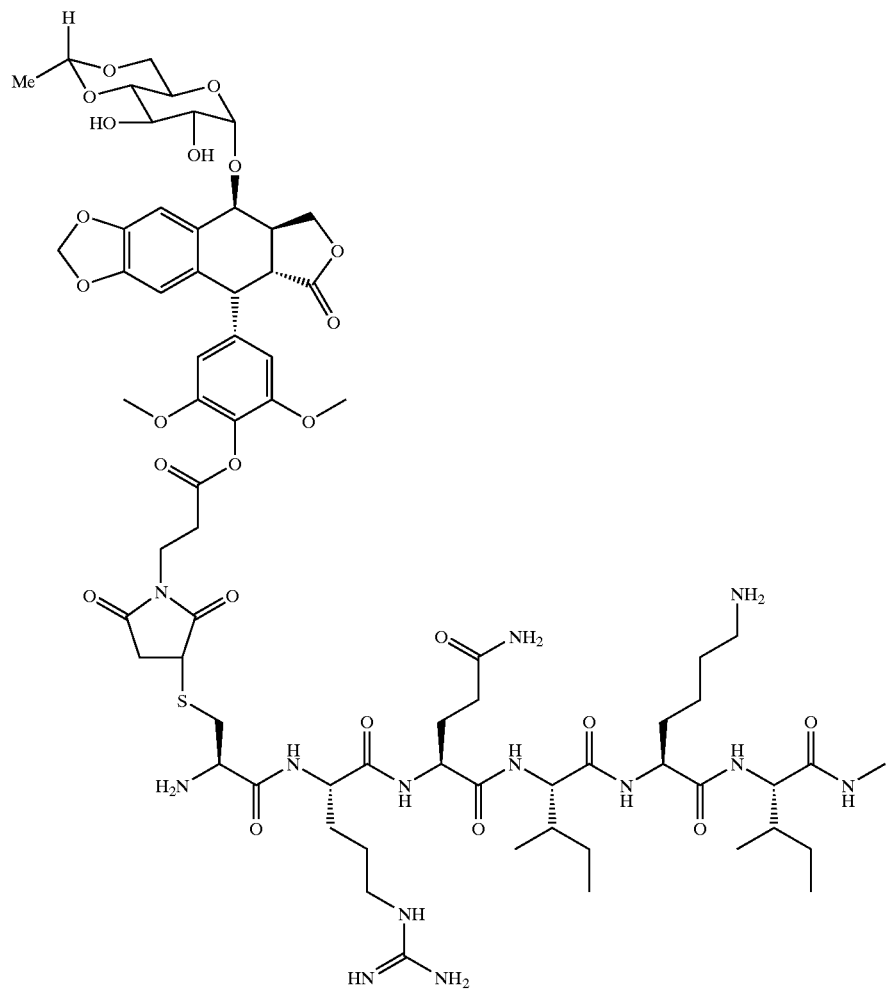

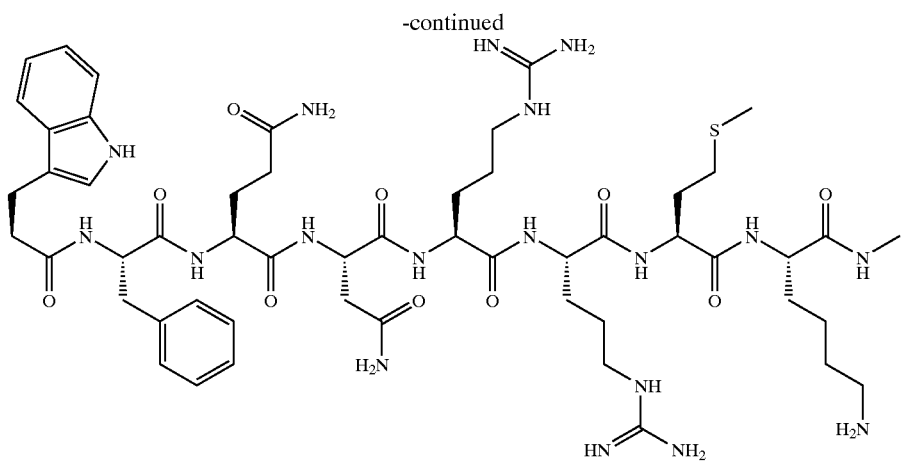
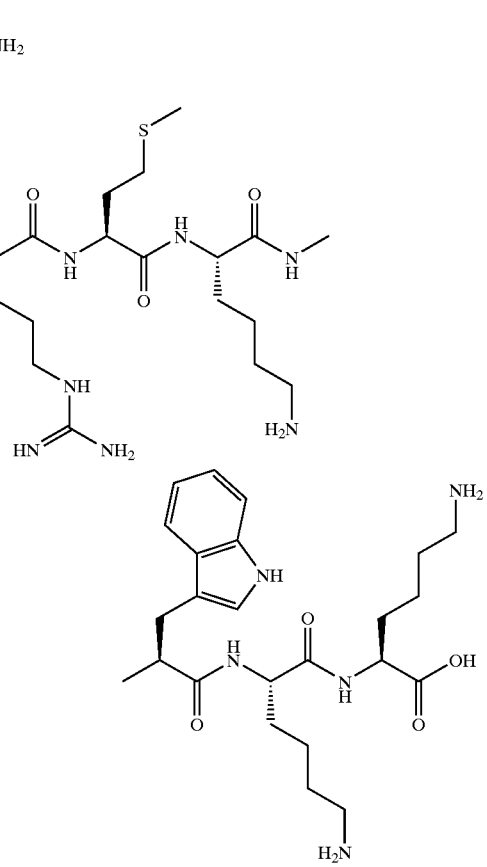

To a solution of 4'-(maleimidopropionoyl)etoposide (4.8 µmol, 3.6 mg) and H-Cys-Arg-Gln-Ile-Lys-Ile-Trp-Phe-Gln-Asn-Arg-Arg-Met-Lys-Trp-Lys-Lys-OH (SEQ ID No. 27) (5.9 µmol, 13.9 mg) in DMF (0.5 mL) was added Et$_3$N (0.7 µL, 5.1 µmol). The mixture was stirred for 30 min, diluted with 0.1% aq TFA (1 mL) and purified by preparative RP-HPLC (0–60% MeCN gradient) to afford the pure title compound as a colourless solid (11.2 mg, 77%). Anal. RP-HPLC: $t_R$=14.6 min (0–60% MeCN gradient, purity>99). DE MALDI-TOF MS: [M+H]$^+$=3090.9 ($C_{143}H_{210}N_{36}O_{37}S_2$=3089.55).

Example 21
O-(Maleimidoropionoyl)roscovitine

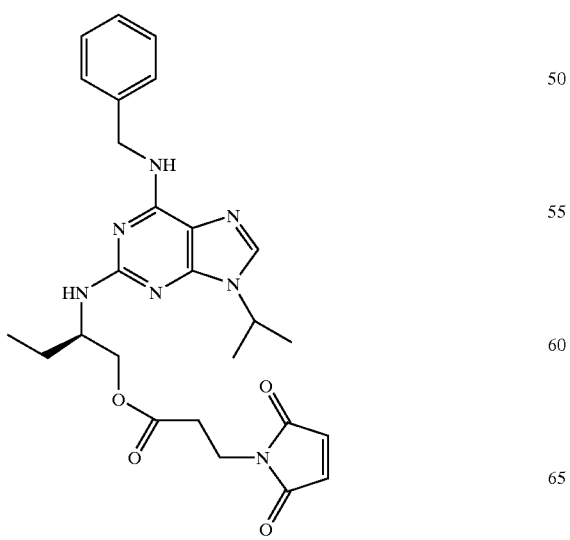

A solution of roscovitine (29 μmol, 10.3 mg), 3-maleimidopropionic acid (64 μmol, 10.8 mg), DIC (35 μmol, 4.4 mg) and DMAP (2 μmol, 0.35 mg) in of pyridine (1 mL) was stirred for 40 min. The solvent was evaporated in vacuo and the resulting light-yellow solid was redissolved in CH$_2$Cl$_2$, washed with water and brine and was dried on MgSO$_4$. The solvent was evaporated and the title compound was obtained as a light-yellow solid (14.1 mg, 96%). This material was used without further purification in the next reaction.

O-[Succinimidopropionoyl-(H-Cys-Arg-Gln-Ile-Lys-Ile-Trp-Phe-Gln-Asn-Arg-Arg-Met-Lys-Trp-Lys-Lys-OH)]roscovitine (SEQ ID No. 27)

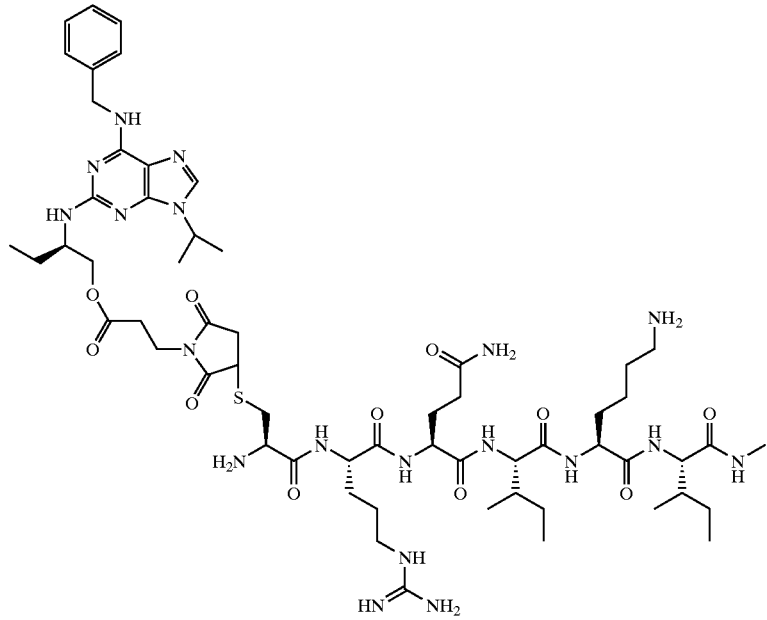

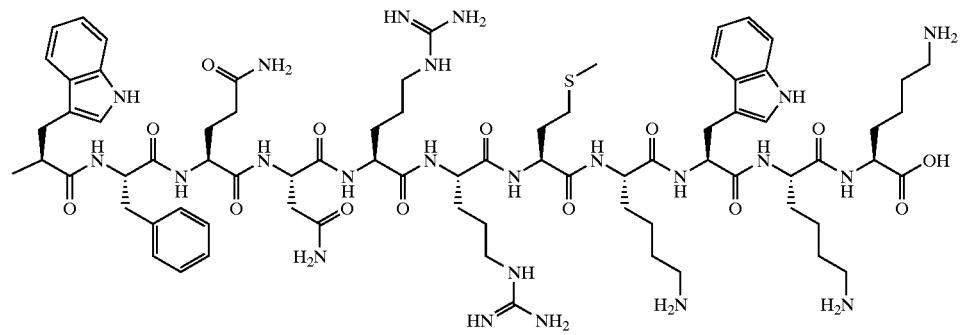

To a solution of O-(maleimidopropionoyl)roscovitine (28 μmol, 14.1 mg) and H-Cys-Arg-Gln-Ile-Lys-Ile-Trp-Phe-Gln-Asn-Arg-Arg-Met-Lys-Trp-Lys-Lys-OH (SEQ ID No. 27) (14.9 μmol, 35 mg) in DMF (1.5 mL) was added Et$_3$N (2 μL, 14.5 μmol). The mixture was stirred for 1 h and was purified by preparative RP-HPLC (10–60% MeCN gradient) to afford the pure title compound as a colourless solid (7.2 mg). Anal. RP-HPLC: t$_R$=15.5 min (0–60% MeCN gradient, purity>98%). DE MALDI-TOF MS: [M+H]$^+$=2856.1 (C$_{133}$H$_{204}$N$_{42}$O$_{25}$S$_2$=2855.44).

Example 22

O-βAla-Bohemine

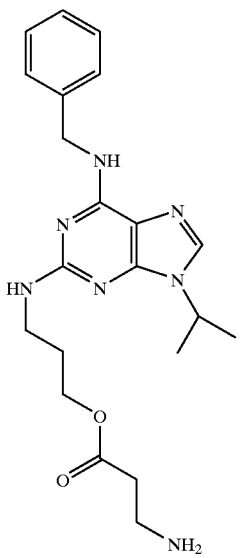

A solution of bohemine (58.8 μmol, 20 mg), Boc-βAla-OH (0.128 mmol, 24.2 mg) DIC (70 μmol, 8.8 mg) and DMAP (9.8 μmol, 1.2 mg) in CH$_2$Cl$_2$ (2 mL) was stirred for 2.5 hrs. The solvent was evaporated in vacuo and the resulting white solid was purified by preparative RP-HPLC (10–70% MeCN gradient) to afford O-(Boc-βAla)bohemine as a colourless solid (30 mg). Anal. RP-HPLC: t$_R$=19.8 min (0–60% MeCN gradient, purity>99%). A solution of O-(Boc-βAla)bohemine (7.6 mg) in 9:1 TFA/water (1 mL) was stirred for 1 h. The solvent was evaporated to dryness and the residue of title compound was used without further purification in the next reaction (purity by anal. RP-HPLC was >98%).

O-(βAla-succinyl-βAla-Arg-Gln-Ile-Lys-Ile-Trp-Phe-Gln-Asn-Arg-Arg-Met-Lys-Trp-Lys-Lys-OH) bohemine (SEQ ID No. 20)

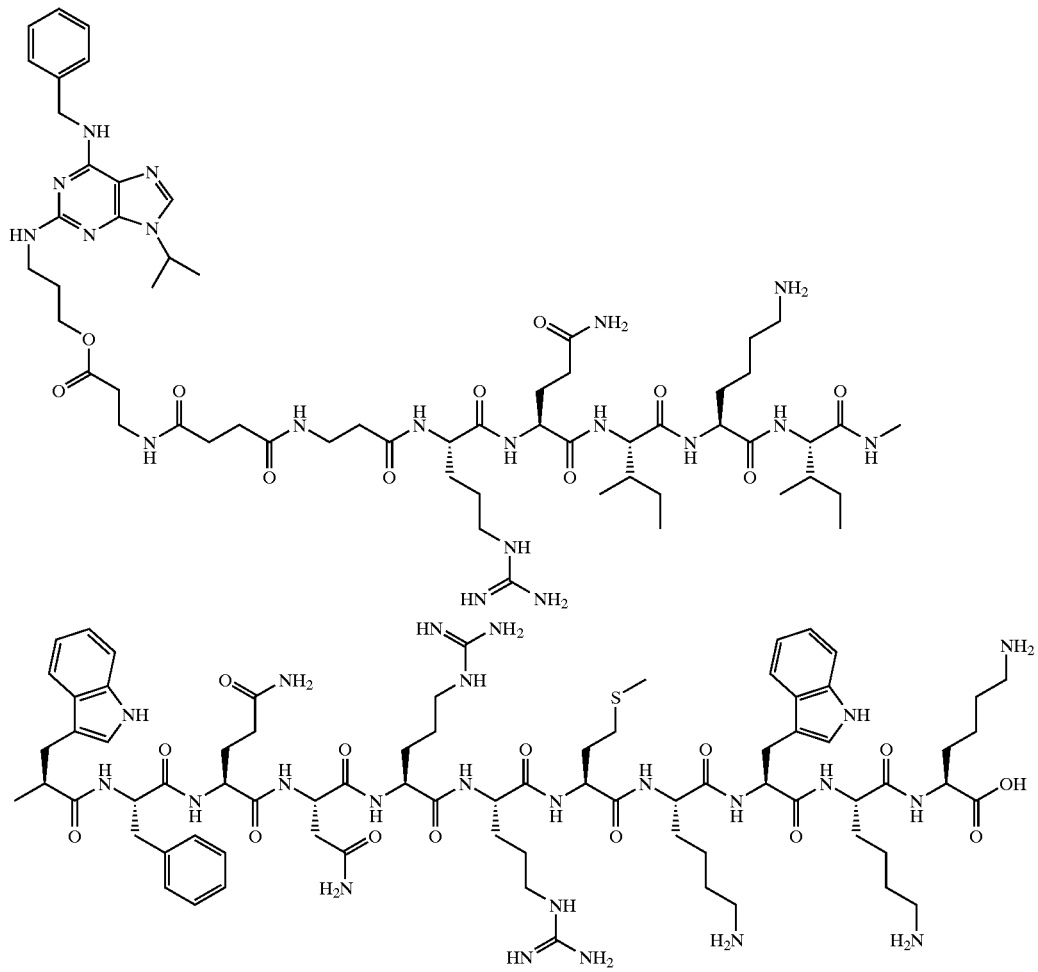

A mixture of succinyl-βAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-resin (SEQ ID No. 20) (14.9 μmol, 81.7 mg), O-βAla-bohemine (14.9 μmol, 7.6 mg), PyBOP (14.9 μmol, 7.8 mg), HOBt (14.9 μmol, 2.4 mg) and DIEA (0.2295 mmol, 29.7 mg) in DMF (2 mL) was stirred for 2 h. The peptidyl resin was filtered, washed with DMF, $CH_2Cl_2$ and $Et_2O$ and was dried in vacuo (82 mg). The product was treated with cleavage reagent (5 mL, 2 h). Crude product (42 mg) was obtained by precipitation with $Et_2O$ and centrifugation/decantation. It was purified by preparative RP-HPLC (0–60% MeCN gradient) to afford the pure title compound as a colourless solid (14.3 mg). Anal. RP-HPLC: $t_R$=14.8 min (0–60% MeCN gradient, purity>93%). DE MALDI-TOF MS: $[M+H]^+$=2812.7 ($C_{132}H_{204}N_{42}O_{25}S$=2811.37).

Example 23
(Maleimidopropionoyl)bohemine

3-Maleimidopropionic acid (12.8 mg, 76 μmol) was dissolved in $CH_2Cl_2$ (1 mL). The mixture was stirred and DIC (5.3 mg, 42 μmol) in dry $CH_2Cl_2$ (0.5 mL) was added. The reaction was allowed to proceed with stirring for 40 min. Solvent was then removed under reduced pressure. The residue of 3-maleimidopropionic acid anhydride was redissolved in dry pyridine (0.5 mL). A solution of bohemine (10.3 mg, 30 μmol) and DMAP (0.35 mg, 2 μmol) in pyridine (0.5 mL) was added and the mixture was stirred under $N_2$ for 1 h. It was then evaporated to dryness under reduced pressure. The residue was redissolved in DMF (1 mL) and purified by preparative RP-HPLC column (10–60% MeCN gradient) to afford the pure title compound as a colourless solid (14.7 mg, 88%). Anal. RP-HPLC: $t_R$=17.7 min (0–60% MeCN gradient, purity>95%). $^1$H-NMR ($CDCl_3$) and DE MALDI-TOF MS spectra were consistent with the proposed structure ($C_{25}H_{29}N_7O_4$=491.54).

O-[Succinimidopropionoyl-(H-Cys-Arg-Gln-Ile-Lys-Ile-Trp-Phe-Gln-Asn-Arg-Arg-Met-Lys-Trp-Lys-Lys-OH)]bohemine (SEQ ID No. 27)

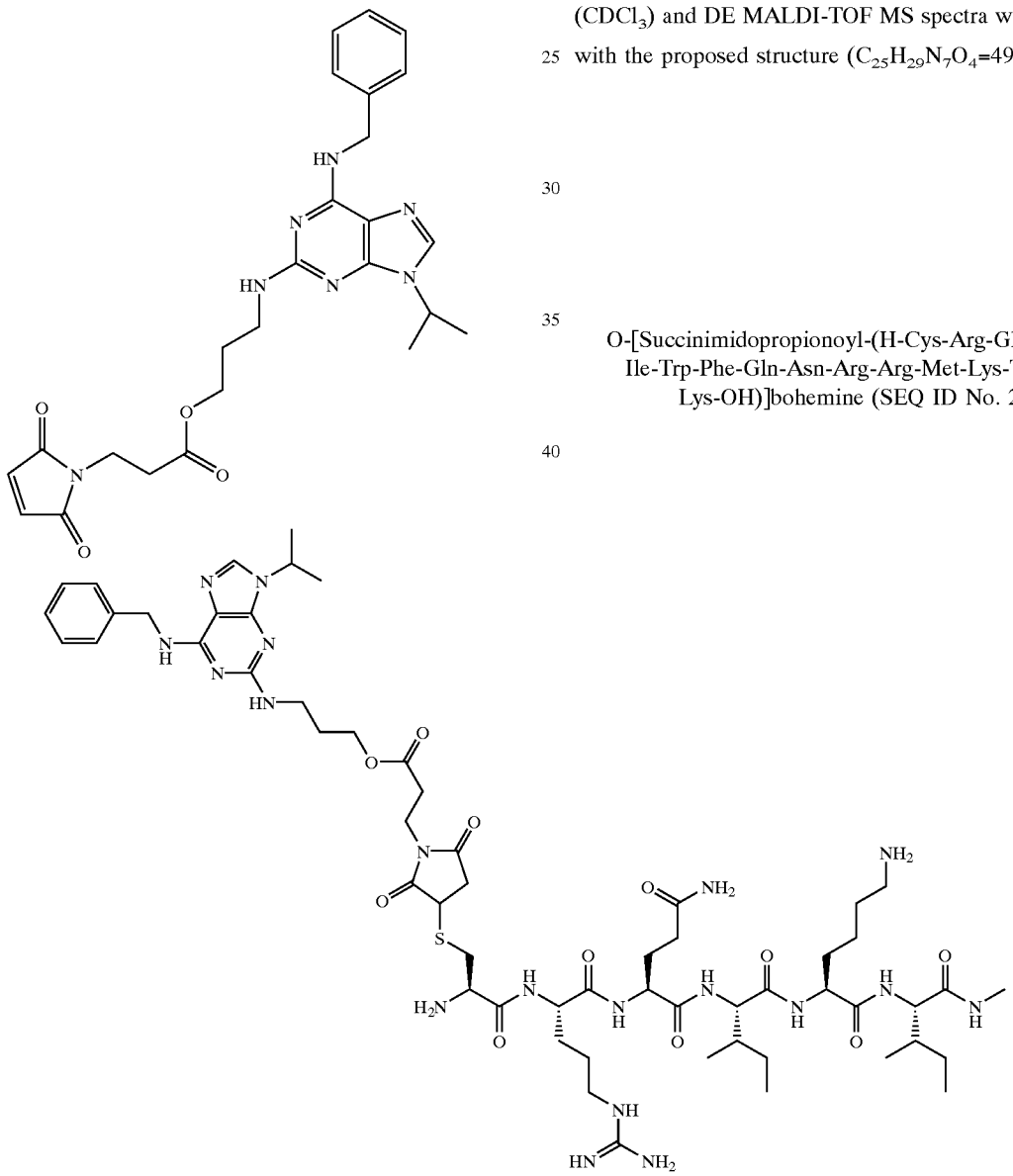

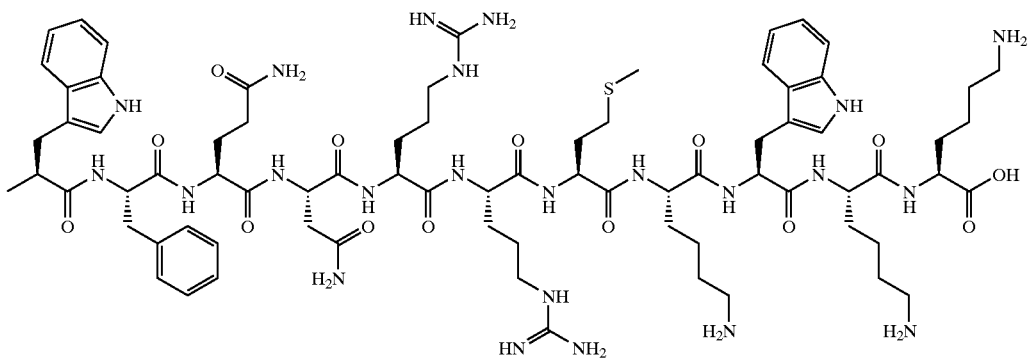

(Maleimidopropionoyl)bohemine (0.74 mg, 1.5 μmol) was dissolved in DMF (0.3 mL) and Et$_3$N (50 μL) was added. H-Cys-Arg-Gln-Ile-Lys-Ile-Trp-Phe-Gln-Asn-Arg-Arg-Met-Lys-Trp-Lys-Lys-OH (SEQ ID No. 27) (3.5 mg, 1.5 μmol), dissolved in DMF (0.25 mL) was then added. The mixture was stirred under N$_2$ and was monitored by anal. RP-HPLC. After 1 h, the reaction was complete. The mixture was filtered and purified by preparative RP-HPLC (10–60% MeCN gradient) to afford the pure title compound as a colourless solid (1.7 mg, 40%). Anal. RP-HPLC: t$_R$=15.0 min (0–60% MeCN gradient; purity>95%). DE MALDI-TOF MS: [M+H]$^+$=2842 (C$_{132}$H$_{202}$N$_{42}$O$_{25}$S$_2$= 2841.42).

Example 24
4-(Iodoacetyl)podophyllotoxin

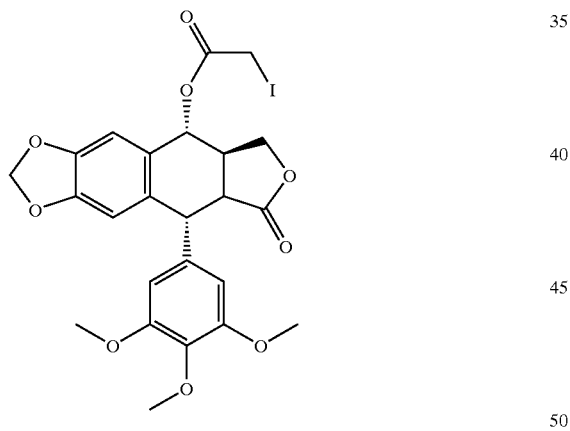

A mixture of podophyllotoxin (0.49 mmol, 204 mg), iodoacetic acid (1.03 mmol, 192 mg), DIC (0.552 mmol, 69.7 mg) and DMAP (0.164 mmol, 20 mg) in dry CH$_2$Cl$_2$ (5 mL) was cooled to 0° C. Pyridine (0.2 mL) was added and the reaction mixture was allowed to stir for 1 h at 0° C. The mixture was evaporated to dryness. The resulting light-yellow residue was redissolved in MeCN and was purified by preparative RP-HPLC (20–70% MeCN gradient) to afford the pure title compound as a colourless solid (89.5 mg). Anal. RP-HPLC: t$_R$=22.3 min (0–60% MeCN gradient, purity>95%). $^1$H-NMR (300 MHz, CDCl$_3$) δ: 2.85 (m, 2H, H2,3), 3.70 (s, 6H, OCH$_3$x2), 3.72 (s, 2H, CH$_2$I), 3.74 (s, 3H, OCH$_3$), 4.13 (m, 1H, H11), 4.34 (m, 1H, H11), 4.53 (d, 1H, J=3.60 Hz, H1), 5.83 (d, 1H, J=8.43 Hz, H4), 5.93 (dd, 2H, J=4.35, 1.17 Hz, OCH$_2$O)), 6.31 (s, 2H, H2'6'), 6.48 (s, 1H, H8), 6.77 (s, 1H, H5).

4-[Acetyl-(H-Cys-Arg-Gln-Ile-Lys-Ile-Trp-Phe-Gln-Asn-Arg-Arg-Met-Lys-Trp-Lys-Lys-OH)] podophyllotoxin (SEQ ID No. 27)

To a solution of 4-iodoacetyl)podophyllotoxin (17 μmol, 10 mg) and H-Cys-Arg-Gln-Ile-Lys-Ile-Trp-Phe-Gln-Asn-Arg-Arg-Met-Lys-Trp-Lys-Lys-OH (SEQ ID No. 27) (6 μmol, 14 mg) in DMF (1 mL) was added Et$_3$N (0.9 μL, 6 μmol). The mixture was stirred for 1 h. MeCN (0.5 mL) was added and the solution was purified by preparative RP-HPLC (10–60% MeCN gradient) to afford the pure title compound as a colourless solid (9.9 mg, 59%). Anal.

RP-HPLC: $t_R$=15.4 min (0–60% MeCN gradient, purity>97%). DE MALDI-TOF MS: [M+H]$^+$=2806.8 (C$_{131}$H$_{195}$N$_{35}$O$_{30}$S$_2$=2804.30).

Example 25

4-[Acetyl-(H-Cys-βAla-Arg-Arg-Met-Lys-Trp-Lys-Lys-NH$_2$)]podophyllotoxin (SEQ ID No. 19)

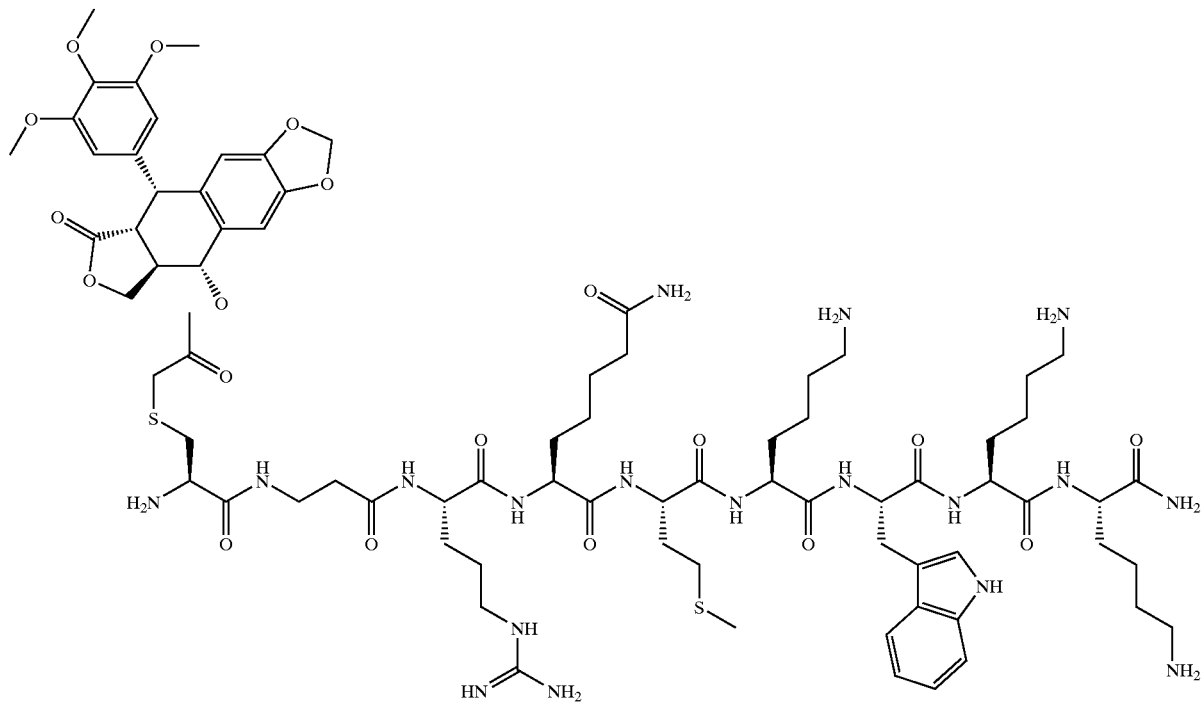

A solution of 4-(iodoacetyl)podophyllotoxin (17 μmol, 10 mg) and H-Cys-bAla-Arg-Arg-Met-Lys-Trp-Lys-Lys-NH$_2$ (SEQ ID No. 19) (23 μmol, 28.6 mg) in DMF (1 mL) was added Et$_3$N (2.4 μL, 17 μmol). After stirring for 1 h MeCN (0.5 mL) was added and the mixture was purified by preparative RP-HPLC (0–60% MeCN gradient) to afford the pure title compound as a colourless solid (29.4 mg, 100%). Anal. RP-HPLC: $t_R$=14.1 min (0–60% MeCN gradient, purity>98%). DE MALDI-TOF MS: [M+H]$^+$=1661.0 (C$_{76}$H$_{114}$N$_{20}$O$_{18}$S$_2$=1659.97).

Example 26

4'-Demethyl-4-(iodoacetyl)epipodophyllotoxin

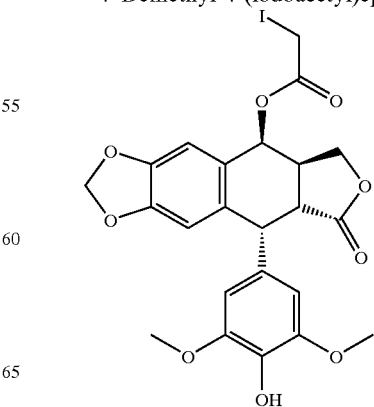

To a solution of 4'-demethylepipodophyllotoxin (0.26 mmol, 104 mg), iodoacetic acid (0.53 mmol, 98.8 mg), and DIC (0.32 mmol, 40.1 mg) in $CH_2Cl_2$ (2 mL) at 0° C. was added pyridine (50 µL) and DMAP (0.1 mmol, 12.8 mg). After 1 h stirring the solvents were evaporated. The residue was redissolved in DMF (1 mL) and purified by preparative RP-HPLC (20–60% MeCN gradient) to afford the pure title compound as a colourless solid (35.7 mg, 24%). Anal. RP-HPLC: $t_R$=20.3 min (0–60% MeCN gradient, purity>96%). $^1$H-NMR (300 MHz, $CDCl_3$) δ: 3.02 (m, 1H, H3), 3.20 (m, 1H, H2), 3.71 (s, 6H, $OCH_3$x2), 3.63 (s, 2H, $CH_2I$), 3.74 (s, 3H, $OCH_3$), 4.05 (m, 1H, H11), 4.27 (m, 1H, H11), 4.60 (d, 1H, J=4.94 Hz, H1), 6.06 (d, 1H, J=3.41 Hz, H4), 5.92 (m, 2H, $OCH_2O$), 6.21 (s, 2H, H2'6'), 6.49 (s, 1H, H8), 6.80 (s, 1H, H5).

4'-Demethyl-4-[acetyl-(H-Cys-βAla-Arg-Arg-Met-Lys-Trp-Lys-Lys-$NH_2$)]epipodophyllotoxin (SEQ ID No. 19)

To a solution of 4'-demethyl-4-(iodoacetyl) epipodophyllotoxin (17.6 µvvmol, 10 mg) and H-Cys-βvAla-Arg-Arg-Met-Lys-Trp-Lys-Lys-$NH_2$ (SEQ ID No. 19) (14.9 µmol, 18 mg) in DMF (1 mL) was added $Et_3N$ (2.1 mL, 15 µmol). After stirring for 1 h the reaction mixture was purified by preparative RP-HPLC (0–60% MeCN gradient) to afford the pure title compound as a colourless solid (11.2 mg, 46%). Anal. RP-HPLC: $t_R$=12.8 min (0–60% MeCN gradient, purity>98%). DE MALDI-TOF MS: $[M+H]^+$= 1647.2 ($C_{75}H_{112}N_{20}O_{18}S_2$=1645.95).

Example 27

4'-Demethyl-4-[acetyl-(H-Cys-Arg-Gln-Ile-Lys-Ile-Trp-Phe-Gln-Asn-Arg-Arg-Met-Lys-Trp-Lys-Lys-NH$_2$)]epipodophyllotoxin (SEQ ID No. 27)

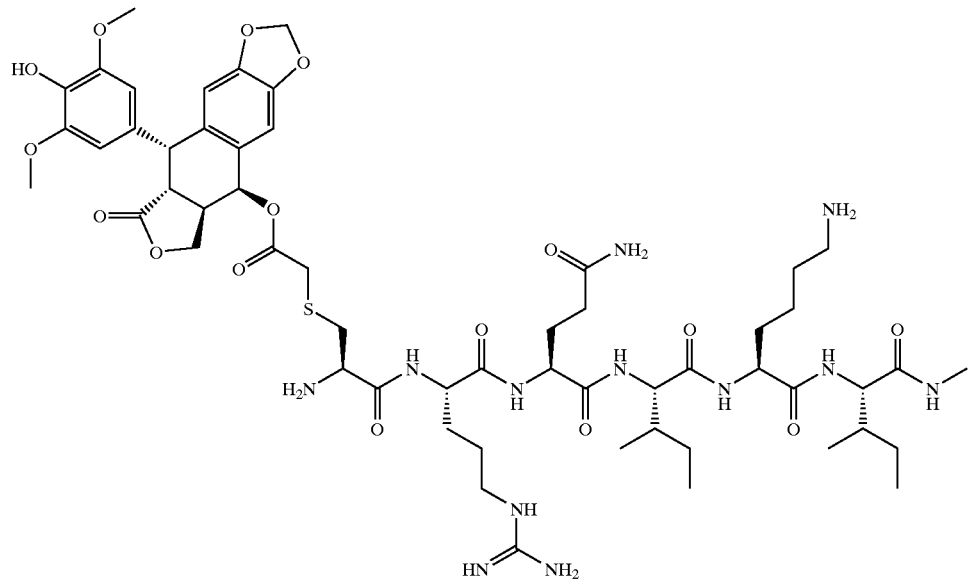

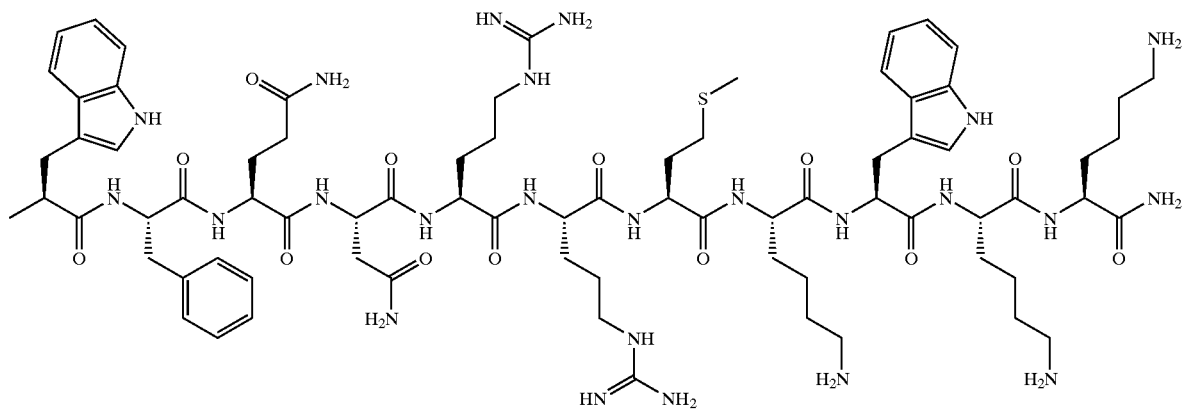

To a solution of 4'-demethyl-4(iodoacetyl)epipodophyllotoxin (22 μmol, 12.6 mg) and H-Cys-Arg-Gln-Ile-Lys-Ile-Trp-Phe-Gln-Asn-Arg-Arg-Met-Lys-Trp-Lys-Lys-NH$_2$ (SEQ ID No 27) (8 μmol, 20 mg) in DMF (1 mL) was added Et$_3$N (1.2 μL, 9 μmol). After stirring for 1 h the mixture was purified by preparative RP-HPLC (0–60% MeCN gradient) to afford the pure title compound as a colourless solid (13.3 mg, 56%). Anal. RP-HPLC: $t_R$=14.5 min (0–60% MeCN gradient, purity>96%). DE MALDI-TOF MS: [M+H]$^+$=2789.5 ($C_{130}H_{194}N_{36}O_{29}S_2$=2789.29).

Example 28

4-(Boc-Gly)podophyllotoxin

A mixture of podophyllotoxin (400 mg, 0.97 mmol), Boc-Gly-OH (510 mg, 2.91 mmol) DIC (1.73 mmol, 273 μL), DMAP (0.41 mmol, 50 mg) and pyridine (173 μL) in $CH_2Cl_2$ (5 mL) was stirred at for 1 h. The solvents were evaporated. The residue was redissolved in DMF (1.5 mL) and purified by RP-HPLC (20–70% MeCN gradient) to afford the pure title compound as a colourless solid (502.6 mg, 91%). Anal. RP-HPLC: $t_R$=22.1 min (0–60% MeCN gradient, purity>97%).

4-(H-Gly)podophyllotoxin

To a solution of 4-(Boc-Gly)podophyllotoxin (0.24 mmol, 137 mg) in $CH_2Cl_2$ (8 mL) was added TFA (0.5 mL). After stirring for 1 h the solvents were evaporated. The resulting light-yellow solid residue was purified by preparative RP-HPLC (10–70% MeCN gradient) to afford the pure title compound as a colourless solid (41.7 mg, 37%). Anal. RP-HPLC: $t_R$=15.2 min (0–60% MeCN gradient, purity>97%).

4-Maleimidopropionoyl-Gly)podophyllotoxin

To a solution of 3-maleimidopropionic acid (70 μmol, 11.8 mg) and DIC (38 μmol, 4.83 mg) in DMF (1 mL) was added 4-(H-Gly)podophyllotoxin (17 μmol, 8 mg), DMAP (10 μmol, 1.2 mg) and pyridine (20 μL). After stirring for 1 h the mixture was purified by preparative RP-HPLC (0–60% MeCN gradient) to afford the pure title compound as a colourless solid (1.1 mg). Anal. RP-HPLC: $t_R$=18.2 min (0–60% MeCN gradient, purity>97%).

4-[(Succinimidopropionoyl-Gly)-(H-Cys-bAla-Arg-Arg-Met-Lys-Trp-Lys-Lys-$NH_2$)]podophyllotoxin
(SEQ ID No. 19)

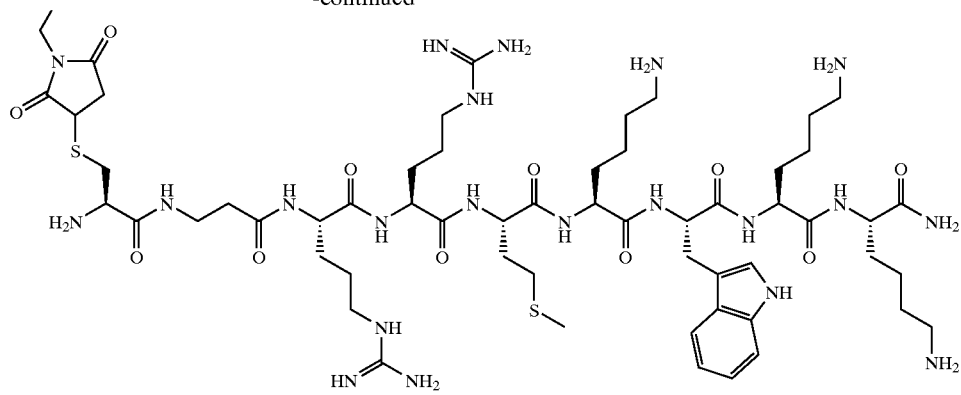

To a solution of 4-(maleimidopropionoyl-Gly) podophyllotoxin (1.8 μmol, 1.1 mg) and H-Cys-βAla-Arg-Arg-Met-Lys-Trp-Lys-Lys-NH₂ (SEQ ID No. 19) (4 μmol, 5 mg) in DMF (1 mL) was added Et₃N (0.5 μL, 4 μmol). The mixture was stirred for 1 h. It was diluted with MeCN (0.5 mL) and purified by preparative RP-HPLC (0–60% MeCN gradient) to afford the title compound as a colourless solid (1.1 mg, 33%). Anal. RP-HPLC: $t_R$=14.7 min (0–60% MeCN gradient, purity>97%). DE MALDI-TOF MS: [M+H]=1829.8 ($C_{83}H_{122}N_{22}O_{21}S_2$=1828.12).

Example 29

10-O-(Maleimidopropionoyl)camptothecin

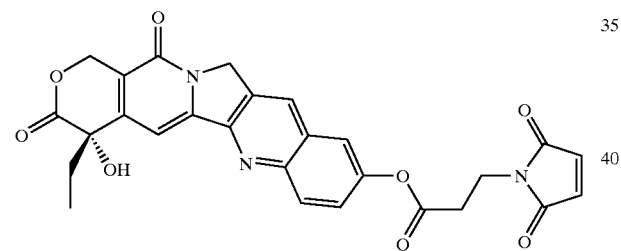

To a solution of 10-hydroxycamptothecin (40 μmol, 14.7 mg), 3-maleimidopropionic acid (0.228 mmol, 38.5 mg) and DIC (0.125 mmol, 15.8 mg) in CH₂Cl₂ (2 mL) was added pyridine (0.2 mL). After stirring for 1 h, the mixture was evaporated to dryness. The resulting light-yellow solid was redissolved in DMF (1 mL) and purified by preparative RP-HPLC (10–70% MeCN gradient) to afford the pure title compound (9.2 mg, 45%) as a light-yellow solid. Anal. RP-HPLC: $t_R$=15.7 min (0–60% MeCN gradient, purity>97%). ¹H-NMR (300 MHz, CDCl₃) δ: 1.05 (t, 3H, J=7.5 Hz, CH₃), 1.91 (m, 2H, J=7.8 Hz, CH₂), 2.98 (t, 2H, J=7.8 Hz, CH₂), 4.04 (t, 2H, J=7.8 Hz, CH₂), 5.32 (m, 3H, H5, H17), 6.77 (s, 2H, CH=CH), 7.60 (m, 1H, H11), 7.72 (m, 2H, H14, H9), 8.24 (d, 1H, J=9.2 Hz, H12), 8.36 (s, 1H, H7).

10-O-[Succinimidopropionoyl-(H-Cys-Arg-Gln-Ile-Lys-Ile-Trp-Phe-Gln-Asn-Arg-Arg-Met-Lys-Trp-Lys-Lys-NH₂)]camptothecin (SEQ ID No. 27)

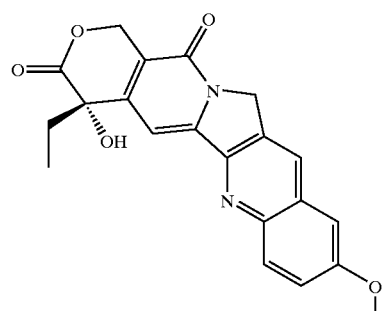

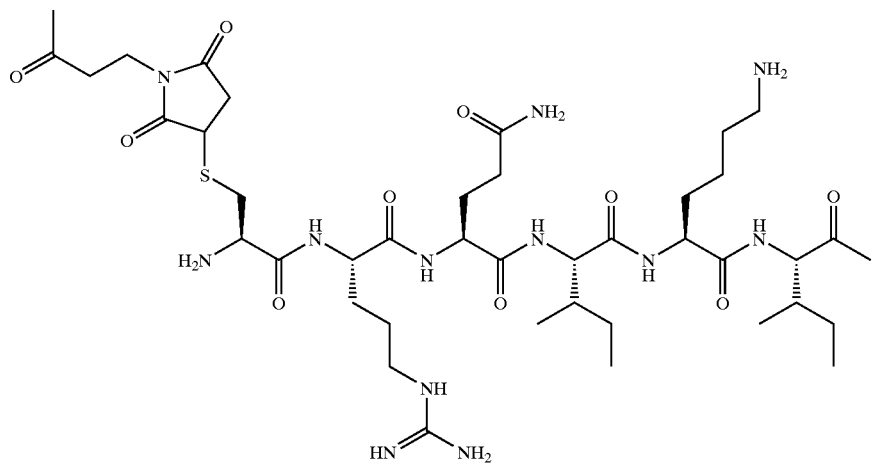
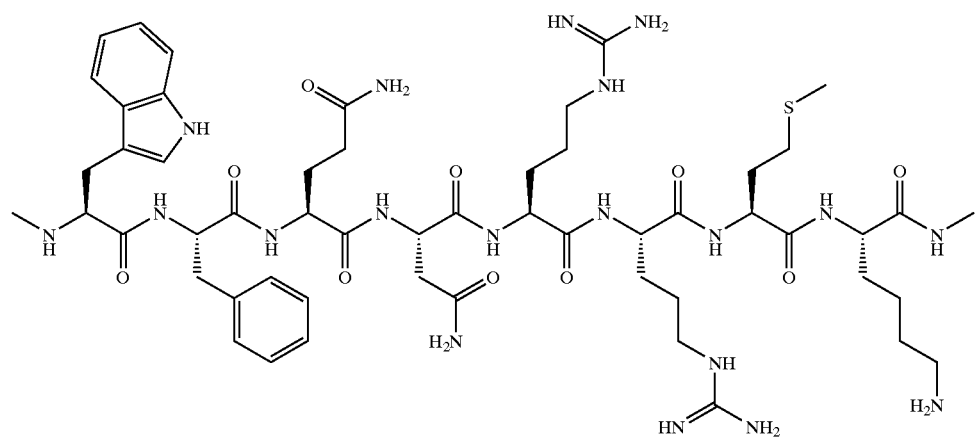
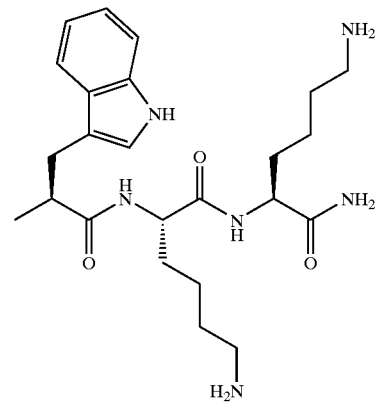

To a solution of 10-O-(maleimidopropionoyl) camptothecin (9 μmol, 4.6 mg) and H-Cys-Arg-Gln-Ile-Lys-Ile-Trp-Phe-Gln-Asn-Arg-Arg-Met-Lys-Trp-Lys-Lys-NH$_2$ (SEQ ID No. 27) (4 μmol, 10 mg) in DMF (1 mL) was added Et$_3$N (0.55 μL, 4 μmol). After stirring for 1 h, the mixture was purified by preparative RP-HPLC (0–60% MeCN gradient) to afford the pure title compound as a colourless solid (6.5 mg, 57%). Anal. RP-HPLC: t$_R$=14.0 min (0–60% MeCN gradient, purity>98%). DE MALDI-TOF MS: [M+H]$^+$=2864.7 (C$_{134}$H$_{195}$N$_{39}$O$_{28}$S$_2$=2864.36).

Example 30

H-Cys-Arg-Arg-Met-Lys-Trp-Lys-Lys-Cys-NH$_2$
(SEQ ID No. 21)

Starting from Rink Amide AM resin (0.69 mmol/g, Novabiochem), H-Cys(Trt)-Arg(Pmc)-Arg(Pmc)-Met-Lys (Boc)-Trp-Lys(Boc)-Lys(Boc)-Cys(Trt)-resin (SEQ ID No. 21) was assembled. After deprotection (1.5 h), the crude peptide was obtained by precipitation from Et$_2$O, centrifugation/decantation, and drying. Aliquots (total 258 mg) were purified by preparative RP-HPLC (9–19% MeCN gradient) to afford the pure title compound (132.4 mg). Anal. RP-HPLC: t$_R$=20.3 min (8–18% MeCN gradient, purity>99%, λ=214 nm). DE MALDI-TOF MS: [M+H]$^+$=1238.6 (C$_{52}$H$_{92}$N$_{20}$O$_9$S$_3$=1237.63).

Bis-[4-(succinimidopropionoyl)podophyllotoxin]-
(H-Cys-Arg-Arg-Met-Lys-Trp-Lys-Lys-Cys-NH$_2$)
(SEQ ID No. 21)

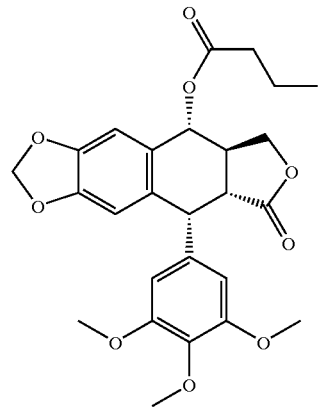

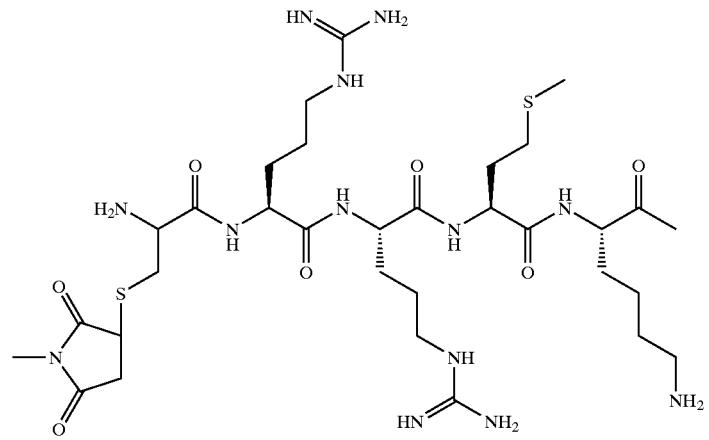

-continued

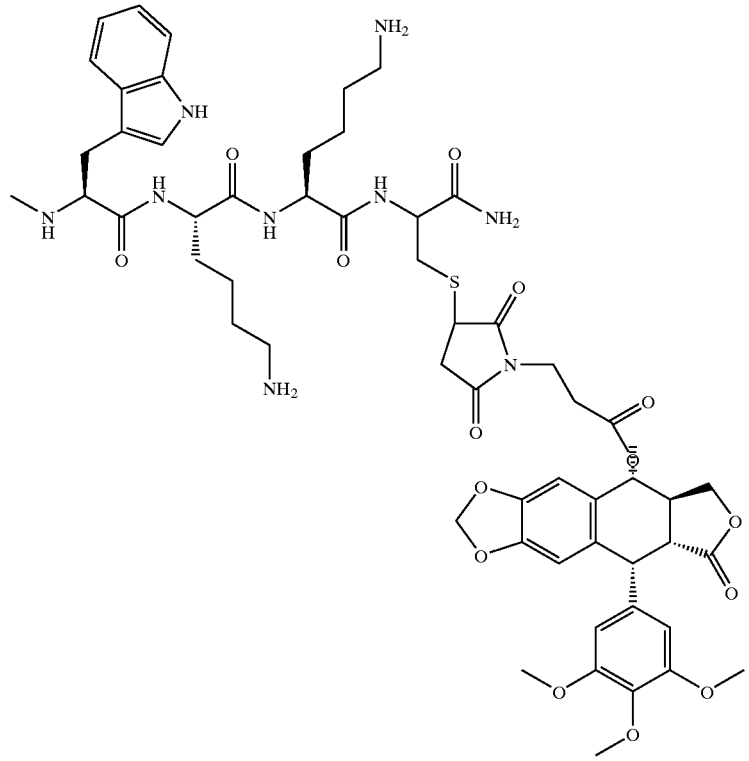

To a solution of 4-(maleimidopropionoyl)podophyllotoxin (19 μmol, 11 mg) and H-Cys-Arg-Arg-Met-Lys-Trp-Lys-Lys-Cys-NH$_2$ (SEQ ID No. 21) (12 μmol, 15 mg), in DMF (1 mL) was added Et$_3$N (2.8 μL). After stirring for 1 h the mixture was purified by preparative RP-HPLC (10–70% MeCN gradient) to afford the pure title compound as a colourless solid (9.0 mg, 32%). Anal. RP-HPLC: t$_R$=17.4 min (0–60% MeCN gradient, purity>98%). DE MALDI-TOF MS: [M+H]$^+$=2369.7 (C$_{110}$H$_{146}$N$_{22}$O$_{31}$S$_3$=2368.66).

Example 31

4'-(Succinimidopropionoyl)epipodophyllotoxin-(H-Cys-Arg-Arg-Met-Lys-Trp-Lys-Lys-Cys-NH$_2$)-10-O-(succinimidopropionoyl)camptothecin (SEQ ID No. 21)

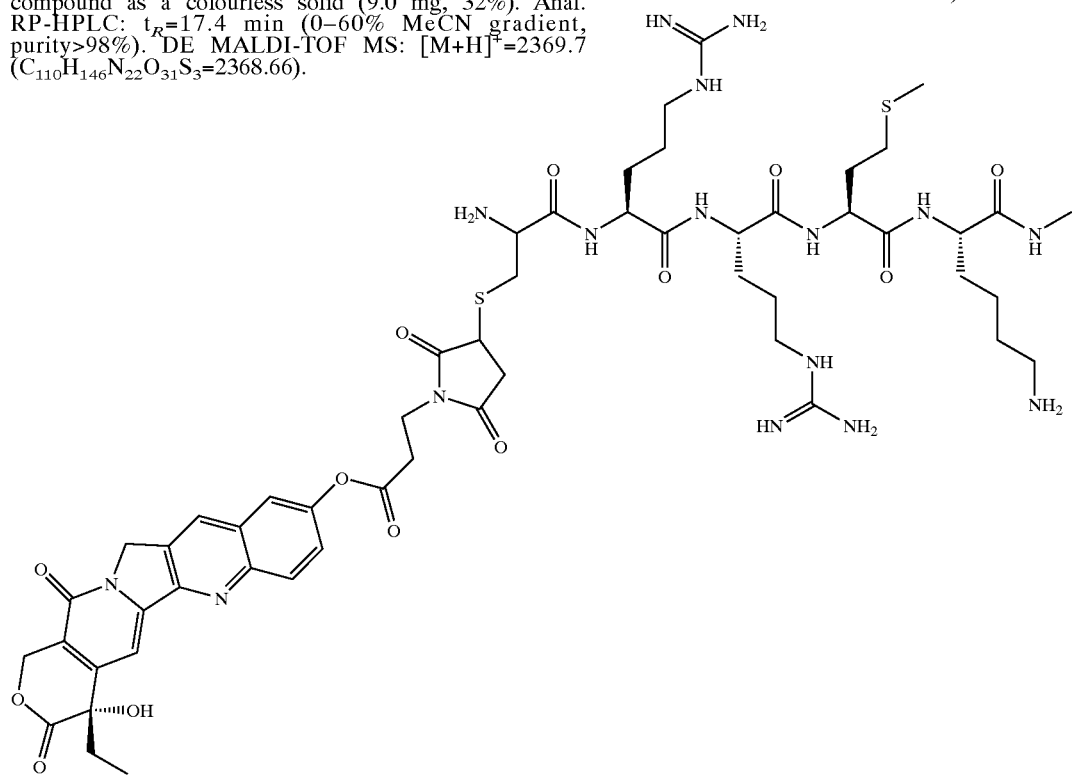

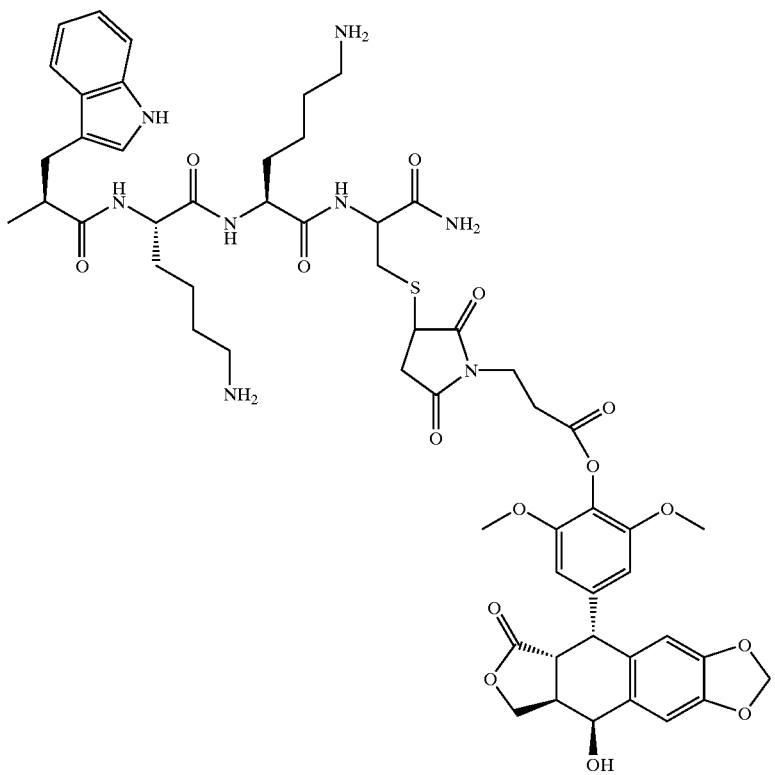

To a solution of 10-O-(maleimidopropionoyl) camptothecin (0.005 mmol, 2.6 mg), 4'-(maleimidopropionoyl)epipodophyllotoxin (5.6 μmol, 3.1 mg), and H-Cys-Arg-Arg-Met-Lys-Trp-Lys-Lys-Cys-NH$_2$ (SEQ ID No. 21) (11 μmol, 13 mg), in DMF (1.5 mL) was added Et$_3$N (1.5 μL). After stirring for 1.5 h the mixture was purified by preparative RP-HPLC (10–70% MeCN gradient) to afford the pure title compound as a colourless solid (1.9 mg). Anal. RP-HPLC: $t_R$=14.8 min (0–60% MeCN gradient, purity>96%). DE MALDI-TOF MS: [M+H]$^+$=2304.6 ($C_{107}H_{138}N_{24}O_{28}S_3$=2304.58).

Example 32
4'-(Succinimidopropionoyl)epipodophyllotoxin-(H-Cys-Arg-Arg-Met-Lys-Trp-Lys-Lys-Cys-NH$_2$)-2'-(succinimidopropionyl)paclitaxel (SEQ ID No. 21)
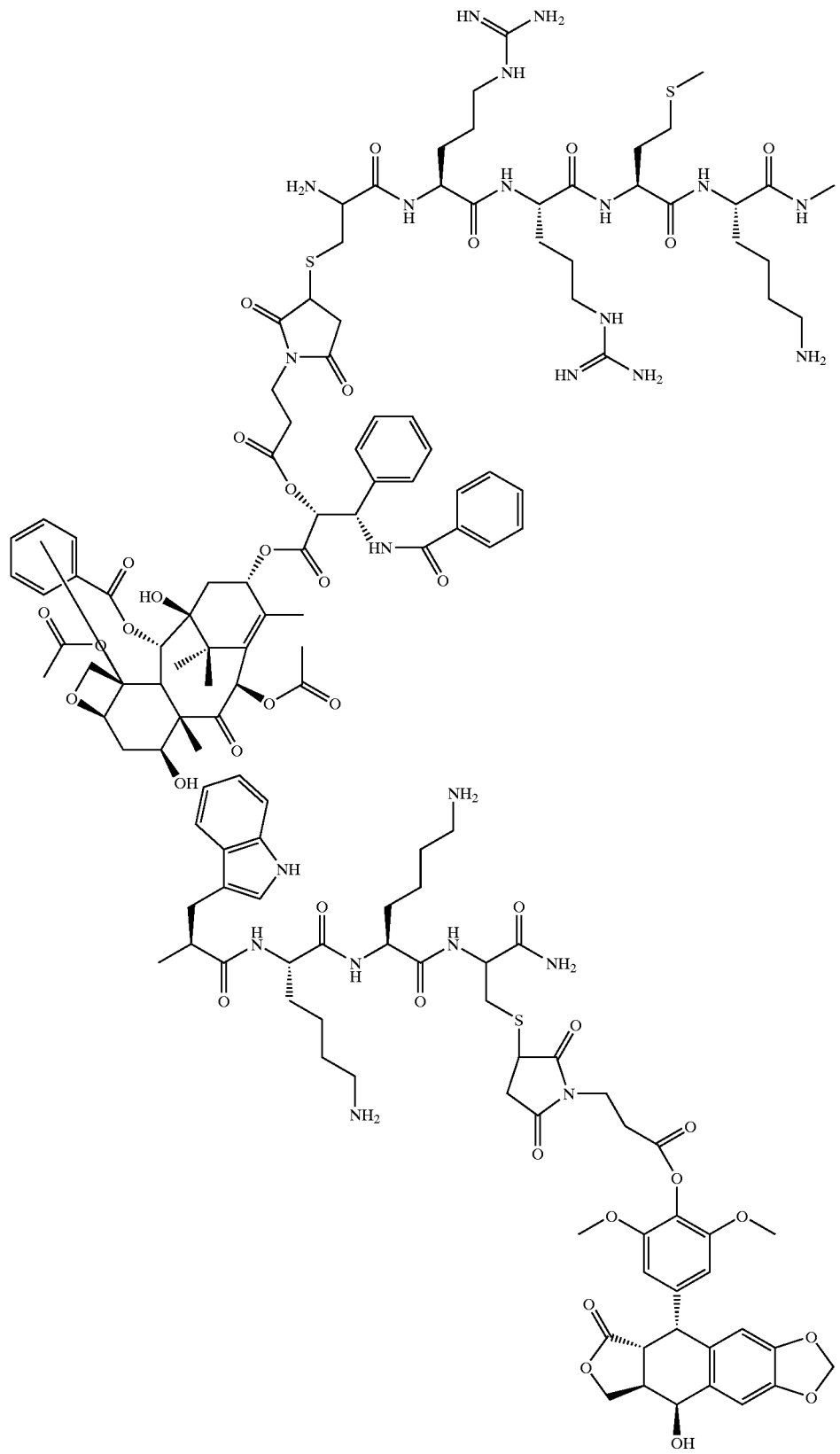

To a solution of 4'-[succinimidopropionoyl-(H-Cys-Arg-Arg-Met-Lys-Trp-Lys-Lys-Cys-NH$_2$)]epipodo-phyllotoxin (SEQ ID No. 21) (2 μmol, 3.5 mg), 2'-(maleimidopropionyl) paclitaxel (2 μmol, 2 mg) in DMF (1 mL) was added Et$_3$N (0.3 μL). After stirring for 1.5 h the reaction mixture was purified by preparative RP-HPLC (10–70% MeCN gradient) to afford the pure title compound as a colourless solid (1.5 mg). Anal. RP-HPLC: $t_R$=17.8 min (0–60% MeCN gradient, purity>98%). DE MALDI-TOF MS: [M+H]$^+$=2794.5 (C$_{134}$H$_{173}$N$_{23}$O$_{37}$S$_3$=2794.14).

Example 33

4'-Methoxy-(4"-aminoanilino)epipodophyllotoxin and 4'-demethyl-(4"-aminoanilino) epipodophyllotoxin A solution of podophyllotoxin (3.6 mmol, 1.5 g) in ClCH$_2$CH$_2$Cl (15 mL) was kept at 0° C. and HBr gas was passed through the solution. After 45 min N$_2$ was passed through the reaction mixture to drive off excess HBr. To this solution anhydrous barium carbonate (4.32 mmol, 0.85 g) and 4-nitroaniline (4.32 mmol, 0.6 g) were added. The mixture was stirred at ambient temperature for 18 h under N$_2$. It was diluted with EtOAc and filtered. The filtrate was washed with water, dried on MgSO$_4$, and purified by flash, chromatograph (100:5:5 CH$_2$Cl$_2$/EtOAc/acetone) to afford crude 4'-methoxy-(4"-nitroanilino)epipodophyllotoxin and 4'-demethyl-(4"-nitroanilino)epipodophyllotoxin. Further purification by preparative RP-HPLC (10–70% MeCN gradient) afforded the pure products as yellow solids.

4'-Methoxy-4-(4"-nitroanilino)epipodophyllotoxin

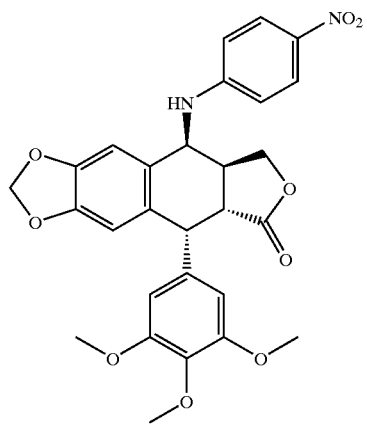

Anal. RP-HPLC: $t_R$=22.3 min (0–60% MeCN gradient, purity>95%). $^1$H-NMR (300 MHz, CDCl$_3$) δ: 3.09 (m, 2H, H2,3), 3.77 (s, 6H, OCH$_3$), 3.83 (s, 3H, OCH$_3$), 3.86 (m, 1H, H11), 4.42 (m, 1H, H11), 4.63 (m, 2H, H1,4), 4.84 (m, 1H, NH), 6.00 (m, 2H, OCH$_2$O), 6.31 (s, 2H, H2',6'), 6.57 (m, 3H, H8, Ar), 6.76 (s, 1H, H5), 8.16 (d, 2H, J=9.08 Hz, Ar).

4'-Demethyl-4-(4"-nitroanilino)epipodophyllotoxin

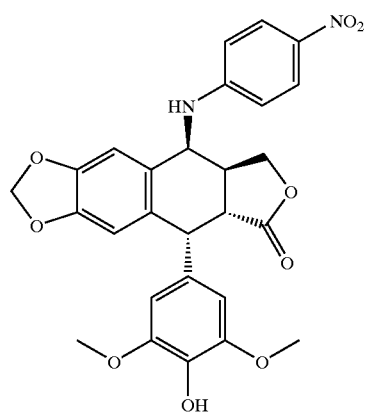

Anal. RP-HPLC for: $t_R$=20.5 min (0–60% MeCN gradient, purity>95%). $^1$H-NMR (300 MHz, CDCl$_3$) δ: 3.07 (m, 2H, H2,3), 3.79 (s, 6H, OCH$_3$), 3.81 (m, 1H, H11), 4.40 (m, 1H, H11), 4.60 (m, 2H, H1), 4.73 (m, 1H, H4), 4.83 (m, 1H, NH), 5.45 (br, 1H, OH), 5.98 (m, 2H, OCH$_2$O), 6.31 (s, 2H, H2',6'), 6.57 (m, 3H, H8, Ar), 6.76 (s, 1H, H5), 8.14 (d, 2H, J=9.04 Hz, Ar).

To a solution of 4'-methoxy-4-(4"-nitroanilino) epipodophyllotoxin or 4'-demethyl-(4"-nitroanilino) epipodophyllotoxin in 10:1 EtOAc/MeOH was added 10% palladium on activated carbon. The mixture was stirred under H$_2$ for 3 h. The catalyst was filtered and washed several times with MeOH. The combined filtrate and washing were evaporated to dryness to give a light-yellow solid which was redissolved in MeCN and purified by preparative RP-HPLC (10–70% MeCN gradient) to afford the products as yellow solids in a quantitative yield.

4'-Methoxy-4-(4"-aminoanilino)epipodophyllotoxin

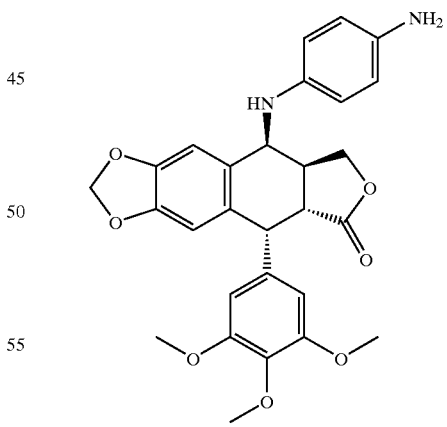

Anal. RP-HPLC: $t_R$=16.1 min (0–60% MeCN gradient, purity>95%). $^1$H-NMR (300 MHz, CDCl$_3$) δ: 287 (m, 1H, H3), 3.11 9m, 1H, H2), 3.68 (s, 6H, OCH$_3$), 3.73 (s, 3H, OCH$_3$), 3.61 (m, 1H, H11), 4.15 (m, 1H, H11), 4.52–4.62 (m, 2H, H1,4), 5.86 (m, 2H, OCH$_2$O), 6.28 (s, 2H, H2',6'), 6.37 (m, 2H, Ar), 6.45 (s, 1H, H8), 6.69 (s, 1H, H5), 7.03 (m, 2H, Ar).

4'-Demethyl-4-(4"-aminoanilino)epipodophyllotoxin

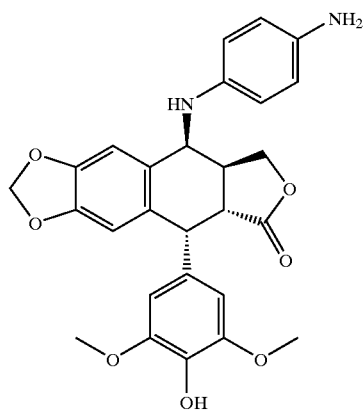

Anal. RP-HPLC: $t_R$=14.2 min (0–60% MeCN gradient, purity>97%). $^1$H-NMR (300 MHz, CDCl$_3$) δ: 3.05 (m, 1H, H3), 3.18 (m, 1H, H2), 3.78 (s, 6H, OCH$_3$), 3.93 (m, 1H, H11), 4.38 (m, 1H, H11), 4.60 (d, 1H, J=5.91 Hz, H1), 4.70 (d, 1H, J=3.86 Hz, H4), 5.96 (m, 2H, OCH$_2$O), 6.33 (s, 2H, H2'6'), 6.53 (s, 1H, H8), 6.62 (d, 2H, J=8.66 Hz, Ar), 6.75 (s, 1H, H5), 7.19 (d, 2H, J=8.60 Hz, Ar).

4'-Methoxy-4-[4"-aminoanilino-maleimidopropionoyl)]epipodophyllotoxin

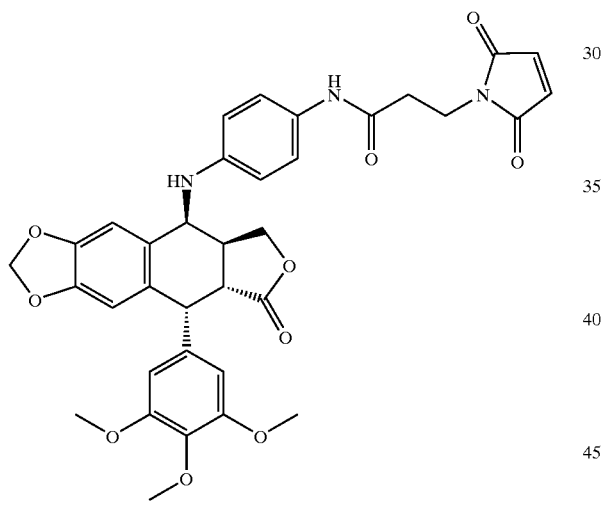

To a solution of 4'-methoxy-4-(4"-aminoanilino)epipodophyllotoxin (41 μmol, 20.8 mg), 3-maleimidopropionic acid (0.226 mmol, 38.2 mg), DIC (0.124 mmol, 15.7 mg) and DMAP (40 μmol, 4.9 mg) in CH$_2$Cl$_2$ (2 mL) was added pyridine (0.2 mL). After stirring for 1 h, the mixture was evaporated to dryness. The resulting light-yellow solid was redissolved in DMF (1 mL) and purified by preparative RP-HPLC (20–70% MeCN gradient) to afford the pure title compound as a colourless solid (10.1 mg, 38%). Anal. RP-HPLC: $t_R$=19.5 min (0–60% MeCN gradient, purity>96%). $^1$H-NMR (300 MHz, CDCl$_3$) δ: 2.71 (t, 2H, J=7.0 Hz, CH$_2$), 2.91 (m, 1H, H3), 3.14 (m, 1H, H2), 3.76 (s, 6H, OCH$_3$), 3.82 (s, 3H, OCH$_3$), 3.93 (t, 2H, J=7.0 Hz, CH$_2$), 3.97 (m, 1H, H5, H11), 3.49 (m, 1H, H11, 4.63 (m, 2H, H1,4), 5.97 (m, 2H, OCH$_2$O), 6.32 (s, 2H, H2'6'), 6.50 (m, 2H, Ar), 6.53 (s, 1H, H8), 6.73 (s, 2H, CH=CH), 6.74 (s, 1H, H5), 7.32 (m, 2H, Ar).

4'-Methoxy-4-[4"-aminoanilino-(succinimidopropionoyl)-(H-Cys-Arg-Gln-Ile-Lys-Ile-Trp-Phe-Gln-Asn-Arg-Arg-Met-Lys-Trp-Lys-Lys-NH$_2$)]epipodophyllotoxin (SEQ ID No. 27)

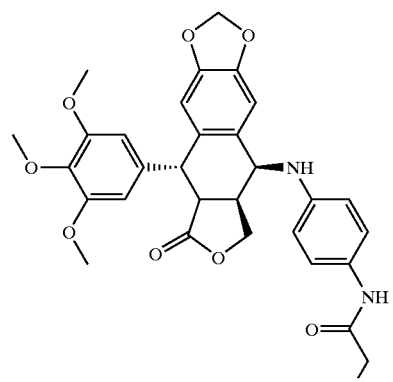

-continued

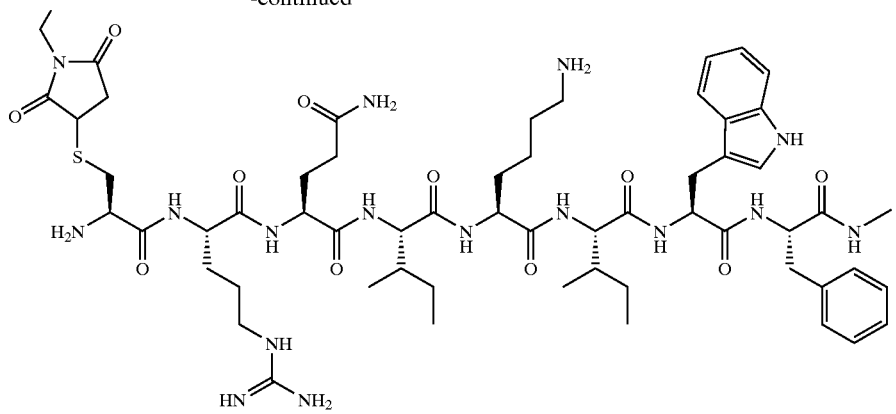

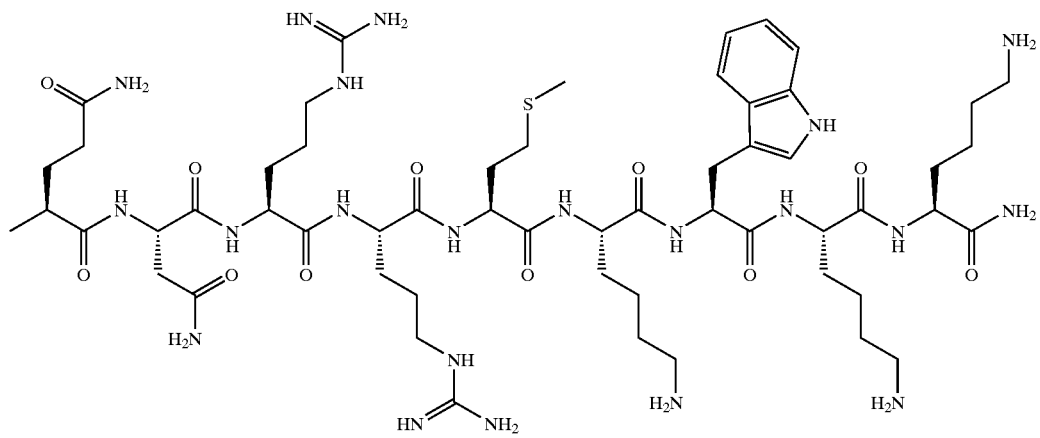

To a solution of 4'-methoxy-4-[4"-aminoanilino-(maleimidopropionoyl)]epipodophyllotoxin, (6 μmol, 4.1 mg) and H-Cys-Arg-Gln-Ile-Lys-Ile-Trp-Phe-Gln-Asn-Arg-Arg-Met-Lys-Trp-Lys-Lys-NH₂ (SEQ ID No. 27) (6 μmol, 14 mg) in DMF (1 mL) was added Et₃N (2 μL). After stirring for 1 h, the mixture was purified by preparative RP-HPLC (0–60% MeCN gradient) to afford the pure title compound as a colourless solid (5.8 mg, 32%). Anal. RP-HPLC:

$t_R$=16.0 min (0–60% MeCN, purity>99%). DE MALDI-TOF MS: [M+H]⁺=3003.9 ($C_{142}H_{207}N_{39}O_{30}S_2$=3004.54).

Example 34

4'-Methoxy-4-[4"-aminoanilino-(succinimidopropionoyl)-(H-Cys-βAla-Arg-Arg-Met-Lys-Trp-Lys-Lys-NH₂)]epipodophyllotoxin (SEQ ID No. 19)

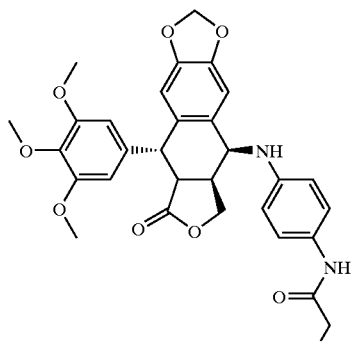

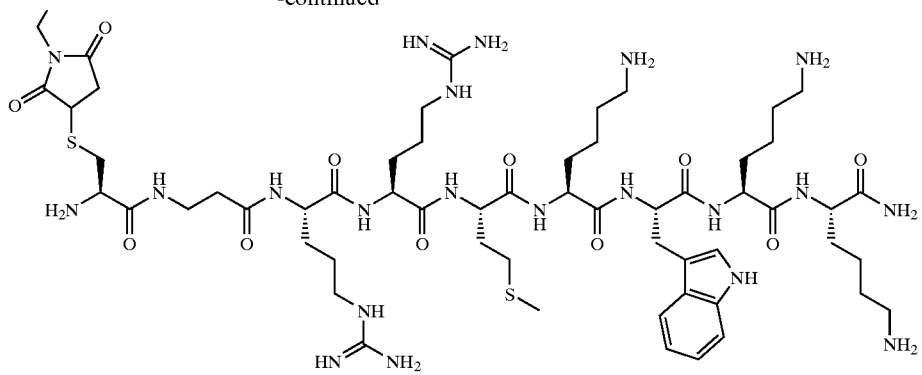

To a solution of 4'-methoxy-[4"-aminoanilino-(maleimidopropionoyl)]epipodophyllotoxin (7 μmol, 4.6 mg) and H-Cys-βAla-Arg-Arg-Met-Lys-Trp-Lys-Lys-NH₂ (SEQ ID No. 19) (14 μmol, 16.3 mg) in DMF (1 μL) was added Et₃N (1 mL). After stirring for 1 h, the mixture was purified by preparative RP-HPLC (0–60% MeCN gradient) to afford the pure title compound as a colourless solid (6.4 mg, 49%). Anal. RP-HPLC: $t_R$=15.2 min (0–60% MeCN gradient, purity>98%). DE MALDI-TOF MS: [M+H⁺= 1861.6 ($C_{87}H_{125}N_{23}O_{19}S_2$=1861.20).

Example 35

4'-Demethyl-4-[4"-aminoanilino-(maleimidopropionoyl)]epipodophyllotoxin

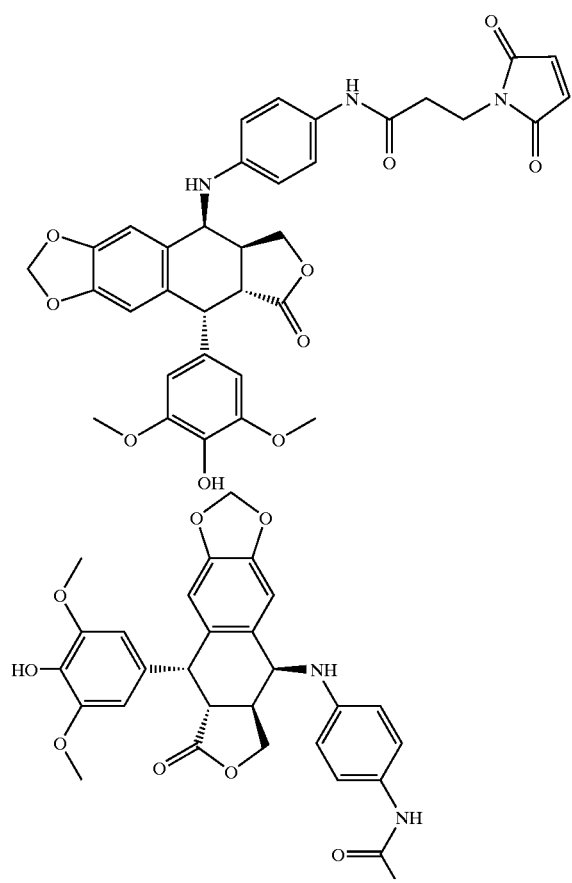

To a solution of 4'-demethyl-4-(4"-aminoanilino) epipodophyllotoxin (24 μmol, 12 mg), 3-maleimidopropionic acid (49 μmol, 8.3 mg), and DIC (27 μmol, 3.4 mg) in 1:1 DMF/CH₂Cl₂ (2 mL) was added pyridine (10 μL). After stirring for 1 h, the reaction mixture was evaporated. The resulting light-yellow solid was purified by preparative RP-HPLC (10–70% MeCN gradient) to afford the pure title compound as a colourless solid (5.3 mg, 34%). Anal. RP-HPLC: $t_R$=19.5 min (0–60% MeCN gradient, purity>96%). ¹H-NMR (300 MHz, CDCl₃) δ: 2.65 (t, 2H, J=7.3 Hz, CH₂), 2.98 (m, 1H, H3), 3.17 (m, 1H, H2), 3.79 (s, 6H, OCH₃), 3.93 (t, 2H, J=7.0 Hz, CH₂), 3.99 (m, 1H, H5, H11), 4.38 (m, 1H, H11), 4.58 (d, 1H, J=4.95 Hz, H1), 4.64 (d, 1H, J=3.95 Hz, H4) 5.96 (m, 2H, OCH₂O), 6.33 (s, 2H, H2'6'), 6.49–6.53 (m, 3H, H8, Ar), 6.74 (s, 2H, CH=CH), 6.75 (s, 1H, H5), 7.33 (m, 2H, Ar).

4'-Demethyl-4-[4"-aminoanilino-(succinimidopropionoyl)-(H-Cys-βAla-Arg-Arg-Met-Lys-Trp-Lys-Lys-NH₂)]epipodophyllotoxin
(SEQ ID No. 19)

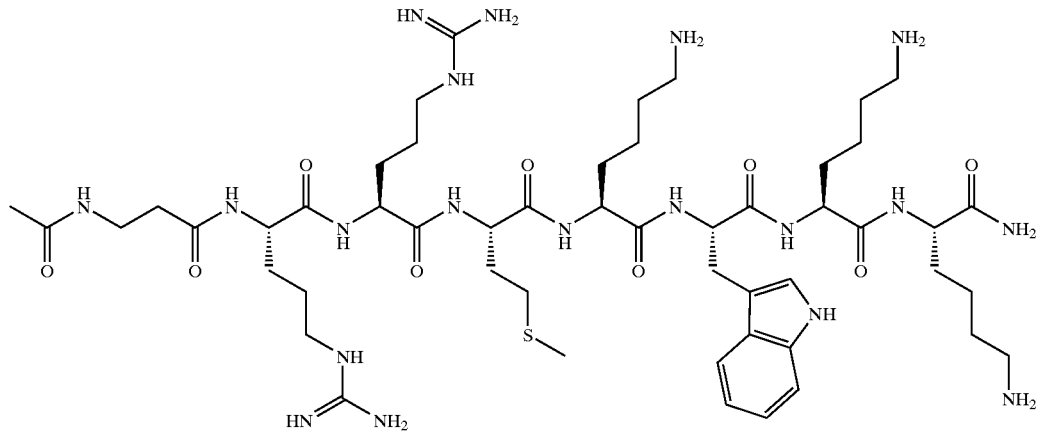

To a solution of 4'-demethyl-[4"-aminoanilino-(maleimidopropionoyl)]epipodophyllotoxin (8.3 μmol, 5.3 mg) and H-Cys-βAla-Arg-Arg-Met-Lys-Trp-Lys-Lys-NH2 (SEQ ID No. 19) (13 μmol, 15.6 mg) in DMF (1.5 mL) was added Et$_3$N (2 μL). After stirring for 1 h, the mixture was purified by preparative RP-HPLC (0–60% MeCN gradient) to afford the pure title compound as a colourless solid (14.9 mg, 97%). Anal. RP-HPLC: t$_R$=13.7 min (0–60% MeCN gradient, purity>98%). DE MALDI-TOF MS: [M+H]$^+$= 1847.1 ($C_{86}H_{123}N_{23}O_{19}S_2$=1847.17).

Example 36

In vitro cytotoxic activity of {[4[N-(2,4-diamino-6-pteridinyl-methyl)-N-methylamino]benzoyl]-Glu-Gly-βAla}$_4$-Lys$_2$-Lys-βAla-Arg-Gln-Ile-Lys-Ile-Trp-Phe-Gln-Asn-Arg-Arg-Met-Lys-Trp-Lys-Lys-OH (SEQ ID No. 28)

This compound (abbreviated 'MTX-Pen' in the tables below) was evaluated for its ability to inhibit cell proliferation of normal (immortalised) human cells (HaCaT cells, Tables 1 & 2) and a human colorectal cancer cell line (HT29, Table 3). The free drug methotrexate ('MTX' in Table 1–3) and the free vector H-Ala-Arg-Gln-Ile-Lys-Ile-Trp-Phe-Gln-Asn-Arg-Arg-Met-Lys-Trp-Lys-Lys-OH (abbreviated 'Pen' in Table 1 below) were included for the purposes of comparison.

Assay procedure—Cells were seeded into 96-well plates at 2,500 cells/well in DMEM with 10% FCS and antibiotics. After overnight incubation, test compound dilutions in cell medium were prepared and were added to the cells. Samples were taken 1, 2, 3, and 4 days after compound addition. Nucleotide Releasing Reagent (LumiTech ViaLight kit) was added in order to lyse the cells and release ATP. After incubation at room temperature (5 min), the mixtures were transferred to opaque 96-well plates and stored at −20° C. until analysis. After loading plates into a luminometer (Lucy 1, Labtech International), ATP Monitoring Reagent (20 μL/well, LumiTech ViaLight kit) was added to each well successively and light intensity was measured immediately. Six readings were taken per sample. Each assay point was established using six replicates and appropriate controls. ATP bioluminescence was found to be proportional to viable cell count over the entire cells/well range used. Statistically significant results in the tables below are printed in bold face.

TABLE 1

(HaCaT Cells)

| | % Cell Death | | | | | | | | | | | |
|---|---|---|---|---|---|---|---|---|---|---|---|---|
| | Day 1 | | | Day 2 | | | Day 3 | | | Day 4 | | |
| Dose (μM) | MTX | MTX-Pen | Pen | MTX | MTX-Pen | Pen | MTX | MTX-Pen | Pen | MTX | MTX-Pen | Pen |
| 40.0 | 4 | 29 | 16 | 15 | 82 | −22 | 79 | 97 | 5 | 92 | 98 | 12 |
| 13.3 | 22 | −42 | 18 | 35 | 63 | 0 | 82 | 97 | −17 | 92 | 98 | −6 |

TABLE 1-continued (HaCaT Cells)

% Cell Death

| Dose (μM) | Day 1 | | | Day 2 | | | Day 3 | | | Day 4 | | |
|---|---|---|---|---|---|---|---|---|---|---|---|---|
| | MTX | MTX-Pen | Pen | MTX | MTX-Pen | Pen | MTX | MTX-Pen | Pen | MTX | MTX-Pen | Pen |
| 4.4 | 4 | −8 | 8 | 24 | 45 | −4 | 77 | 95 | −1 | 93 | 98 | 10 |
| 1.5 | 13 | −24 | 16 | 31 | 82 | −31 | 77 | 82 | 2 | 94 | 88 | −14 |
| 0.5 | −4 | −19 | 6 | 31 | 2 | −6 | 75 | 29 | −29 | 93 | 49 | −26 |
| 0.2 | 7 | 14 | 26 | 11 | 21 | 0 | 79 | 20 | −3 | 93 | 51 | 21 |

TABLE 2

(HaCaT Cells)

% Cell Death

| Dose (μM) | Day 1 | | Day 2 | | Day 3 | | Day 4 | |
|---|---|---|---|---|---|---|---|---|
| | MTX | MTX-Pen | MTX | MTX-Pen | MTX | MTX-Pen | MTX | MTX-Pen |
| 40.0 | | 42 | | 88 | | 95 | | 94 |
| 13.3 | | 27 | | 87 | | 95 | | 94 |
| 4.4 | 21 | 15 | 70 | 52 | 97 | 95 | 92 | 88 |
| 1.5 | 14 | 19 | 67 | 12 | 96 | −16 | 91 | 17 |
| 0.5 | 0 | 13 | 59 | 24 | 96 | −27 | 91 | 2 |
| 0.2 | 3 | | | 41 | | 94 | | 86 |
| 0.1 | 19 | | 7 | | 45 | | 65 | |

TABLE 3

(HT 29 Cells)

% Cell Death

| Dose (μM) | Day 1 | | Day 2 | | Day 3 | | Day 4 | |
|---|---|---|---|---|---|---|---|---|
| | MTX | MTX-Pen | MTX | MTX-Pen | MTX | MTX-Pen | MTX | MTX-Pen |
| 40.0 | | 31 | | 79 | | 96 | | 98 |
| 13.3 | | 3 | | 45 | | 88 | | 96 |
| 4.4 | −14 | 10 | −4 | 6 | 58 | 46 | 86 | 77 |
| 1.5 | 17 | 16 | −5 | 9 | 48 | 15 | 84 | 45 |
| 0.5 | 15 | 14 | −12 | 8 | 52 | 17 | 88 | 16 |
| 0.2 | 10 | | −5 | | 54 | | 85 | |
| 0.1 | 6 | | −17 | | 52 | | 84 | |

Example 37

Stabilisation of microtubule formation by paclitaxel and 2'-[Succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27)

Assay procedure.—A solution of bovine tubulin and tetramethylrhodamine-labeled tubulin (total concentration 0.5 mg/mL) in G-PEM buffer (80 mM PIPES, pH 6.8, 1 mM EDTA, 1 mM GTP) was incubated in the presence of 10 μM paclitaxel, 10 μM 2'-[succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27), or without test compound for 30 min at 37° C. Formation of microtubules was visualised on a Nikon Eclipse E800 fluorescence microscope. Images were captured with a Kodak DCS 420 digital camera and analysed using Adobe 5.0 software. Microtuble formation was stabilized using the delivery systems of the present invention.

Example 38

Internalisation of 4-[succinimidopropionoyl-(biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$)]podophyllotoxin (SEQ ID No. 18) into cells A549 cells were seeded into 96-well plates at 50,000 cells per well in DMEM with 10% FCS and antibiotics. After overnight incubation, 4-[succinimidopropionoyl-(biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$)]podophyllotoxin (SEQ ID No. 18) (labelled 'conjugate' in FIG. 1 below) or biotinamidocaproyl-Arg-Gln-Ile-Lys-Ile-Trp-Phe-Gln-Asn-Arg-Arg-Met-Lys-Trp-Lys-Lys-Gly-Cys-Gly-NH$_2$ (SEQ ID No. 23) (labelled 'vector') were prepared as a dilution series of six decreasing concentrations in cell medium and were added to cells. At the end of the incubation period (60 min), the cells were rinsed three times with PBS and fixed for 20 min at −20° C. in ethanol/acetic acid (95/5). After the fixation, the cell were permeabilised for 10 min with PBS containing 3% Tween-20. Endogenous alkaline phosphatase was neutralised by incubating the plate at 65° C. for 60 min. Cells were incubated for 30 min at room temperature with alkaline phosphatase-streptavidine (Pierce Chemical Co.) in 0.1% BSA in PBS and were washed extensively with PBS. A freshly made solution of 1 mg/mL nitrophenyl phosphate in 10 mM diethanolamine (pH 9.5), 0.5 mM MgCl$_2$ was added to each well and incubated until sufficient colour developed (approximately 30 min). The enzymatic reaction was stopped by adding 50 μl 2 M aq NaOH. Alkaline phosphatase activity was measured spectrophotometrically at 405 nm.

Example 39

Visualisation of cell internalisation by 4-[Succinimidopropionoyl-(biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$)] podophyllotoxin (SEQ ID No. 18)

Cells were seeded into 8-well chamber slides at 50,000 cells per well in DMEM with 10% foetal calf serum and antibiotics. After overnight incubation, 4-[(Succinimidopropionoyl-(biotinamidocaproyl-βAla-Arg-Gln-Ile-Lys-Ile-Trp-Phe-Gln-Asn-Arg-Arg-Met-Lys-Trp-Lys-Lys-Gly-Cys-Gly-NH$_2$)]podophyllotoxin (SEQ ID No. 18) was prepared in cell medium at a concentration of 10 μM and was added to cells. At the end of the incubation period (60 min), the cells were rinsed three times with PBS and fixed for 20 min at −20° C. in ethanol/acetic acid (95/5). After the fixation, the cells were permeabilised for 10 min with PBS containing 3% Tween-20. The slides were incubated with streptavidin-FITC (Pierce Chemical Co.), diluted in PBS for 30 min. at room temperature, washed extensively with PBS and mounted in Hydromount (BDH). The distribution of the fluorescence was analysed on a Nikon Eclipse E800 fluorescence microscope. Images were captured with a Kodak DCS 420 digital camera and analysed using Adobe 5.0 software. Using these techniques, the internalization of a delivery system of the present invention can be monitored.

Example 40

Intracellular stability of 4-[succinimidopropionoyl-(H-Cys-Arg-Gln-Ile-Lys-Ile-Trp-Phe-Gln-Asn-Arg-Arg-Met-Lys-Trp-Lys-Lys-NH$_2$)]podophyllotoxin (SEQ ID No. 27)

Figure 2:
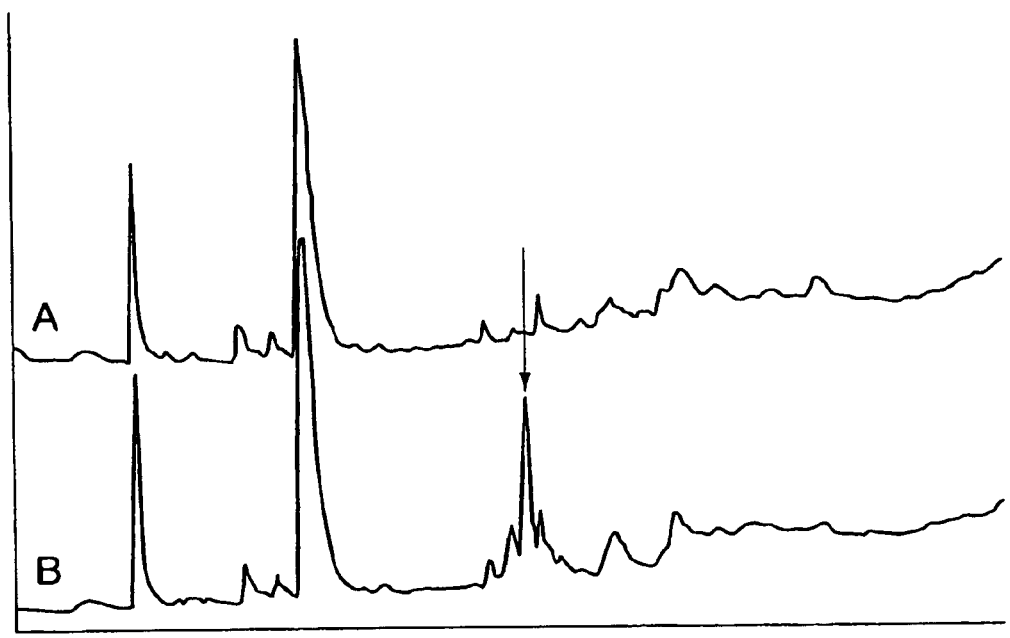
FIG. 2 shows the intracellular stability of a delivery system of the present invention.

10×10$^6$ HL60 cells were incubated for 1 h with 15 μM 4-[succinimidopropionoyl-(H-Cys-Arg-Gln-Ile-Lys-Ile-Trp-Phe-Gln-Asn-Arg-Arg-Met-Lys-Trp-Lys-Lys-NH$_2$)] podophyllotoxin (SEQ ID No. 27) (A in FIG. 2 below) or without test compound (B) in DMEM. After the incubation, cells were washed extensively with PBS until no test compound was detectable in the washes. Cells were incubated for one additional h with neat medium. Afterwards the cells were pelleted, resuspended in 50 mM Tris pH 7.5, containing a cocktail of protease inhibitors and they were solubilised by ultrasonication for 1 min. The insoluble fraction was pelleted for 15 min using an Eppendorf centrifuge and the supernatant was analysed by anal. RP-HPLC (0–60% MeCN gradient, λ=254 nm). Intact test compound was identified by reference to chromatograms obtained with authentic test compound and by DE MALDI-TOF MS analysis of the peak fraction indicated with an arrow in FIG. 2. Pellets were further extracted with DMSO and extracts analysed similarly, no test compound was detected.

Example 41

Serum Stability of Peptide Vectors

Test compounds were dissolved in cell-conditioned tissue culture medium (10% FCS in DMEM) at concentrations varying from 1 to 40 μM. The solutions were incubated at 37° C. and samples were withdrawn at intervals. After filtration, aliquots were analysed by RP-HPLC (using a photodiode array UV detector). Intact vectors were identified by reference to chromatograms obtained with authentic peptides and by DE MALDI-TOF analysis of appropriate peak fractions. The half-lives for four different vectors are summarised in Table 4. Similar results were obtained when human or murine serum was substituted for bovine serum (FCS). The latter was chosen preferentially in order to replicate the conditions used for cytotoxicity assays on cell cultures. In all cases the main metabolism product of the 16mer peptide acid H-Arg-Gln-Ile-Lys-Ile-Trp-Phe-Gln-Asn-Arg-Arg-Met-Lys-Trp-Lys-Lys-OH (SEQ ID No. 25) was the 15mer resulting from C-terminal truncation of a Lys residue. This 15mer peptide was observed to survive for several h prior to further carboxy-terminal degradation. The L-amino acid-containing vector peptide amides were degraded much more slowly, no individual metabolites could be identified. All D-amino acid-containing peptide vectors studied were very stable and could usually still be detected after 72 h incubations.

TABLE 4

| Vector | Serum t$_{1/2}$ |
|---|---|
| H-Arg-Gln-Ile-Lys-Ile-Trp-Phe-Gln-Asn-Arg-Arg-Met-Lys-Trp-Lys-Lys-OH | 10 min |
| H-Arg-Gln-Ile-Lys-Ile-Trp-Phe-Gln-Asn-Arg-Arg-Met-Lys-Trp-Lys-Lys-NH$_2$ | >12 h |
| H-D-Arg-D-Gln-D-Ile-D-Lys-D-Ile-D-Trp-D-Phe-D-Gln-D-Asn-D-Arg-D-Arg-D-Met-D-Lys-D-Trp-D-Lys-D-Lys-NH$_3$ | >24 h |
| H-Arg-Arg-Met-Lys-Trp-Lys-Lys-NH$_2$ | 3 h |

(Arg-Gln-Ile-Lys-Ile-Trp-Phe-Gln-Asn-Arg-Arg-Met-Lys-Trp-Lys-Lys corresponds with SEQ ID No. 25 and Arg-Arg-Met-Lys-Trp-Lys-Lys corresponds with SEQ ID No. 26)

Example 42

Serum Stability of Drug-ester Linkages

Test compounds (Table 5: A, 4-[succinimidopropionoyl-(H-Cys-Arg-Gln-Ile-Lys-Ile-Trp-Phe-Gln-Asn-Arg-Arg-Met-Lys-Trp-Lys-Lys-NH$_2$)]podophyllotoxin (SEQ ID No. 27); B, 4-[acetyl-(H-Cys-Arg-Gln-Ile-Lys-Ile-Trp-Phe-Gln-Asn-Arg-Arg-Met-Lys-Trp-Lys-Lys-OH)]podophyllotoxin (SEQ ID No. 27); C, 2'-[succinimidopropionoyl-(H-Cys-Arg-Gln-Ile-Lys-Ile-Trp-Phe-Gln-Asn-Arg-Arg-Met-Lys-Trp-Lys-Lys-NH$_2$)]paclitaxel) (SEQ ID No. 27) were dissolved in cell-conditioned tissue culture medium (10% FCS in DMEM) at concentrations varying from 1 to 40 μM. The solutions were incubated at 37° C. and samples were withdrawn at intervals. After filtration, aliquots were analysed by RP-HPLC (using a photodiode array UV detector). Hydrolysis of the ester bonds between the drug hydroxy groups and the linker carboxyl groups was assessed by appearance of free podophyllotoxin or paclitaxel. The half-lives for three different drug-linker combinations are summarised in Table 5. Similar results were obtained when human or murine serum was substituted for bovine serum (FCS). The latter was chosen preferentially in order to replicate the conditions used for cytotoxicity assays on cell cultures.

TABLE 5

| Entry | Structure | Serum $t_{1/2}$ of Drug-Linker Ester bond |
|---|---|---|
| A | 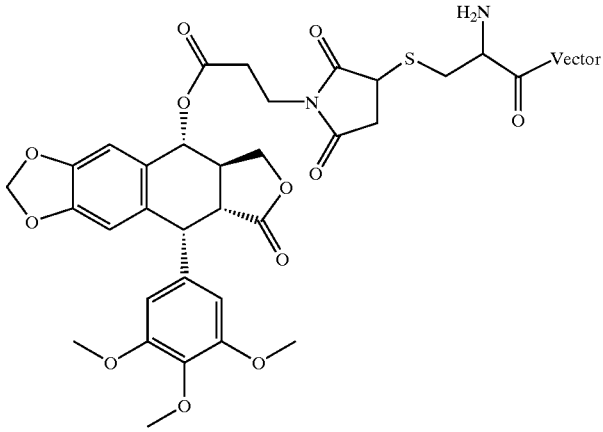 | >24 h |
| B | 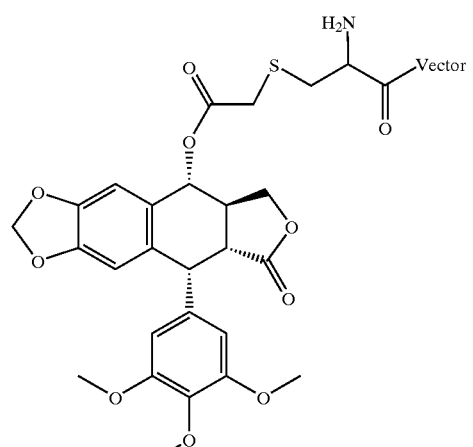 | 40 min |
| C | 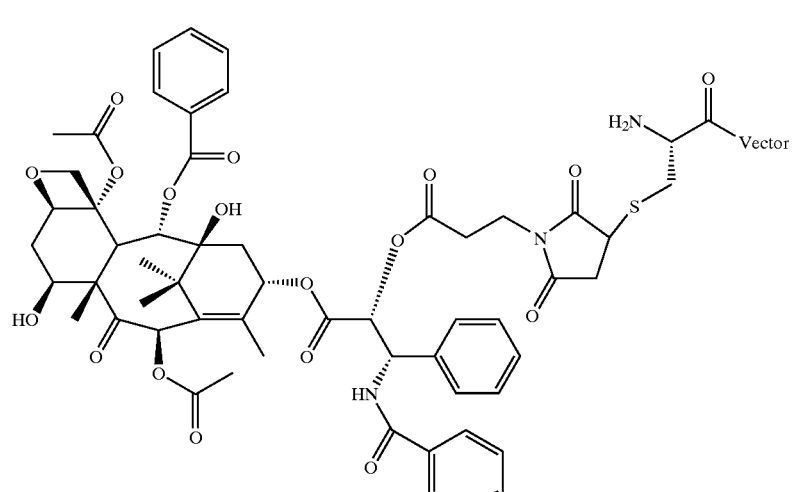 | >12 h |

Example 43

Comparison of Cytotoxic Activities of Paclitaxel and its Vector Conjugates

In order to demonstrate the cytotoxic biological effect on cancer cells (A549 lung carcinoma and MCF7 breast carcinoma cell lines in Table 6) of the paclitaxel-conjugates (paclitaxel-(16mer vector), 2'-[succinimidopropionoyl-(H-Cys-Arg-Gln-Ile-Lys-Ile-Trp-Phe-Gln-Asn-Arg-Arg-Met-Lys-Trp-Lys-Lys-Gly-Cys-Gly-NH$_2$)]paclitaxel (SEQ ID No. 30); paclitaxel-(7mer vector), 2'-

[succinimidopropionoyl-(H-Cys-βAla-Arg-Arg-Met-Lys-Trp-Lys-Lys-NH$_2$)]paclitaxel) (SEQ ID No. 19), cells were exposed to test compounds for 1 h only, i.e. a period during which the conjugates were shown to be metabolically stable under the conditions of the assay procedures (refer Examples 41 & 42). IC$_{50}$ values for 1-h and 3-d exposures are summarised in Table 6 and are compared with those obtained with free paclitaxel. It should be noted that due to the negligible water-solubility of unconjugated paclitaxel, washing off of compound not internalised into the cells after exposure was much less effective than for the conjugates, which have solubility in physiological media of >10 mg/mL. It can be concluded that for the 1-h exposure results, the full cytotoxic activity can be attributed to the intact paclitaxel-conjugates (refer also Example 37).

Assay procedure—Cells were seeded into 96-well plates at 2,500 cells per well in DMED, containing 10% FCS and antibiotics. After overnight incubation, test compounds were prepared as dilution series in cell medium (addition of dimethylsulfoxide in the case of free paclitaxel to effect partial dissolution) and were added to the cells. For the 1-h exposure samples, incubation was continued for 1 h, cell culture medium supernatants were removed and the wells were further washed with cell culture medium (5×2 min). Total viable cells were quantitated after a total of 72 h incubation using a standard MTT-assay.

TABLE 6

| | 72-h IC$_{50}$ ($\mu$M) Cell line | | | |
|---|---|---|---|---|
| | A549 | | MCF7 | |
| | Exposure time | | | |
| Test compound | 1 h | 3 d | 1 h | 3 d |
| Paclitaxel | 0.028 | <0.015 | 0.04 | <0.015 |
| Paclitaxel-(16 mer vector) conjugate | 0.618 | <0.015 | 0.202 | 0.017 |
| Paclitaxel-(7 mer vector) conjugate | 0.043 | <0.015 | 0.325 | <0.015 |

Example 44

Evaluation of Paclitaxel- and Podophyllotoxin-vector Conjugates in Carcinoma Cell Line Panel Serial dilutions of test compounds (Table 7: 2'-paclitaxel vector conjugate, 2'-[succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27); 7-paclitaxel vector conjugate, 7-[succinimidopropionoyl-(H-Cys-Arg-Gln-Ile-Lys-Ile-Trp-Phe-Gln-Asn-Arg-Arg-Met-Lys-Trp-Lys-Lys-OH)]paclitaxel (SEQ ID No. 27); 4-podophyllotoxin vector conjugate, 4-[Succinimidopropionoyl-(H-Cys-Arg-Gln-Ile-Lys-Ile-Trp-Phe-Gln-Asn-Arg-Arg-Met-Lys-Trp-Lys-Lys-OH)]podophyllotoxin) (SEQ ID No. 27) were applied to the cell lines. After incubation for 96 h, cytotoxicity was assessed using a standard SRB-assay.

TABLE 7

| | 96-h IC$_{50}$ ($\mu$M) cytotoxicity evaluation in cell line panel | | | | | |
|---|---|---|---|---|---|---|
| Cell Line | Vector | 2'-Paclitaxel Vector Conjugate | 7-Paclitaxel Vector Conjugate | Paclitaxel | 4-Podophyllotoxin Vector Conjugate | Etoposide |
| BE | >25 | 0.0305 | 1.6 | <0.0025 | 0.55 | 1.1 |
| COLO205 | >25 | 0.074 | 1.9 | 0.0026 | 0.495 | 0.8 |
| DLD-1 | >25 | 0.6 | 25 | 0.054 | 0.65 | 0.57 |
| HCT116 | >25 | 0.096 | 2.4 | <0.0025 | 0.53 | 1.9 |
| HT29 | >25 | 0.092 | 2.25 | <0.0025 | 0.53 | 2.6 |
| KM12 | >25 | 0.105 | 2.95 | 0.00285 | 0.58 | 0.58 |
| LIM1215 | >25 | 0.12 | 3.65 | 0.0058 | 1.1 | 0.33 |
| LS174T | >25 | 0.195 | 7.4 | 0.0085 | 1.25 | 0.46 |
| A2780 | >25 | 0.105 | 2.8 | <0.0025 | 0.54 | 0.21 |
| A2780Cis$^R$ | >25 | 0.125 | 4.3 | 0.0051 | 0.54 | 0.68 |
| CH1 | >25 | 0.115 | 6.6 | 0.00415 | 0.51 | 0.165 |
| CH1Dox$^R$ | >25 | 4.6 | >25 | 0.54 | 0.51 | 6.6 |
| CH1Taxol$^R$ | >25 | 0.13 | 8.7 | 0.0058 | 0.52 | 0.145 |
| SKOV-3 | >25 | 0.235 | 22 | 0.01 | 0.74 | 13 |

Example 45

Evaluation of Etoposide and Podophyllotoxin Derivatives in Topoisomerase II Inhibition Assay Topoisomerase II assay—Plasmid DNA (0.3 $\mu$g) was incubated at 37° C. with 4 units of purified recombinant human topoisomerase II in cleavage buffer (30 mM Tris.HCl, pH 7.6, 60 mM NaCl, 3 mM ATP, 15 mM mercaptoethanol, 8 mM MgCl$_2$) with or without the addition of test compound (at 1 mM, 100 $\mu$M, or 10 $\mu$M final concentration). Reactions were stopped by the immediate addition of SDS (1% w/v final). Samples were treated with proteinase K (30 min at 37° C.) and extracted twice with an equal volume of 42:1 CHCl$_3$/i-amyl alcohol. After adding loading dye, samples were loaded to a 4×TAE, 1% agarose gel containing 0.5 mg/mL ethidium bromide and electrophoresed for 16–24 h. Topoisomerase II inhibition was judged by the production of linear plasmid DNA, representing trapped cleavage intermediate, and by the ratio of substrate (spercoiled DNA) to product (relaxed DNA). A relaxation assay was performed identically, except that the reaction buffer was optimised for the detection of catalysis rather than cleavage, i.e. only 2 units of enzyme were used per sample. The reaction buffer was 50 mM Tris.HCl, pH 8, 120 mM KCl, 0.5 mM ATP, 0.5 mM dithiothreitol, 10 mM MgCl$_2$. Topoisomerase II inhibition was judged by the ratio of substrate (supercoiled DNA) to product (relaxed DNA).

TABLE 8

| Test Compound | Activity observed[a] |
|---|---|
| Etoposide | IC |
| Podophyllotoxin | — |
| 4'-Demethylepipodophyllotoxin | IC |
| 4'-Demethyl-4-(4"-aminoanilino)epipodophyllotoxin | I |
| H-βAla-Arg-Arg-Met-Lys-Trp-Lys-Lys-NH$_2$ | — |
| 4-[Succinimidopropionoyl-(H-Cys-βAla-Arg-Arg-Met-Lys-Trp-Lys-Lys-NH$_2$)]podophyllotoxin | — |
| 4'-[Succinimidopropionoyl-(H-Cys-βAla-Arg-Arg-Met-Lys-Trp-Lys-Lys-NH$_2$)]epipodophyllotoxin | IC |
| 4'-Demethyl-4-[acetyl-(H-Cys-βAla-Arg-Arg-Met-Lys-Trp-Lys-Lys-NH$_2$)]epipodophyllotoxin | IC |
| 4'-Demethyl-4-[4"-aminoanilino-(succinimidopropionoyl)-(H-Cys-bAla-Arg-Arg-Met-Lys-Trp-Lys-Lys-NH$_2$)]-epipodophyllotoxin | I |

[a] I denotes inhibition of relaxation of supercoiled plasmid by topoisomerase II. C denotes accumulation of topoisomerase II reaction intermediate. (Ala-Arg-Arg-Met-Lys-Trp-Lys-Lys corresponds with SEQ ID No. 24 and Cys-Ala-Arg-Meg-Lys-Trp-Lys-Lys corresponds with SEQ ID No. 19)

EXAMPLES

| | Abbreviations |
|---|---|
| Boc | tert-Butyloxycarbonyl |
| Bu$^t$ | tert-Butyl |
| CF$_3$COOH | Trifluoroacetic acid |
| CH$_2$Cl$_2$ | Dichloromethane |
| DE MALDI-TOF MS | Delayed extraction matrix-assisted laser desorption ionisation time-of-flight mass spectrometry |
| DMF | N,N-Dimethylformamide |
| Et$_2$O | Diethyl ether |
| Fmoc | 9-Fluorenylmethyloxycarbonyl |
| HMBA | p-Hydroxymethylbenzoyl |
| HOBt | 1-Hydroxybenzotriazole |
| MeCN | Acetonitrile |
| Pmc | 2,2,5,7,8-Pentamethylchroman-6-sulphonyl |
| Pr$^i_2$NEt | N,N-Diisopropylethylamine |
| PyBOP | Benzotriazole-1-yl-oxy-tris-pyrrolidino-phosphonium hexafluorophosphate |
| RP-HPLC | Reversed-phase high performance liquid chromatography |
| Trt | Trityl (triphenylmethyl) |

Example 1a

H-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ 11 No. 25)

Peptide assembly was performed using an ABI 433A Peptide Synthesizer (Perkin-Elmer Applied Biosystems). A standard synthesis protocol ("FastMoc 0.25 mmol MonPrevPk") was applied. The starting resin was Fmoc-Lys(Boc)-[(4-(hydroxymethyl)pheneoxyacetyl)-Resin] (ABI 401425; 0.5 mmol/g). The final peptidyl resin (1.37 g; 100%) was washed with Et$_2$O and dried in vacuo.

In order to demonstrate the chemical integrity of this intermediate, a small aliquot of peptidyl resin was cleaved and deprotected, followed by analysis of the crude product H-Arg-Gln-Ile-Lys-Ile-Trp-Phe-Gln-Asn-Arg-Arg-Met-Lys-Trp-Lys-Lys-OH (SEQ ID No. 1), which revealed purity of >90% (anal. RP-HPLC) and chemical identity (DE MALDI-TOF MS and quantitative amino acid analysis).

[H-Glu(OBu$^t$)-Gly-bAla]$_4$-Lys$_2$-Lys-bAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ ID No. 28)

The above peptidyl resin (137 mg, 0.025 mmol) was acylated with Fmoc-bAla-OH (47 mg, 0.15 mmol), PyBOP (78 mg, 0.15 mmol), HOBt (20 mg, 0.15 mmol) and Pr$^i_2$NEt (39 mL, 0.225 mmol) in DMF (2 mL) during 2 h. It was then Fmoc-deprotected with 20% piperidine in DMF for 20 min and washed extensively with DMF. The product was further extended by two successive acylation and deprotection cycles using Fmoc-Lys(Fmoc)-OH (0.15 mmol in first cycle; 0.3 mmol in second cycle) using similar coupling and deprotection steps. This was followed by further chain extension with Fmoc-Gly-OH (0.6 mmol) and Fmoc-Glu(OBu$^t$)-OH (0.6 mmol), again using similar acylation and Fmoc-deprotection conditions. The product was Fmoc-deprotected and washed extensively with DMF, CH$_2$Cl$_2$ and Et$_2$O, followed by drying in vacuo.

In order to demonstrate chemical integrity of this intermediate, a small aliquot of peptidyl resin was cleaved and side-chain deprotected, followed by analysis of the crude product [H-Glu-Gly-bAla]$_4$-Lys$_2$-Lys-bAla-Arg-Gln-Ile-Lys-Ile-Trp-Phe-Gln-Asn-Arg-Arg-Met-Lys-Trp-Lys-Lys-OH (SEQ ID No. 28), which revealed purity (>89%; RP-HPLC on Vydac 218TP54, 1 mL/min, 25° C., 15–25% MeCN in 0.1% aq CF$_3$COOH over 20 min, t$_R$=17.7 min, l=200–300 nm) and identity (DE MALDI-TOF MS: [M+H]$^+$=3732, C$_{165}$H$_{269}$N$_{53}$O$_{44}$S=3731.30).

{[4[N-(2,4-diamino-6-pteridinyl-methyl)-N-methylamino]benzoyl]-Glu(OBu$^t$)-Gly-bAla}$_4$-Lys$_2$-Lys-bAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ ID No. 28)

The above peptidyl resin (76 mg, 0.025 mmol) was reacted overnight at room temperature with 4[N-(2,4-diamino-6-pteridinyl-methyl)-N-methylamino]benzoic acid hemihydrochloride dihydrate (Aldrich 86; 155-3; 76 mg, 0.2 mmol) and PyBOP (104 mg, 0.2 mmol), HOBt (27 mg, 0.2 mmol) and Pr$^i_2$NEt (70 mL, 0.4 mmol) in DMF (2 mL). The product was washed successively with DMF, CH$_2$Cl$_2$ and Et$_2$O and dried in vacuo to afford the title compound (85 mg orange peptidyl resin).

{[4[N-(2,4-diamino-6-pteridinyl-methyl)-N-methylamino]benzoyl]-Glu-Gly-bAla}$_4$-Lys$_2$-Lys-bAla-Arg-Gln-Ile-Lys-Ile-Trp-Phe-Gln-Asn-Arg-Arg-Met-Lys-Trp-Lys-Lys-OH (SEQ ID No. 28)
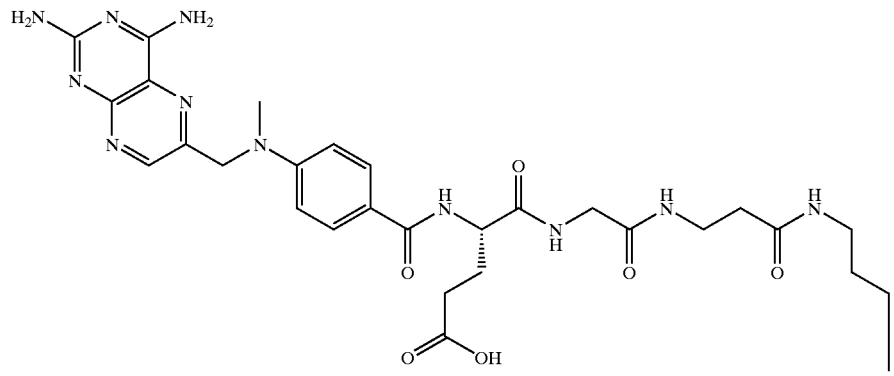
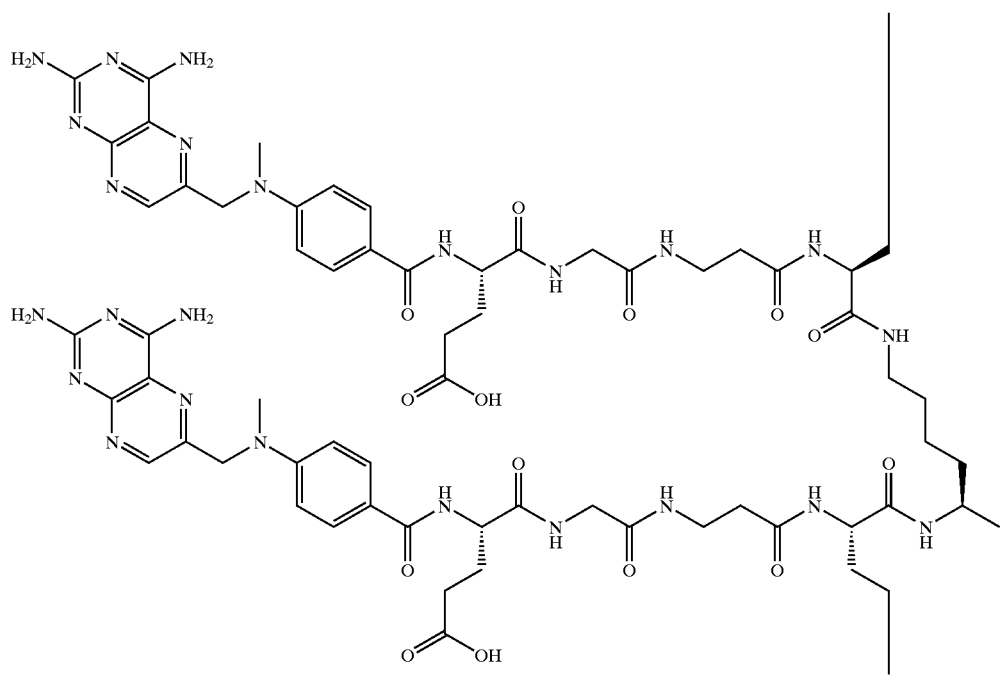
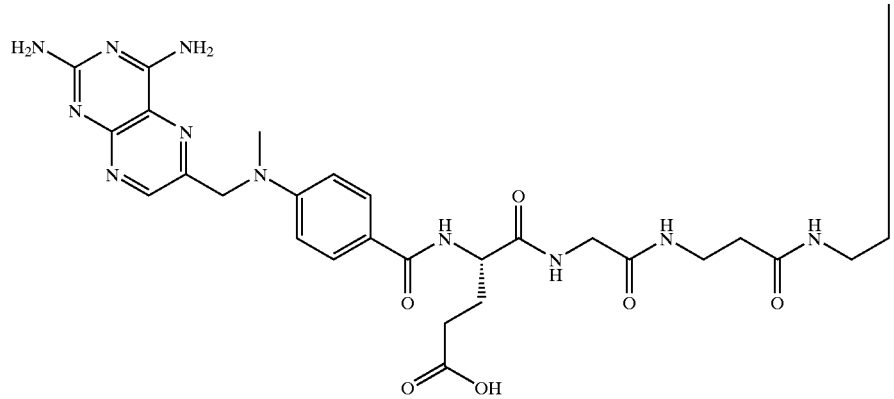

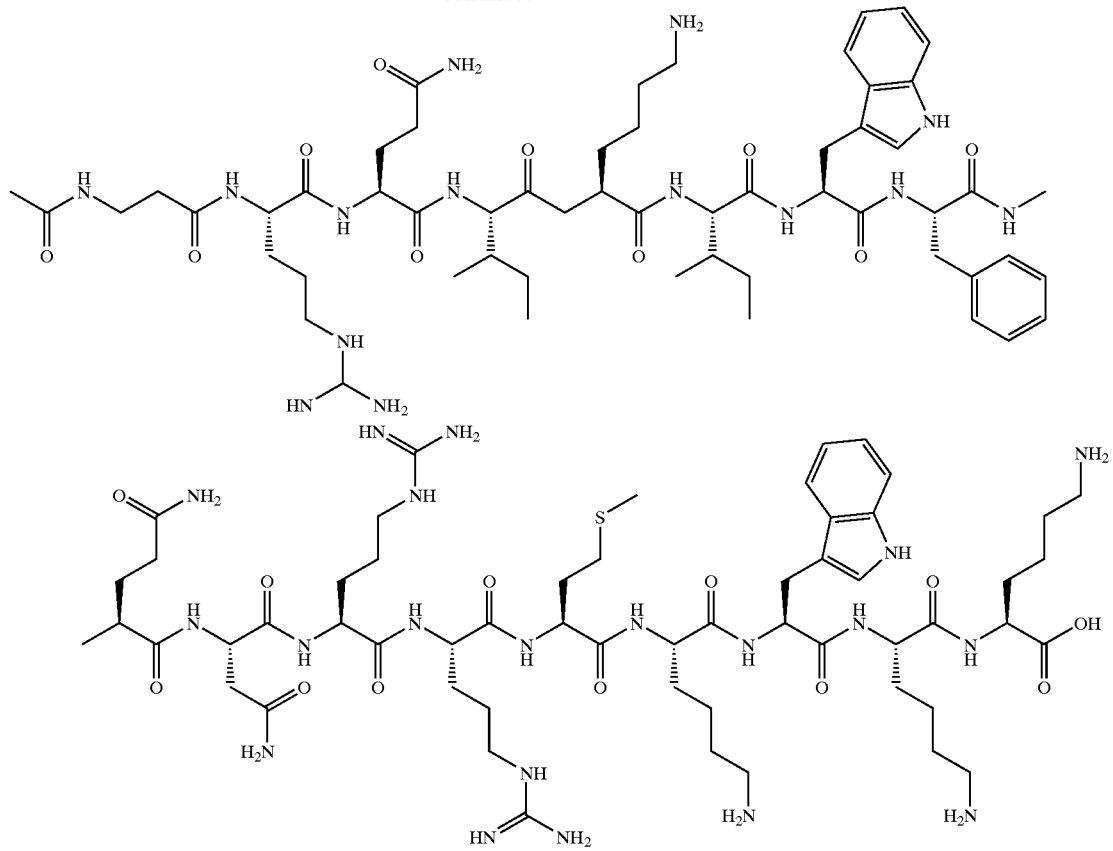

The above product was treated for 1.5 h at room temperature with phenol/H$_2$O/thioanisole/1,2-dithioethane/CF$_3$COOH, 0.75:0.5:0.5:0.25:10, (12 mL). Resin residue was then filtered off and washed on a sinter with small aliquots of neat CF$_3$COOH. The combined filtrate and washings were treated with Et$_2$O (100 mL) and cooled. The precipitated product was collected by centrifugation and the ethereal supernatant was decanted. The product was washed three more times with Et$_2$O in a similar fashion. The final crude product was dried in vacuo (61 mg orange powder). This material was redissolved in 4 mL 0.1% aq CF$_3$COOH and filtered. The resulting solution was applied (two separate runs) to an RP-HPLC column (Vydac 218TP1022; 22×250 mm). The column was eluted at 9 mL/min using a gradient from 17.5 to 27.5% MeCN in 0.1% aq CF$_3$COOH over 40 min (25° C.). Peak fractions were collected, monitored (analytical RP-HPLC) and pooled as appropriate. After vacuum centrifugation, pure title compound (13.5 mg) was obtained. Anal. RP-HPLC: $t_R$=17.8 min (Vydac 218TP54, 17.5–27.5% MeCN in 0.1% aq CF$_3$COOH over 20 min, 1 mL/min, 25° C.; purity>99%, l=200–300 nm). DE MALDI-TOF MS: [M+H]$^+$=4962 (C$_{225}$H$_{321}$N$_{81}$O$_{48}$S=4960.54).

Example 2a

H-Cys-Arg-Gln-Ile-Lys-Ile-Trp-Phe-Gln-Asn-Arg-Arg-Met-Lys-Trp-Lys-Lys-OH (SEQ ID No. 27)

H-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ ID No. 1) (see example 1; 411 mg, 0.075 mmol) was acylated with Fmoc-Cys(Trt)-OH (264 mg, 0.45 mmol), PyBOP (234 mg, 0.45 mmol), HOBt (61 mg, 0.45 mmol) and P$^i_2$NEt (0.12 mL, 0.675 mmol) in DMF (3 mL) during 3 h. The resulting peptidyl resin was washed with DMF (3×5 min, 25 mL each), drained and treated with 20% piperidine in DMF during 20 min. After filtration of the reagent, the product H-Cys(Trt)-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ ID No. 27) was washed successively with DMF, CH$_2$Cl$_2$ and Et$_2$O, before being dried in vacuo.

The above product was treated for 2 h at room temperature with phenol/H$_2$O/thioanisole/1,2-dithioethane/CF$_3$COOH, 0.75:0.5:0.5:0.25:10 (12 mL). Resin residue was then filtered off and washed on a sinter with small aliquots of neat CF$_3$COOH. The combined filtrate and washings were treated with Et$_2$O (100 mL) and cooled. The precipitated product was collected by centrifugation and the ethereal supernatant was decanted. The product was washed three more times with Et$_2$O in a similar fashion. The final crude product was dried in vacuo (238 mg). An aliquot (119 mg) of this material was redissolved in 2 mL 0.1% aq CF$_3$COOH and filtered. The resulting solution was applied to an RP-HPLC column (Vydac 218TP1022; 22×250 mm). The column was eluted at 9 mL/min using a gradient from 17.5 to 27.5% MeCN in 0.1% aq CF$_3$COOH over 40 min (25° C.). Peak fractions were collected, monitored (analytical RP-HPLC) and pooled as appropriate. After vacuum centrifugation, pure title compound (60.9 mg) was obtained. Anal. RP-HPLC: $t_R$=15.8 min (Vydac 218TP54, 17.5–27.5% MeCN in 0.1% aq $CF_3COOH$ over 20 min, 1 mL/min, 25° C.; purity>99%, l=214 nm). DE MALDI-TOF MS: $[M+H]^+$=2351 ($C_{107}H_{173}N_{35}O_{21}S_2$=2349.87).

N-[3-(Maleimido)benzoyl]-doxorubicin

Doxorubicin hydrochloride (Aldrich, 86,036–0; 5.9 mg, 0.01 mmol) was dissolved in $H_2O$ (1 mL) and DMF (0.5 mL). Buffer (0.1 M aq phosphate, pH 7.2; 0.5 mL) was added with stirring. To the resulting suspension 3-maleimidobenzoic acid N-hydroxysuccinimide ester (Sigma, M2786; 12.9 mg, 0.04 mmol) in DMF (1 mL) was added dropwise. The red-coloured reaction mixture cleared temporarily and after ca. 10 min precipitation was observed. Reaction progress was monitored by anal. RP-HPLC and after 2 h all doxorubicin had reacted. The mixture was then diluted with $H_2O$ (1.5 mL), cooled to 4° C. and centrifuged. The supernatant was decanted. The residual pellet was redissolved in DMF (1 mL) and diluted with 0.1% aq $CF_3COOH$ (2 mL). This solution was applied to a solid-phase extraction cartridge (LiChrolut RP-18, 500 mg; Merck); the cartridge was washed with 0.1% aq $CF_3COOH$ (4 mL) and eluted with 6:4 $MeCN/H_2O$ (containing 0.1% $CF_3COOH$) in two fractions (2×4 mL). The first fraction contained the title compound and was used directly in the next step.

N-{3-[3-(Cys-Arg-Gln-Ile-Lys-Ile-Trp-Phe-Gln-Asn-Arg-Arg-Met-Lys-Trp-Lys-Lys-OH) succinimido]benzoyl}-doxorubicin (SEQ ID No. 27)

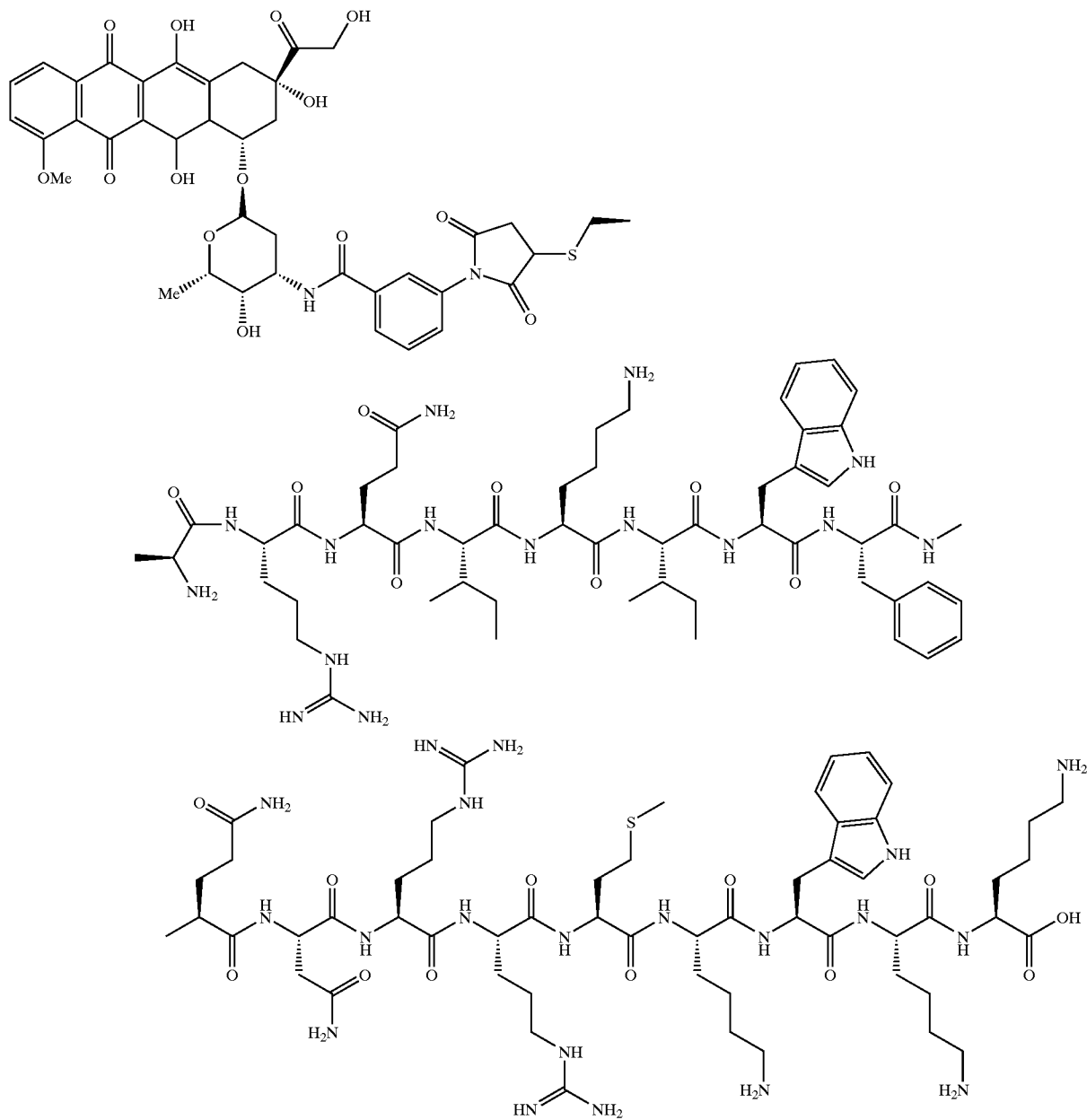

The above N-[3-(Maleimido)benzoyl]-doxorubicin solution was diluted with DMF (1 mL) and Et$_3$N (50 mL) was added. The solution turned dark brown. H-Cys-Arg-Gln-Ile-Lys-Ile-Trp-Phe-Gln-Asn-Arg-Arg-Met-Lys-Trp-Lys-Lys-OH (SEQ ID No. 27) (5 mg), dissolved in DMF (1 mL) was then added. The mixture was stirred and the brown colour was observed to discharge, leaving a light red solution. The reaction was monitored by anal. RP-HPLC. After 1.5 h, all 3-(maleimido-benzoyl)-doxorubicin had reacted. The solution was acidified with AcOH (0.5 mL), diluted with H$_2$O (3 mL) and applied to a solid-phase extraction cartridge (LiChrolut RP-18, 500 mg; Merck). The cartridge was washed with 0.1% aq CF$_3$COOH (6 mL) and eluted (6 mL of 6:4 MeCN/H$_2$O (containing 0.1% CF$_3$COOH)). The eluate was dried by vacuum centrifugation. The residue was redissolved in 0.1% aq CF$_3$COOH (2 mL), filtered and applied to an RP-HPLC column (Vydac 218TP1022; 22×250 mm). The column was eluted at 9 mL/min using a gradient from 20 to 40% MeCN in 0.1% aq CF$_3$COOH over 40 min (25° C.). Peak fractions were collected, monitored (analytical RP-HPLC) and pooled as appropriate. After vacuum centrifugation, pure title compound (1.2 mg) was obtained. Anal. RP-HPLC: $t_R$=15.6 & 15.8 (partly resolved thioether diastereomers) min (Vydac 218TP54, 0–60% MeCN in 0.1% aq CF$_3$COOH over 20 min, 1 mL/min, 25° C.; purity>95%, l=200–300 nm). DE MALDI-TOF MS: [M+H]$^+$=3094, [M+2H]$^{2+}$=1548 (C$_{145}$H$_{207}$N$_{37}$O$_{35}$S$_2$=3092.56).

Example 3a

2'-[(3-Maleimidopropionoyl)]-paclitaxel

3-Maleimidopropionic acid (5.7 mg, 0.034 mmol) was dissolved in dry CH$_2$Cl$_2$ (0.5 mL). The mixture was stirred and diisopropylcarbodiimide (2.4 mg, 0.019 mmol) in dry CH$_2$Cl$_2$ (0.5 mL) was added. The reaction was allowed to proceed with stirring for 30 min. Solvent was then removed under reduced pressure. The residue of 3-maleimidopropionic acid anhydride was redissolved in dry pyridine (0.5 mL). A solution of paclitaxel (Aldrich 41,701-7; 1 mg, 0.0012 mmol) in dry pyridine (0.5 mL) was added and the mixture was stirred under N$_2$ for 3 h. It was then evaporated to dryness under reduced pressure. The residue was treated with H$_2$O (1.5 mL). After 10 min, it was extracted with CH$_2$Cl$_2$ (3×5 mL). The combined extracts were washed with H$_2$O (3×1 mL), dried with MgSO$_4$, filtered and evaporated to dryness to leave a white residue of the title compound.

2'-{3-[3-(Cys-Arg-Gln-Ile-Lys-Ile-Trp-Phe-Gln-Asn-Arg-Arg-Met-Lys-Trp-Lys-Lys-OH)succinimido]propionoyl}-paclitaxel (SEQ ID No. 27)

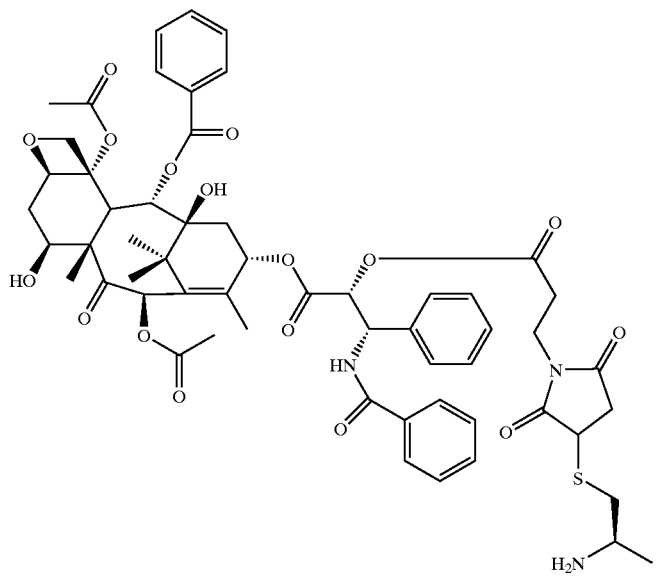

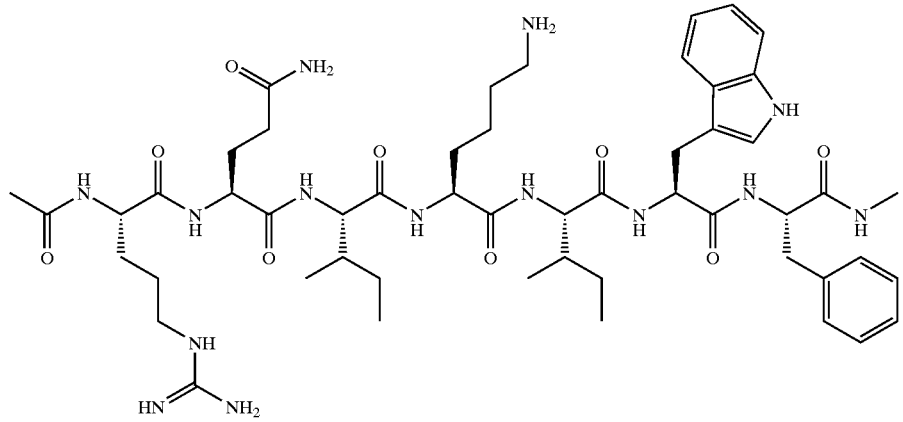

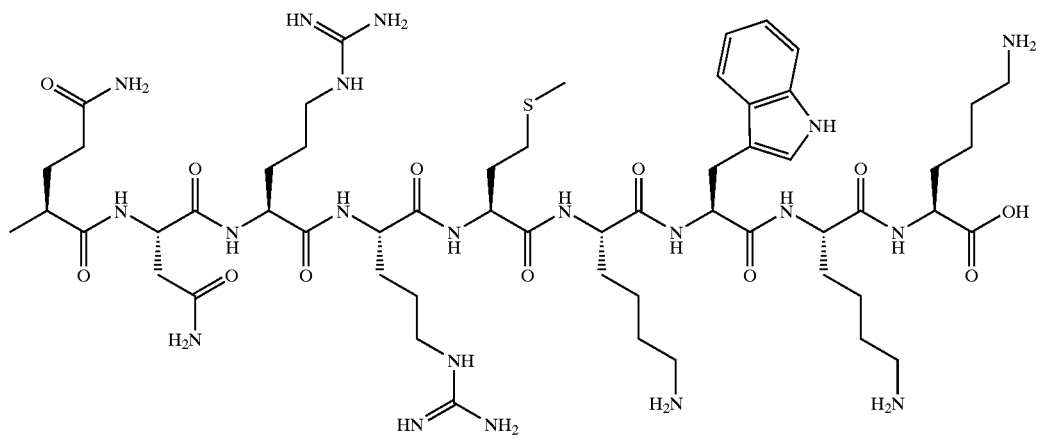

The product from the previous reaction was redissolved in DMF (0.25 mL) and H-Cys-Arg-Gln-Ile-Lys-Ile-Trp-Phe-Gln-Asn-Arg-Arg-Met-Lys-Trp-Lys-Lys-OH (SEQ ID No. 27) (2.5 mg, 0.0011 mmol), dissolved in DMF (0.25 mL) was then added, together with $Et_3N$ (ca. 0.05 mL). The mixture was stirred under $N_2$ and was monitored by anal. RP-HPLC. After 45 min, the reaction was complete. The mixture was diluted to 2 mL with 0.1% aq $CF_3COOH$, filtered and applied to an RP-HPLC column (Vydac 218TP1022; 22×250 mm). The column was eluted at 9 mL/min using a gradient from 0 to 60% MeCN in 0.1% aq $CF_3COOH$ over 40 min (25° C.). Peak fractions were collected, monitored (analytical RP-HPLC) and pooled as appropriate. After vacuum centrifugation, pure title compound (1.2 mg) was obtained. Anal. RP-HPLC: $t_R$=17.4 & 17.5 (partly resolved thioether diastereomers) min (Vydac 218TP54, 0–60% MeCN in 0.1% aq $CF_3COOH$ over 20 min, 1 mL/min, 25° C.; purity>95%, l=200–300 nm). DE MALDI-TOF MS: $[M+H]^+$=3356, $[M+2H]^{2+}$=1679 ($C_{161}H_{229}N_{37}O_{38}S_2$=3354.90).

Example 4a

In vitro cytotoxic activity of {[4[N-(2,4-diamino-6-pteridinyl-methyl)-N-methylamino]benzoyl]-Glu-Gly-bAla}$_4$-Lys$_2$-Lys-bAla-Arg-Gln-Ile-Lys-Ile-Trp-Phe-Gln-Asn-Arg-Arg-Met-Lys-Trp-Lys-Lys-OH (SEQ ID No. 28)

This compound (abbreviated 'MTX-Pen' in tables below) was evaluated for its ability to inhibit cell proliferation of normal (immortalised) human cells (HaCaT cells, Tables 1 & 2) and a human colorectal cancer cell line (HT29, Table 3). The free drug methotrexate (Tables 1–3) and the free vector H-Ala-Arg-Gln-Ile-Lys-Ile-Trp-Phe-Gln-Asn-Arg-Arg-Met-Lys-Trp-Lys-Lys-OH (SEQ ID No. 28) (abbreviated 'Pen' in Table 1 below) were included for the purposes of comparison.

Assay procedure—Cells were seeded into 96-well plates at 2,500 cells/well in DMEM with 10% foetal calf serum and antibiotics. After overnight incubation, test compound dilutions in cell medium were prepared and were added to the cells. Samples were taken 1, 2, 3, and 4 days after compound addition. Nucleotide Releasing Reagent (LumiTech ViaLight kit) was added in order to lyse the cells and release ATP. After incubation at room temperature (5 min), the mixtures were transferred to opaque 96-well plates and stored at −20° C. until analysis. After loading plates into a luminometer (Lucy 1, Labtech International), ATP Monitoring Reagent (20 mL/well, LumiTech ViaLight kit) was added to each well successively and light intensity was measured immediately. Six readings were taken per sample. Each assay point was established using six replicates and appropriate controls. ATP bioluminescence was found to be proportional to viable cell count over the entire cells/well range used.

Statistically significant results in the tables below are printed in bold face.

TABLE 1

(HaCaT Cells)

| | % Cell Death | | | | | | | | | | | |
|---|---|---|---|---|---|---|---|---|---|---|---|---|
| | Day 1 | | | Day 2 | | | Day 3 | | | Day 4 | | |
| Dose (μM) | MTX | MTX-Pen | Pen | MTX | MTX-Pen | Pen | MTX | MTX-Pen | Pen | MTX | MTX-Pen | Pen |
| 40.0 | 4 | 29 | 16 | 15 | 82 | −22 | 79 | 97 | 5 | 92 | 98 | 12 |
| 13.3 | 22 | −42 | 18 | 35 | 63 | 0 | 82 | 97 | −17 | 92 | 98 | −6 |
| 4.4 | 4 | −8 | 8 | 24 | 45 | −4 | 77 | 95 | −1 | 93 | 98 | 10 |
| 1.5 | 13 | −24 | 16 | 31 | 82 | −31 | 77 | 82 | 2 | 94 | 88 | −14 |
| 0.5 | −4 | −19 | 6 | 31 | 2 | −6 | 75 | 29 | −29 | 93 | 49 | −26 |
| 0.2 | 7 | 14 | 26 | 11 | 21 | 0 | 79 | 20 | −3 | 93 | 51 | 21 |

TABLE 2

(HaCaT Cells)

| | % Cell Death | | | | | | | |
|---|---|---|---|---|---|---|---|---|
| | Day 1 | | Day 2 | | Day 3 | | Day 4 | |
| Dose (μM) | MTX | MTX-Pen | MTX | MTX-Pen | MTX | MTX-Pen | MTX | MTX-Pen |
| 40.0 | | 42 | | 88 | | 95 | | 94 |
| 13.3 | | 27 | | 87 | | 95 | | 94 |
| 4.4 | 21 | 15 | 70 | 52 | 97 | 95 | 92 | 88 |
| 1.5 | 14 | 19 | 67 | 12 | 96 | −16 | 91 | 17 |
| 0.5 | 0 | 13 | 59 | 24 | 96 | −27 | 91 | 2 |
| 0.2 | 3 | | 41 | | 94 | | 86 | |
| 0.1 | 19 | | 7 | | 45 | | 65 | |

TABLE 3

(HT 29 Cells)

| | % Cell Death | | | | | | | |
|---|---|---|---|---|---|---|---|---|
| | Day 1 | | Day 2 | | Day 3 | | Day 4 | |
| Dose (μM) | MTX | MTX-Pen | MTX | MTX-Pen | MTX | MTX-Pen | MTX | MTX-Pen |
| 40.0 | | 31 | | 79 | | 96 | | 98 |
| 13.3 | | 3 | | 45 | | 88 | | 96 |
| 4.4 | −14 | 10 | −4 | 6 | 58 | 46 | 86 | 77 |
| 1.5 | 17 | 16 | −5 | 9 | 48 | 15 | 84 | 45 |
| 0.5 | 15 | 14 | −12 | 8 | 52 | 17 | 88 | 16 |
| 0.2 | 10 | | −5 | | 54 | | 85 | |
| 0.1 | 6 | | −17 | | 52 | | 84 | |

Example 5a

[(3-Maleimidopropionoyl)]bohemine

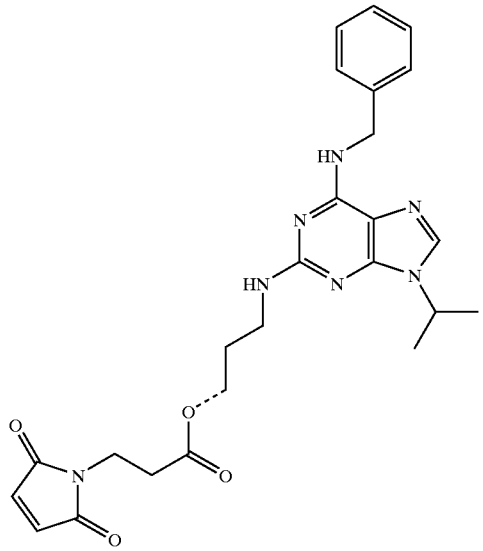

3-Maleimidopropionic acid (12.8 mg, 76 mmol) was dissolved in $CH_2Cl_2$ (1 mL). The mixture was stirred and DIC (5.3 mg, 42 mmol) in dry $CH_2Cl_2$ (0.5 mL) was added. The reaction was allowed to proceed with stirring for 40 min. Solvent was then removed under reduced pressure. The residue of 3-maleimidopropionic acid anhydride was redissolved in dry pyridine (0.5 mL). A solution of bohemine ({6-(benzylamino)-2-[(3-(hydroxypropyl)amino]-9- isopropylpurine}, 10.3 mg, 30 mmol) and DMAP (0.35 mg, 2 mmol) in dry pyridine (0.5 mL) was added and the mixture was stirred under $N_2$ for 1 h. It was then evaporated to dryness under reduced pressure. The residue was redissolved in DMF (1 mL) and applied to an RP-HPLC column (Vydac 218TP1022; 22×250 mm). The column was eluted at 9 mL/min using a gradient from 10–60% MeCN gradient in 0.1% aq. $CF_3COOH$ over 40 min (25° C.). Peak fractions were collected, monitored (Anal. RP-HPLC) and pooled as appropriate. After vacuum centrifugation, pure title compound (14.7 mg, 87.8%) was obtained. Anal. RP-HPLC: $t_R$=17.7 min (column (Vydac 218TP54, 0–60% MeCN in 0.1% aq. $CF_3COOH$ over 20 min, 1 mL/min., 25° C.; purity>95%, λ=200–300 nm). $^1$H-NMR ($CDCl_3$) and DE MALDI-TOF MS spectra were consistent with the proposed structure ($C_{25}H_{29}N_7O_4$=491.54).

O-{3-[3-(Cys-Arg-Gln-Ile-Lys-Ile-Trp-Phe-Gln-Asn-Arg-Arg-Met-Lys-Trp-Lys-Lys-OH) succinimido]propionoyl}-bohemine (SEQ ID No. 27)

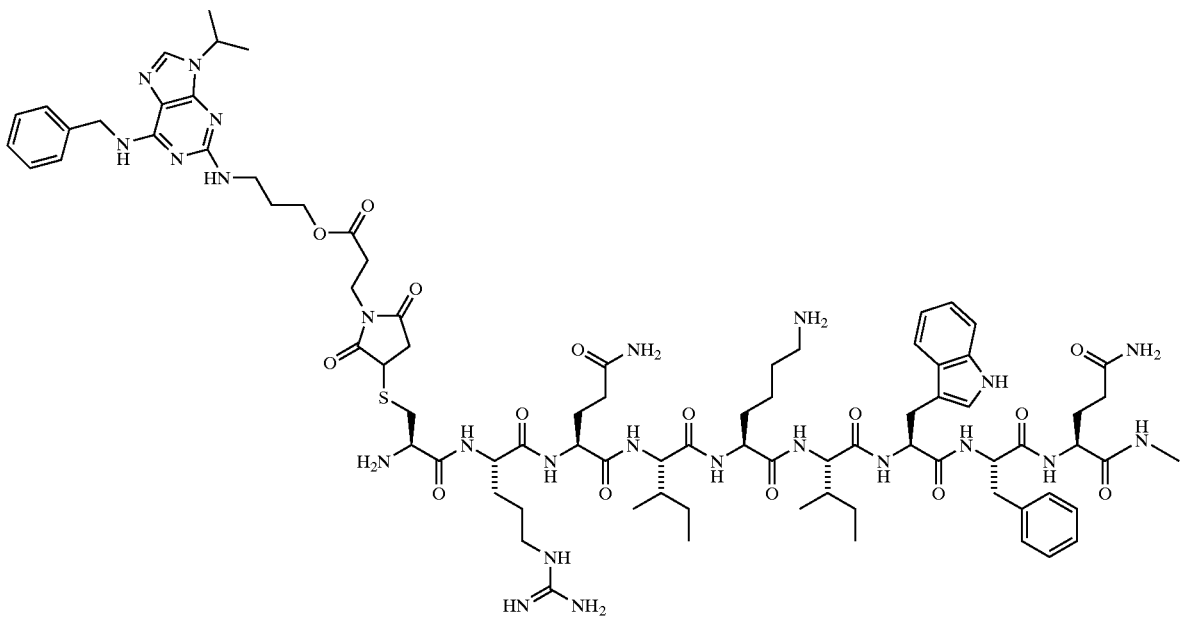

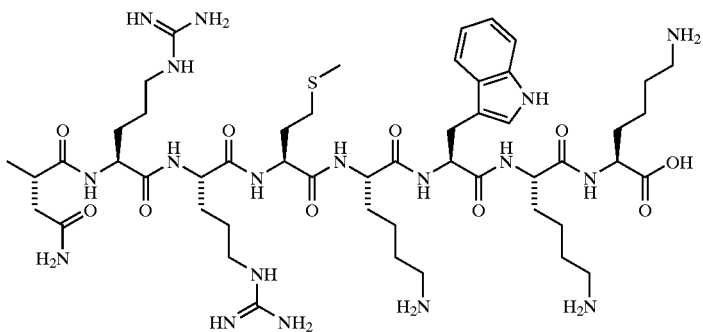

The product from the previous reaction (0.74 mg, 1.5 mmol) was dissolved in DMF (0.3 mL) and Et$_3$N (50 mL) was added. H-Cys-Arg-Gln-Ile-Lys-Ile-Trp-Phe-Gln-Asn-Arg-Arg-Met-Lys-Trp-Lys-Lys-OH (SEQ ID No. 27) (3.5 mg, 1.5 mmol), dissolved in DMF (0.25 mL) was then added. The mixture was stirred under N$_2$ and was monitored by anal. RP-HPLC. After 1 h, the reaction was complete. The mixture was filtered and applied to an RP-HPLC column (Vydac 218TP1022; 22×250 mm). The column was eluted at 9 mL/min using a gradient from 10–60% MeCN gradient in 0.1% aq. CF$_3$COOH over 40 min (25° C.). Peak fractions were collected, monitored (Anal. RP-HPLC) and pooled as appropriate. After vacuum centrifugation, pure title compound (1.7 mg, 40%) was obtained. Anal. RP-HPLC: $t_R$=15.0 min (Vydac 218TP54, 0–60% MeCN in 0.1% aq. CF$_3$COOH over 20 min, 1 mL/min., 25° C.; purity>95%, λ=200–300 nm). DE MALDI-TOF MS: [M+H]$^+$=2842 (C$_{132}$H$_{202}$N$_{42}$O$_{25}$S$_2$=2841.42).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A macromolecule comprising a drug moiety linked to a carrier moiety, wherein
   (a) the drug moiety is not a peptide, an oligonucleotide, cholesterol or biotin and is selected from the group consisting of a cardioprotective drug, an anti-arrhythmic drug, an anti-inflammatory drug, a neuroleptic drug, an anti-convulsant drug, an anxio-lytic drug, an antiviral drug, a diagnostic and a tri-substituted purine;
   (b) the carrier moiety is a homeobox peptide derived from the helix 3 sequence of the pAntp peptide or fragment thereof; and
wherein the carrier moiety facilitates the cellular internalization of the drug moiety.

2. The macromolecule of claim 1, wherein the drug moiety is a cardioprotective drug.

3. The macromolecule of claim 1, wherein the drug moiety is an anti-arrhythmic drug.

4. The macromolecule of claim 1, wherein the drug moiety is an anti-inflammatory drug.

5. The macromolecule of claim 1, wherein the drug moiety is a neuroleptic drug.

6. The macromolecule of claim 1, wherein the drug moiety is an anti-convulsant drug.

7. The macromolecule of claim 1, wherein the drug moiety is an anxio-lytic drug.

8. The macromolecule of claim 1, wherein the drug moiety is an antiviral drug.

9. The macromolecule of claim 1, wherein the drug moiety is a diagnostic.

10. The macromolecule of claim 1, wherein the drug moiety is a tri-substituted purine selected from the group consisting of olomoucine, roscovitine and bohemine.

11. The macromolecule of claim 1, wherein the carrier moiety comprises a peptide having the amino acid sequence set forth in SEQ ID NO 2.

12. The macromolecule of claim 1, wherein the carrier moiety further comprises a cysteine as a terminal residue.

13. The macromolecule of claim 1, wherein the carrier moiety comprises a carboxy terminal amino acid residue in which the carboxyl group is converted into a carboxamide group.

14. The macromolecule of claim 1, wherein the carrier moiety is comprised of D-amino acids.

15. The macromolecule of claim 1, wherein the carrier moiety is in retro-inverso form.

16. A macromolecule comprising a drug moiety linked to a carrier moiety, wherein
  (a) the drug moiety is not a peptide, an oligonucleotide, cholesterol or biotin;
  (b) the carrier moiety is a homeobox peptide derived from the helix 3 sequence of the pAntp peptide or fragment thereof; and
  (c) the drug moiety is linked to the carrier moiety by way of a linker moiety;
wherein the carrier moiety facilitates the cellular internalization of the drug moiety.

17. The macromolecule of claim 16, wherein the linker moiety is selected from the group consisting of bi-functional alkyl, aryl, aralkyl and peptidic moieties; multi-functional alkyl, aryl, aralkyl and peptidic moieties; alkyl, aryl and aralkyl aldehydes; alkyl, aryl and aralkyl acids; alkyl, aryl and aralkyl esters; alkyl, aryl and aralkyl anhydrides; sulphydryl groups, and carboxyl groups.

18. The macromolecule of claim 16, wherein the linker moiety is selected from the group consisting of maleimido benzoic acid derivatives, maleimido propionic acid derivatives and succinimido derivatives.

19. The macromolecule of claim 16 wherein the linker moiety is derived from the group consisting of cyanuric bromide, cyanuric chloride, carbonyldiimidazole, succinimidyl esters and sulphonic halides.

20. The macromolecule of claim 16, wherein the linker moiety is selected from the group consisting of (methylamino)benzoyl-Cys, succinimidobenzoyl-Cys, succinimidopropionoyl-Cys, β-alanyl-succinyl, acetyl-Cys and (4"-aminoanilino)-succinimidopropionoyl-Cys.

21. The macromolecule of claim 16, wherein the linker moiety comprises one to four amino acids selected from the group consisting of cysteine, glycine, glutamic acid and β-alanine.

22. The macromolecule of claim 16, wherein the linker moiety comprises a cysteine residue.

23. The macromolecule of claim 22, wherein the linker moiety further comprises β-alanine.

24. The macromolecule of claim 22, wherein the linker moiety further comprises glycine.

25. The macromolecule of claim 16, wherein the linker moiety is a network of lysine residues.

26. The macromolecule of claim 16, wherein the carrier moiety bears more than one drug moiety.

27. The macromolecule of claim 26, wherein the drug moieties are different.

28. The macromolecule of claim 26, wherein each drug moiety is linked to the carrier moiety by way of an identical linker moiety.

29. The macromolecule of claim 26, wherein each drug moiety is linked to the carrier moiety by a different linker moiety.

30. A macromolecule comprising a drug moiety covalently bound to a carrier moiety, wherein
  (a) the drug moiety is not a peptide, an oligonucleotide, cholesterol or biotin and is selected from the group consisting of a cardioprotective drug, an anti-arrhythmic drug, an anti-inflammatory drug, a neuroleptic drug, an anti-convulsant drug, an anxio-lytic drug, an antiviral drug, a diagnostic and a tri-substituted purine; and
  (b) the carrier moiety is a derivative of a homeobox peptide or fragment thereof comprising the amino acid sequence RRMKWKK (SEQ ID No:2), wherein
    (i) one or two amino acid residues are replaced by a naturally or non-naturally occurring amino acid residue;
    (ii) there is an insertion of one or more multivalent amino acids;
    (iii) one or more lysine residues are attached to at least one end;
    (iv) there is a cysteine as a terminal residue; or
    (v) any combination of (i)–(iv);
wherein the carrier moiety facilitates the cellular internalization of the drug moiety.

31. A macromolecule comprising a drug moiety linked to a carrier moiety, wherein
  (a) the drug moiety is not a peptide, an oligonucleotide, cholesterol or biotin;
  (b) the carrier moiety is a derivative of a homeobox peptide or fragment thereof comprising the amino acid sequence RRMKWKK (SEQ ID No:2), wherein
    (i) one or two amino acid residues are replaced by a naturally or non-naturally occurring amino acid residue;
    (ii) there is an insertion of one or more multivalent amino acids;
    (iii) one or more lysine residues are attached to at least one end;
    (iv) there is a cysteine as a terminal residue; or
    (v) any combination of (i)–(iv); and
  (c) the drug moiety is linked to the carrier moiety by way of a linker moiety;
wherein the carrier moiety facilitates the cellular internalization of the drug moiety.

32. The macromolecule of claim 10, wherein the tri-substituted purine is roscovitine.

33. The macromolecule of claim 30, wherein one or two amino acid residues are replaced by a naturally or non-naturally occurring amino acid residue.

34. The macromolecule of claim 30, wherein one or more lysine residues are attached to at least one end.

35. The macromolecule of claim 30, wherein one or more lysine residues are attached to at least one end.

36. The macromolecule of claim 30, wherein there is a cysteine as a terminal residue.

37. The macromolecule of claim 31, wherein one or two amino acid residues are replaced by a naturally or non-naturally occurring amino acid residue.

38. The macromolecule of claim 31, wherein there is an insertion of one or more multivalent amino acids.

39. The macromolecule of claim 31, wherein one or more lysine residues are attached to at least one end.

40. The macromolecule of claim 31, wherein there is a cysteine as a terminal residue.

* * * * *

UNITED STATES PATENT AND TRADEMARK OFFICE
CERTIFICATE OF CORRECTION

PATENT NO. : 6,992,169 B2
DATED : January 31, 2006
INVENTOR(S) : Peter Martin Fischer et al.

It is certified that error appears in the above-identified patent and that said Letters Patent is hereby corrected as shown below:

<u>Column 146,</u>
Lines 47 and 48, replace "wherein one or more lysine residues are attached to at least one end." with -- wherein there is an insertion of one or more multivalent amino acids. --.

Signed and Sealed this

Ninth Day of May, 2006

JON W. DUDAS
*Director of the United States Patent and Trademark Office*

SEQUENCE LISTING

<160> NUMBER OF SEQ ID NOS: 30

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
 1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Met Lys Trp Lys Lys
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Arg Arg Met Lys Trp Lys Lys
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asn Arg Arg Met Lys Trp Lys Lys
 1               5

<210> SEQ ID NO 5
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Gln Asn Arg Arg Met Lys Trp Lys Lys
 1               5                  10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Arg Met Lys Trp Lys Lys
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Lys Met Lys Trp Lys Lys
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Glu Lys Trp Lys Lys
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Gln Lys Trp Lys Lys
 1               5

<210> SEQ ID NO 10
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Orn
<220> FEATURE:
<223> OTHER INFORMATION: Description of Artificial Sequence: Synthetic
      peptide
```

```
<400> SEQUENCE: 10

Arg Arg Xaa Lys Trp Lys Lys
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Met Lys Gln Lys Lys
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Met Lys Trp Phe Lys
  1               5

<210> SEQ ID NO 13
<211> LENGTH: 7
<212> TYPE: PRT
<213> ORGANISM: Artificial Sequence
<220> FEATURE:
<221> NAME/KEY: MOD_RES
<222> LOCATION: (2)
<223> OTHER INFORMATION: Orn
<220> FEATURE:
<223> OTHER INFORMATION: Description of Artificial Sequence: Synthetic
      peptide

<400> SEQUENCE: 13

Arg Xaa Arg Lys Trp Lys Lys
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Met Trp Lys Lys Lys
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Met Lys Lys Trp Lys
  1               5
```

```
<210> SEQ ID NO 16
<211> LENGTH: 20
<212> TYPE: PRT
<213> ORGANISM: Artificial Sequence
<220> FEATURE:
<221> NAME/KEY: MOD_RES
<222> LOCATION: (4)
<223> OTHER INFORMATION: bAla
<220> FEATURE:
<223> OTHER INFORMATION: Description of Artificial Sequence: Synthetic
      peptide

<400> SEQUENCE: 16

Leu Leu Leu Ala Arg Gln Ile Lys Ile Trp Phe Gln Asn Arg Arg Met
 1               5                  10                  15

Lys Trp Lys Lys
            20

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Arg Gln Ile Lys Ile Trp Phe Gln Asn Arg Arg Met Lys Trp Lys
 1               5                  10                  15

Lys

<210> SEQ ID NO 18
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<220> FEATURE:
<221> NAME/KEY: MOD_RES
<222> LOCATION: (20)
<223> OTHER INFORMATION: Description of Artificial Sequence: Synthetic
      peptide
<220> FEATURE:
<223> OTHER INFORMATION: AMIDATION

<400> SEQUENCE: 18

Ala Arg Gln Ile Lys Ile Trp Phe Gln Asn Arg Arg Met Lys Trp Lys
 1               5                  10                  15

Lys Gly Cys Gly
            20

<210> SEQ ID NO 19
<211> LENGTH: 9
<212> TYPE: PRT
<213> ORGANISM: Artificial Sequence
<220> FEATURE:
<221> NAME/KEY: MOD_RES
<222> LOCATION: (2)
<223> OTHER INFORMATION: bAla
<220> FEATURE:
<221> NAME/KEY: MOD_RES
<222> LOCATION: (9)
<223> OTHER INFORMATION: Description of Artificial Sequence: Synthetic
      peptide
<220> FEATURE:
<223> OTHER INFORMATION: AMIDATION
```

```
<400> SEQUENCE: 19

Cys Ala Arg Arg Met Lys Trp Lys Lys
 1               5

<210> SEQ ID NO 20
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<220> FEATURE:
<223> OTHER INFORMATION: Description of Artificial Sequence: Synthetic
      peptide

<400> SEQUENCE: 20

Ala Arg Gln Ile Lys Ile Trp Phe Gln Asn Arg Arg Met Lys Trp Lys
 1               5                  10                  15

Lys

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: AMIDATION

<400> SEQUENCE: 21

Cys Arg Arg Met Lys Trp Lys Lys Cys
 1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Gln Ile Lys Ile Trp Phe Gln Asn Arg Arg Met Lys Trp Lys
 1               5                  10                  15

Lys

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: AMIDATION

<400> SEQUENCE: 23

Arg Gln Ile Lys Ile Trp Phe Gln Asn Arg Arg Met Lys Trp Lys Lys
 1               5                  10                  15

Gly Cys Gly
```

```
<210> SEQ ID NO 24
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<220> FEATURE:
<221> NAME/KEY: MOD_RES
<222> LOCATION: (8)
<223> OTHER INFORMATION: Description of Artificial Sequence: Synthetic
      peptide
<220> FEATURE:
<223> OTHER INFORMATION: AMIDATION

<400> SEQUENCE: 24

Ala Arg Arg Met Lys Trp Lys Lys
 1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: AMIDATION

<400> SEQUENCE: 25

Arg Gln Ile Lys Ile Trp Phe Gln Asn Arg Arg Met Lys Trp Lys Lys
 1               5                  10                  15

<210> SEQ ID NO 26
<211> LENGTH: 7
<212> TYPE: PRT
<213> ORGANISM: Artificial Sequence
<220> FEATURE:
<221> NAME/KEY: MOD_RES
<222> LOCATION: (7)
<223> OTHER INFORMATION: AMIDATION
<220> FEATURE:
<223> OTHER INFORMATION: Description of Artificial Sequence: Synthetic
      peptide

<400> SEQUENCE: 26

Arg Arg Met Lys Trp Lys Lys
 1               5

<210> SEQ ID NO 27
<211> LENGTH: 17
<212> TYPE: PRT
<213> ORGANISM: Artificial Sequence
<220> FEATURE:
<221> NAME/KEY: MOD_RES
<222> LOCATION: (17)
<223> OTHER INFORMATION: AMIDATION
<220> FEATURE:
<223> OTHER INFORMATION: Description of Artificial Sequence: Synthetic
      peptide

<400> SEQUENCE: 27

Cys Arg Gln Ile Lys Ile Trp Phe Gln Asn Arg Arg Met Lys Trp Lys
 1               5                  10                  15

Lys
```

```
<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Glu Gly Ala Lys Lys Ala Arg Gln Ile Lys Ile Trp Phe Gln Asn Arg
 1               5                  10                  15

Arg Met Lys Trp Lys Lys
            20

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

Cys Lys Lys Trp Lys Met Arg Arg Asn Gln Phe Trp Ile Lys Ile Gln
 1               5                  10                  15

Arg

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Cys Arg Gln Ile Lys Ile Trp Phe Gln Asn Arg Arg Met Lys Trp Lys
 1               5                  10                  15

Lys Gly Cys Gly
            20
```